United States Patent
Purdy

(10) Patent No.: US 12,053,266 B2
(45) Date of Patent: Aug. 6, 2024

(54) TRANSDUCER INTERFACE SYSTEM AND METHOD

(71) Applicant: Endophys Holdings, LLC, Dallas, TX (US)

(72) Inventor: Phillip Douglas Purdy, Dallas, TX (US)

(73) Assignee: Endophys Holdings, Inc., Dallas, TX (US)

( * ) Notice: Subject to any disclaimer, the term of this patent is extended or adjusted under 35 U.S.C. 154(b) by 711 days.

(21) Appl. No.: 14/553,922

(22) Filed: Nov. 25, 2014

(65) Prior Publication Data

US 2015/0112211 A1    Apr. 23, 2015

Related U.S. Application Data

(63) Continuation of application No. 13/946,646, filed on Jul. 19, 2013, now Pat. No. 8,926,520.

(Continued)

(51) Int. Cl.
*A61B 5/0215*    (2006.01)
*A61B 5/00*    (2006.01)
(Continued)

(52) U.S. Cl.
CPC ...... *A61B 5/02154* (2013.01); *A61B 5/02156* (2013.01); *A61B 5/02158* (2013.01);
(Continued)

(58) Field of Classification Search
CPC .............................. A61B 5/021; A61B 5/022
See application file for complete search history.

(56) References Cited

U.S. PATENT DOCUMENTS 4,446,715 A * 5/1984 Bailey .................... G01D 3/022
                                                              73/1.61
D285,112 S     8/1986 Sato et al.
(Continued)

OTHER PUBLICATIONS

Fiber Optic Measurement System/Fiber Optic Blood Pressure Sensors Instruction Manual. World Precision Instruments, Inc. 2004. (Year: 2004).*

(Continued)

*Primary Examiner* — Meredith Weare
(74) *Attorney, Agent, or Firm* — James H. Ortega; David W. Carstens; Carstens, Allen & Gourley, LLP

(57) ABSTRACT

A transducer interface system/method allowing conversion from an analog sensor input to a standardized analog output interface is disclosed. In some preferred embodiments the system/method permits a fiber optic pressure sensor to be interfaced to a standard patient care monitor (PCM) system using standardized Wheatstone Bridge analog interface inputs. Within this context the Wheatstone Bridge sensed output is defined by stimulus from the PCM and modulation of bridge element values by the conditioned output of an analog pressure sensor. The use of analog-to-digital-to-analog conversion in this transducer interface permits retrofitting of PCM devices having analog Wheatstone Bridge inputs with advanced patient monitoring sensors without the need for specialized modifications to the baseline PCM data collection framework. Methods disclosed herein include techniques to connect arbitrary types/numbers of analog sensors to traditional PCM systems without the need for PCM system hardware/software modifications.

24 Claims, 64 Drawing Sheets

Related U.S. Application Data

(60) Provisional application No. 61/673,895, filed on Jul. 20, 2012.

(51) Int. Cl.
| | |
|---|---|
| *A61B 5/024* | (2006.01) |
| *A61B 5/03* | (2006.01) |
| *G01L 9/00* | (2006.01) |
| *G01L 19/12* | (2006.01) |
| *G01L 27/00* | (2006.01) |

(52) U.S. Cl.
CPC .............. *A61B 5/024* (2013.01); *A61B 5/031* (2013.01); *A61B 5/032* (2013.01); *A61B 5/6853* (2013.01); *A61B 5/7225* (2013.01); *A61B 5/742* (2013.01); *G01L 9/00* (2013.01); *G01L 19/12* (2013.01); *G01L 27/007* (2013.01); *A61B 5/72* (2013.01)

(56) References Cited

U.S. PATENT DOCUMENTS

| | | | |
|---|---|---|---|
| 4,648,406 A * | 3/1987 | Miller | A61B 5/03 600/487 |
| 4,705,047 A | 11/1987 | Bailey | |
| 4,711,246 A | 12/1987 | Alderson | |
| 4,778,987 A | 10/1988 | Saaski et al. | |
| 4,787,396 A | 11/1988 | Pidorenko | |
| 4,858,615 A | 8/1989 | Meinema | |
| 4,901,735 A | 2/1990 | von Berg | |
| 5,048,524 A | 9/1991 | Bailey | |
| 5,107,847 A | 4/1992 | Knute et al. | |
| D329,702 S | 9/1992 | Sato et al. | |
| 5,325,865 A | 7/1994 | Beckman et al. | |
| 5,482,049 A * | 1/1996 | Addiss | A61B 5/02158 128/903 |
| 5,485,741 A | 1/1996 | Madison | |
| 5,568,815 A | 10/1996 | Raynes et al. | |
| 5,987,995 A * | 11/1999 | Sawatari | A61B 5/0215 600/480 |
| 6,120,457 A | 9/2000 | Coombes et al. | |
| 6,210,346 B1 | 4/2001 | Hall et al. | |
| 6,231,524 B1 | 5/2001 | Wallace et al. | |
| 6,471,646 B1 | 10/2002 | Thede | |
| 6,585,660 B2 | 7/2003 | Dorando et al. | |
| 7,144,372 B2 | 12/2006 | Ng et al. | |
| 7,318,807 B2 | 1/2008 | Ng | |
| 7,335,162 B2 | 2/2008 | Eide | |
| 7,361,147 B2 | 4/2008 | Ng | |
| 7,503,897 B2 | 3/2009 | Ng et al. | |
| 7,724,148 B2 | 5/2010 | Samuelsson et al. | |
| 7,946,997 B2 | 5/2011 | Hübinette | |
| 8,016,763 B2 | 9/2011 | Eide | |
| 8,066,681 B1 * | 11/2011 | Hall | A61B 5/031 604/533 |
| 2003/0045781 A1 | 3/2003 | Rosenheimer | |
| 2004/0082866 A1 * | 4/2004 | Mott | A61B 5/0215 600/394 |
| 2007/0088223 A1 | 4/2007 | Mann et al. | |
| 2007/0106165 A1 | 5/2007 | Tulkki | |
| 2007/0112274 A1 * | 5/2007 | Heitzmann | A61B 5/0002 600/485 |
| 2007/0287924 A1 | 12/2007 | Glocker et al. | |
| 2010/0234698 A1 * | 9/2010 | Manstrom | A61M 5/007 600/301 |
| 2010/0244813 A1 | 9/2010 | Hynd et al. | |
| 2010/0286536 A1 | 11/2010 | Samuelsson et al. | |
| 2011/0071407 A1 | 3/2011 | Hubinette et al. | |
| 2012/0071744 A1 | 3/2012 | Euliano | |
| 2012/0123223 A1 | 5/2012 | Freeman et al. | |
| 2012/0179012 A1 | 7/2012 | Saffarian | |
| 2012/0238869 A1 * | 9/2012 | Schmitt | A61B 5/0066 600/425 |
| 2013/0046190 A1 * | 2/2013 | Davies | A61B 5/742 600/486 |
| 2013/0131523 A1 | 5/2013 | Suchecki et al. | |
| 2013/0225941 A1 * | 8/2013 | Samuelsson | A61B 5/6851 600/300 |
| 2014/0180140 A1 * | 6/2014 | Alpert | A61B 5/0004 600/486 |
| 2015/0112211 A1 | 4/2015 | Purdy | |

OTHER PUBLICATIONS

RJC Enterprises, LLC "Supporting Instrumentation—Model 600" Fiber Optic Sensor, retrieved from www.rjcenterprises.net/model600.html, Nov. 1, 2012, 1 page.

\* cited by examiner

*Prior Art*

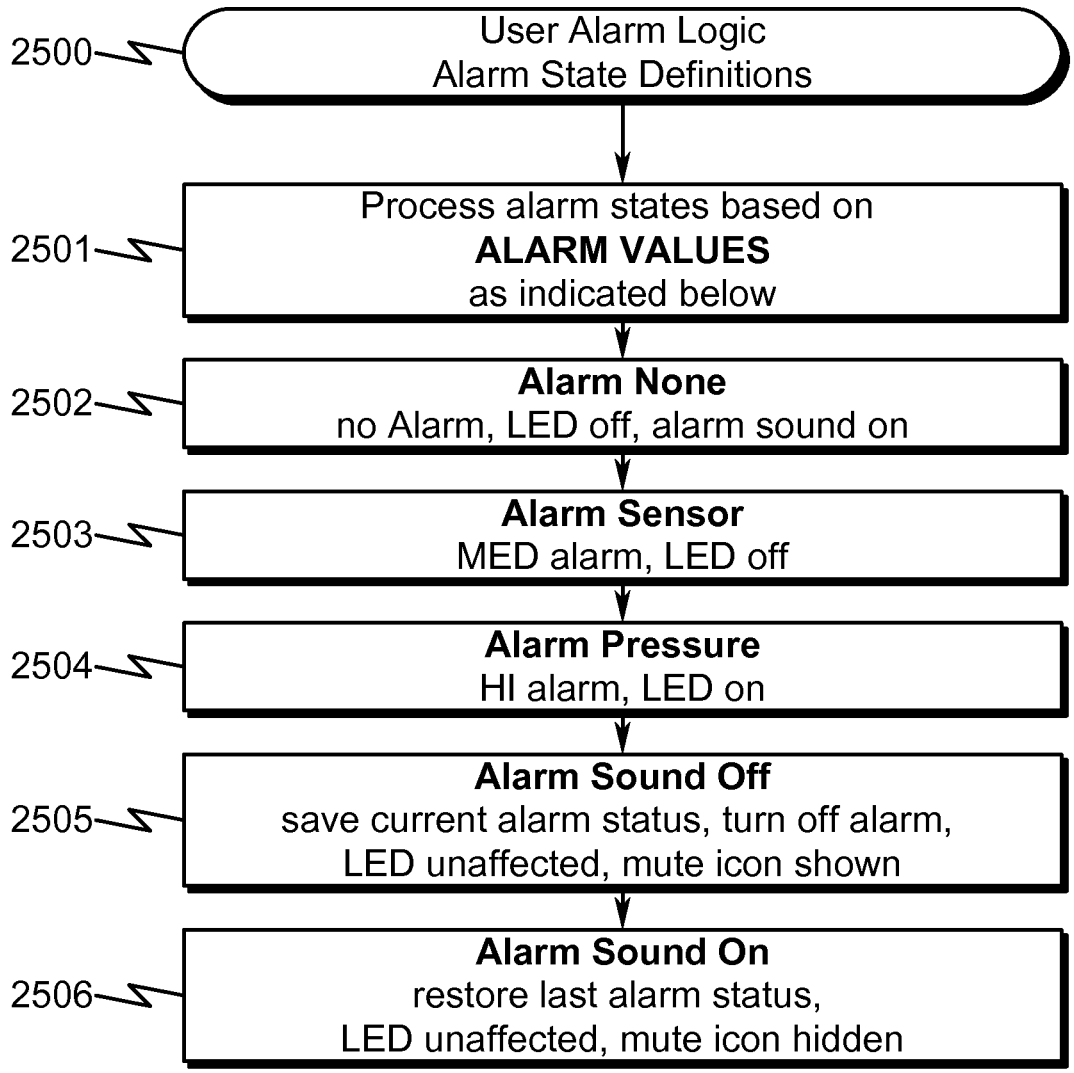
FIG. 25
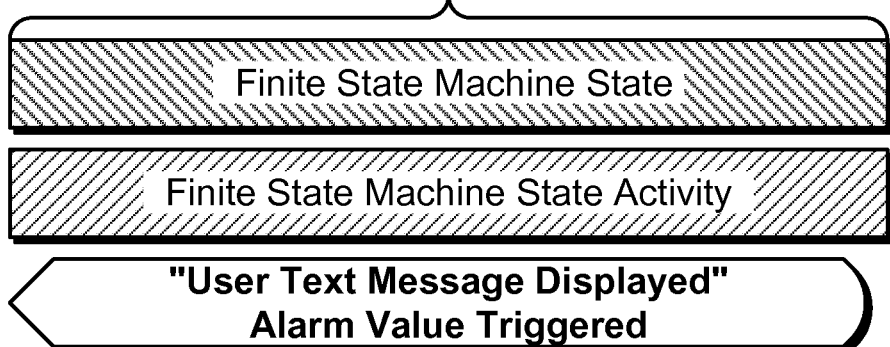

Prior Art

TEST CONDITIONS
Pulse rate 30; Systolic 67; Diastolic 16

MEASURED BPM SYSTOLIC/DIASTOLIC/MEAN
67/16/29

OBSERVATIONS / NOTES
Comparable results on PCM and BPM if systolic pressure sufficiently high

TEST CONDITIONS
Pulse rate 30; stroke volume decreased

MEASURED BPM SYSTOLIC/DIASTOLIC/MEAN
48/17/25

OBSERVATIONS / NOTES
No pressure detection with PCM external transducer

TEST CONDITIONS
Pulse rate 30; Lowered stroke volume

MEASURED BPM SYSTOLIC/DIASTOLIC/MEAN
29/18/21

OBSERVATIONS / NOTES
PCM pulse rate incorrect; no pressure readings from PCM transducer TEST CONDITIONS
Lowest possible stroke volume

MEASURED BPM SYSTOLIC/DIASTOLIC/MEAN
22/19/20

OBSERVATIONS / NOTES
No detection from PCM external transducer; only mean displayed

5200

TEST CONDITIONS
Pulse rate 40; lowest possible stroke volume

MEASURED BPM SYSTOLIC/DIASTOLIC/MEAN
76/72/73

OBSERVATIONS / NOTES
BP registering on all devices; no pulse rate on PCM transducer TEST CONDITIONS
Pulse rate 12

MEASURED BPM SYSTOLIC/DIASTOLIC/MEAN
87/70/74

OBSERVATIONS / NOTES
0 pulse and zero systolic/diatolic separation on PCM

TEST CONDITIONS
Pulse rate 12; very low stroke volume

MEASURED BPM SYSTOLIC/DIASTOLIC/MEAN
76/72/73

OBSERVATIONS / NOTES
No systolic/diastolic separation; zero rate detected on PCM transducer

PCM External Transducer Sensor

BPM Analog Input to PCM

TEST CONDITIONS
Pulse rate 12; lowest possible stroke volume; 1 mmHg systolic/diastolic

MEASURED BPM SYSTOLIC/DIASTOLIC/MEAN
73/72/72

OBSERVATIONS / NOTES
No systolic/diastolic separation; no rate detected on PCM transducer

5600

TEST CONDITIONS
Pulse rate 80; Lowest possible stroke volume

MEASURED BPM SYSTOLIC/DIASTOLIC/MEAN
78/72/74

OBSERVATIONS / NOTES
75/69/71 measured but no rate detected with PCM external transducer

FIG. 59
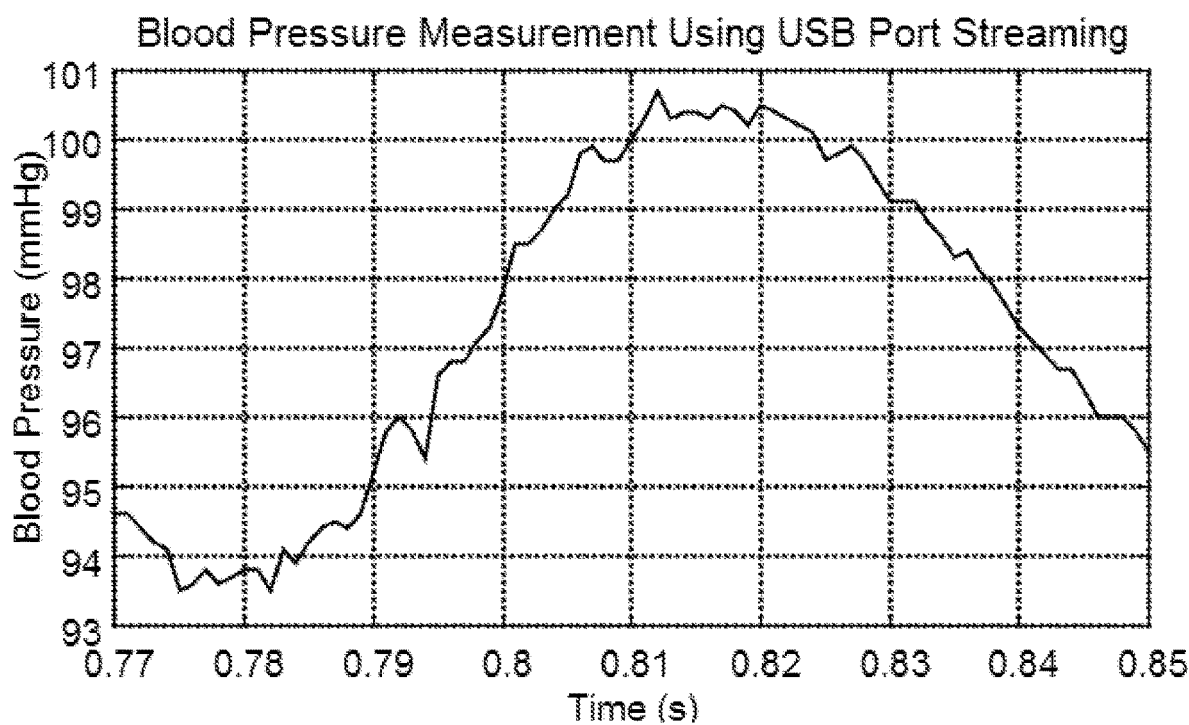

FIG. 63
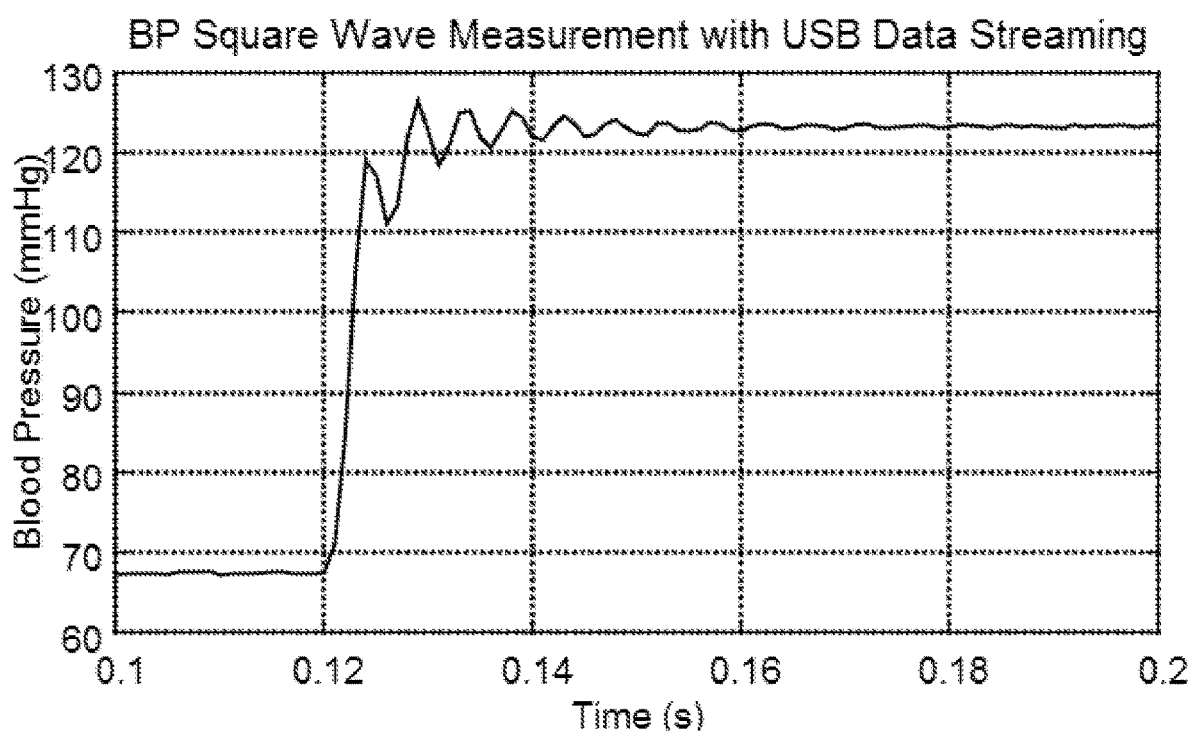

TRANSDUCER INTERFACE SYSTEM AND METHOD

CROSS REFERENCE TO RELATED APPLICATIONS

Utility Patent Applications

This application is a continuation patent application (CPA) and incorporates by reference U.S. Utility Patent Application for TRANSDUCER INTERFACE SYSTEM AND METHOD by inventors Phillip Douglas Purdy, et al., filed electronically with the USPTO on Jul. 19, 2013, with Ser. No. 13/946,646, EFS ID 16367706, confirmation number 8505.

This application claims benefit under 35 U.S.C. § 120 and incorporates by reference U.S. Utility Patent Applications for TRANSDUCER INTERFACE SYSTEM AND METHOD by inventors Phillip Douglas Purdy, et al., filed electronically with the USPTO on Jul. 19, 2013, with Ser. No. 13/946,646, EFS ID 16367706, confirmation number 8505.

Provisional Patent Applications

This application claims benefit under 35 U.S.C. § 119 and incorporates by reference United States Provisional Patent Applications for TRANSDUCER INTERFACE SYSTEM AND METHOD by inventors Phillip Douglas Purdy, et al., filed electronically with the USPTO on Jul. 20, 2013, with Ser. No. 61/673,895, EFS ID 13302368, confirmation number 8739.

PARTIAL WAIVER OF COPYRIGHT

All of the material in this patent application is subject to copyright protection under the copyright laws of the United States and of other countries. As of the first effective filing date of the present application, this material is protected as unpublished material.

However, permission to copy this material is hereby granted to the extent that the copyright owner has no objection to the facsimile reproduction by anyone of the patent documentation or patent disclosure, as it appears in the United States Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO A MICROFICHE APPENDIX

Not Applicable

FIELD OF THE INVENTION

The present invention generally relates to systems and methods for interfacing analog sensors. While not limitive of the invention teachings, the present invention may in some circumstances have application to situations in which a wide variety of medical patient monitoring sensors (blood pressure sensors, cerebrospinal fluid sensors, etc.) used in monitoring patients within a healthcare environment are interfaced to computerized Patient Care Monitor (PCM) systems.

PRIOR ART AND BACKGROUND OF THE INVENTION

Prior Art System Overview (0100)

Existing transducer interface systems that operate in the context of conventional patient care monitors (PCMs) are generally illustrated in FIG. 1 (0100). In this example, the patient (0101) is monitored using an analog sensor configured within a sensor bridge (0111). The analog sensor may comprise a wide variety of technologies and may be configured to sense a wide variety of patient conditions, including but not limited to blood pressure, temperature, etc. Within this context the sensor bridge (0111) is connected to a patient care monitor (PCM) (0112) that displays the current sensed status of the sensor bridge (0111) in response to excitation stimulus provided by the PCM (0112). The PCM system (0112) is often computerized and configured with software read from a computer readable medium (0113). Displays or other audio/video indicia within the PCM (0112) are interpreted by operators (0102) or other healthcare professionals.

Prior Art Method Overview (0200)

The prior art transducer interface system illustrated in FIG. 1 (0100) typically has an associated data collection method as generally illustrated in FIG. 2 (0200) comprising the following instantaneous analog processing steps:

(1) The analog sensor used to measure patient vital statistics is incorporated into a Wheatstone Bridge (0201);
(2) The Wheatstone Bridge is excited via a voltage source from the PCM (0202);
(3) The patient vital statistics are captured by the analog sensor within the Wheatstone Bridge (0203);
(4) The Wheatstone Bridge characteristics are modulated by the patient analog sensor (0204);
(5) The output of the Wheatstone Bridge is measured by the PCM and filtered/displayed on the PCM (0205); and
(6) Control is continuously passed to step (2).

In most circumstances the configuration of the Wheatstone Bridge is standardized with respect to the class of PCM performing the measurement. Thus, industry standards typically dictate the configuration and characteristics of the Wheatstone Bridge, with the associated analog sensors being chosen to conform to these specifications.

Prior Art Patent Publications/Present Invention Comparison

Patents containing prior art that are relevant to the present invention can be seen in the following issued U.S. patents:
NONINVASIVE BLOOD PRESSURE MONITORING SYSTEM, U.S. Pat. Nos. 7,503,897/7,361,147/7,318, 807/7,144,372: These patents fundamentally describe devices that convert non-invasive blood pressure (NIBP) sensor signal which is derived from a pneumatic sensor into a signal that can be interfaced to an invasive blood pressure monitor input. In contrast to this prior art, the present invention describes an invasive fiber optic blood pressure sensor which employs a fiber optic sensor with an invasive blood pressure monitor input and provides other functionality not described by these patents. The present invention uniquely integrates the output from a fiber optic signal conditioner, that itself receives inputs from an optical pressure sensor apparatus, with the excitation voltage output from a physiological monitor originally designed to interface with a fluidic external pressure transducer and generates an input to that monitor consisting of an accurate replication of the inputs that would be received from a Wheatstone Bridge external pressure transducer.

INTRACRANIAL PRESSURE MONITORING SYSTEM, U.S. Pat. No. 5,325,865: This patent describes an interface between an intracranial catheter mounted optical light emitting diode (LED) based pressure sensor and a patient care monitor (PCM). The device incorporates LED temperature compensation and uses the patient care monitor (PCM) excitation voltage for power. This prior art differs significantly from the present invention in that the present invention is based on fiber optic pressure transducers that are remotely stimulated by LEDs to excite the F-P cavity, does not require temperature compensation, and provides other functionality not described by this patent.

ARTERIAL LINE EMULATOR, U.S. Pat. No. 6,471,636: This patent describes a device that interfaces a non-invasive blood pressure monitor with an invasive blood pressure monitor. This patent disclosure significantly differs from the present invention in that the present invention interfaces an invasive fiber optic blood pressure sensor with an invasive blood pressure monitor input and provides other functionality not described by this patent.

SELF-POWERED INTERFACE CIRCUIT FOR USE WITH A TRANSDUCER SENSOR, U.S. Pat. No. 5,568,815: This patent describes an analog electronic device that interfaces a semiconductor transducer to a patient vital signs monitor. The semiconductor transducers described in this patent are configured in a Wheatstone Bridge circuit and the device is powered by the excitation voltage from the patient care monitor (PCM). This patent disclosure significantly differs from the present invention in that the present invention is based on fiber optic pressure transducers which are not based on a Wheatstone Bridge circuit, is implemented primarily using digital electronics, derives its power from batteries or utility AC power, and provides other functionality not described by this patent.

SIGNAL CONDITIONING DEVICE FOR INTERFACING INTRAVASCULAR SENSORS HAVING VARYING OPERATIONAL CHARACTERISTICS TO A PHYSIOLOGICAL MONITOR, U.S. Pat. No. 6,585,660: This patent describes a digital electronic device that is powered from a patient care monitor (PCM) excitation voltage and interfaces resistive sensor elements to a patient care monitor (PCM) with temperature compensating circuits. This patent disclosure significantly differs from the present invention in that the present invention is based on fiber optic pressure transducers which are not based on resistive sensor elements, derives its power from batteries or utility AC power, does not require temperature compensation, and provides other functionality not described by this patent.

None of these cited patents provides the capability of extending the range of existing PCM hardware by providing an interface to advanced analog sensor detection measurement systems.

Prior Art Deficiencies

The prior art transducer interface system/method illustrated in FIG. 1 (0100) and FIG. 2 (0200) respectively suffer from a variety of drawbacks, including but not limited to the following:

Most PCMs define limits on the electrical characteristics of the Wheatstone Bridge, resulting in a narrowing of acceptable analog sensors that can be used with the PCM. Generally speaking, an arbitrary analog sensor cannot be connected to a PCM that requires a limited/fixed Wheatstone Bridge electrical interface.

PCMs generally do not support fiber optic based blood pressure sensors.

PCMs generally do not support multi-channel analog sensors within a single sensor input.

PCMs are generally not adaptable to new types of IBP analog sensors that are not compatible with Wheatstone Bridge sensing interfaces.

PCMs generally incorporate low pass filtering to address noise present in the patient environment, resulting in poor high frequency BP measurement characteristics.

PCMs generally are susceptible to low frequency power line interference.

PCMs are generally incompatible with use in a MRI imaging environment.

PCMs generally have a difficult time in discriminating blood pressure readings with low heart rates and/or low systolic/diastolic pressure ratios.

PCMs generally have a significant delay (multiple seconds) in displaying real-time data acquired from traditional BP sensors.

PCMs generally do not provide reference pressure signals in digital form for ancillary processing by an external computer system.

PCMs are less immune to electromagnetic interference due to the wired nature of their sensor-to-computer interface.

PCMs generally do not provide significant electrical isolation of the patient from the monitoring device. Generally speaking, the use of wired interconnects from the PCM to the patient often results in the potential for electromagnetic interference as well as an unwanted electrical path to the patient's body. Better isolation in the form of an optical interface is generally not possible using conventional PCM technologies.

PCMs are generally configured with firmware that lacks any ability for field modifications or field reprogramming.

PCMs cannot stream real-time digital and/or analog pressure data to a general remote computer system for ancillary processing. While some prior art systems do permit data streaming, this feature is limited to similarly configured instruments in the same product line and not to a general purpose data analysis computer.

PCMs lack support for real-time and/or post-processing of collected data.

Many PCMs lack portability and the ability for battery powered operation.

One skilled in the art will no doubt be able to determine other deficiencies in the prior art that have as yet to be addressed by the prior art.

Objectives of the Invention

Accordingly, the objectives of the present invention are (among others) to circumvent the deficiencies in the prior art and affect the following objectives:
(1) Provide for a transducer interface system and method that permits a wide variety of analog sensor types to be interfaced to conventional PCM systems that require Wheatstone Bridge interfaces.
(2) Provide for a transducer interface system and method that permits high performance sensors to be attached to conventional PCMs.
(3) Provide for a transducer interface system and method that permits high sensitivity pressure sensors to be attached to conventional PCMs.
(4) Provide for a transducer interface system and method that permits high sensitivity blood pressure sensors to be attached to conventional PCMs.
(5) Provide for a transducer interface system and method that permits fiber optic blood pressure sensors to be attached to conventional PCMs.
(6) Provide for a transducer interface system and method that permits blood pressure sensors having wider dynamic range to be attached to conventional PCMs.
(7) Provide for a transducer interface system and method that permits blood pressure sensors having higher accuracy to be attached to conventional PCMs.
(8) Provide for a transducer interface system and method that permits blood pressure sensors having smaller form factors to be attached to conventional PCMs.
(9) Provide for a transducer interface system and method that permits multi-channel blood pressure sensors to be attached to conventional PCMs.
(10) Provide for a transducer interface system and method that permits catheter-based blood pressure sensors to be attached to conventional PCMs.
(11) Provide for a transducer interface system and method that permits neonatal blood pressure sensors to be attached to conventional PCMs.
(12) Provide for a transducer interface system and method that permits use of Fabry-Perot pressure sensors to measure pressure within a medical context (blood pressure, etc.).
(13) Provide for a transducer interface system and method that permits measurement of pressure using a Fabry-Perot pressure sensor positioned at the distal end of a medical device.
(14) Provide for a transducer interface system and method that permits measurement of pressure using a Fabry-Perot pressure sensor positioned at the distal end of a medical device, the medical device selected from a group consisting of a catheter, catheter incorporating a mounted balloon, vascular sheath, ventriculostomy catheter, ventricular shunt catheter, lumbar drain, and intracranial pressure monitor structure.

While these objectives should not be understood to limit the teachings of the present invention, in general these objectives are achieved in part or in whole by the disclosed invention that is discussed in the following sections. One skilled in the art will no doubt be able to select aspects of the present invention as disclosed to affect any combination of the objectives described above.

Contrasting the Present Invention with the Prior Art

Many medical circumstances involve various forms of physiological monitoring. These include simple temperature measurement by placement of a thermometer under the tongue, blood pressure measurement using a sphygmomanometer (blood pressure cuff), or other external monitoring techniques. For conditions requiring more precise or intensive monitoring, mechanisms have evolved over many decades to use electronic means and more invasive access to patient physiology. In the case of temperature measurement, these include temperature probes that may be internal to the body or on the skin.

In the case of blood pressure measurement, the most common sensing means involves placement of a catheter structure (usually in tubing) within an arterial fluid column. This catheter structure incorporates an external transducer (that is integrated with a Wheatstone Bridge for interfacing to a patient care monitor (PCM)) and extends from the patient to an intravenous (IV) dispensing pole). If the transducer is at the level of the heart, it provides reasonably accurate measurements of blood pressure under normal physiological circumstances. Since it samples at the end of a fluid column, however, it is subject to sources of error (misplacement of the transducer on the IV pole at a level higher or lower than the heart, clotting or other impedance of the signal conduction through the tubing). A Wheatstone Bridge works by application of an electrical current of a known strength across a resistive circuit which alters resistive properties based on the amount of pressure applied to the circuitry. The transducer is "zeroed" to atmospheric pressure at the beginning of the monitoring session to adjust the pressure relative to ambient air pressure. Subsequently, when a different pressure is applied to the circuit, the returning voltage is measured and the pressure is calculated. This mechanism of monitoring is applied to radial artery catheter monitoring of blood pressure by anesthesiologists during surgery or other invasive procedures and in intensive care units in which hemodynamic instability is a concern.

More recently, an electronic circuit technology analogous to the Wheatstone Bridge has been applied to wire sensors placed in the body with the transducer circuitry placed directly on the wire (U.S. Patent Application Publication 2007/0106165 A1), in which a sensor wire assembly comprises a sensor element at the tip of a guide wire and wire connectors connected to the sensor element which supply an excitation voltage and a readout voltage which is altered from the excitation voltage by the pressure applied across the sensor. While this circuitry is analogous to the Wheatstone Bridge via application of an excitation voltage and reading of a returning voltage, it does not work precisely as a Wheatstone Bridge insofar as the input voltage is not required to be supplied by a patient care monitor (PCM) and hence there is adaptive circuitry implied to communicate from the sensor circuitry to the patient monitor circuitry. This circuitry may utilize the monitor's excitation voltage or may use a "signal adapting circuitry" that may display a human-readable output corresponding to the sensed pressure. This reference discloses a standardized output in the form of an analog voltage output signal. It also envisions a wireless form of communication (Bluetooth, etc.) between the sensor wire circuitry and a patient monitor circuitry. Under some embodiments, the reference discloses a sensor assembly utilizing an input electronic circuitry, an output electronic circuitry, and an electronic communication to a patient monitor, all of which are analog in nature and based on a continuous voltage and resistance circuitry, rather than discrete, digital observations of pressure that enable more sophisticated data analysis.

This is further described in U.S. Pat. No. 7,946,997, in which the wire sensor described in the earlier patent is claimed in relation to another signal adapting circuitry that sends the output from the sensor across optical communication channels and then converts the optical communication back into an electronic signal for communication to a patient monitor. Hence, the optical communication channel is used to transmit the analog data from its source to its analog output.

Other patents and filings (U.S. Patent Application Publication 2010/0286536 and U.S. Pat. No. 7,724,148 B2) describe transceiver units related to the wire sensors described in the earlier patents and hence are based on analog signal technology from the sensors. They describe a wireless link from a transceiver unit to a communication unit that obviates the need for a physical, wired connection.

While the technology described above utilizes sensors placed inside the body to measure pressure, they are based on electronic resistance technology analogous to that in the Wheatstone Bridge described earlier. Each uses an input electrical signal that is modified across a resistive circuit and the pressure is "sensed" along a waveform generated by the continuous electrical input signal, and hence it is not a set of discrete observations of pressure and is not amenable to digital data analysis.

In contrast, the present invention uses a technology for pressure sensing incorporating optical signals transmitted along optical fibers from a light source to a sensor (Fabry-Perot sensor) at the opposite end of the optical fiber. The light is transmitted as discrete pulsations at very high frequencies (1000 pulses per second and higher) which reflect from the diaphragm in the sensor and return to the proximal optical fiber and are detected as discrete observations of pressures. Each reading is assigned a value based on gauge (calibration) factors of the individual diaphragm (input from a memory unit specific to that diaphragm) and based on an observation of atmospheric pressure obtained prior to insertion of the sensor into the patient ("zeroing function"). In a presently preferred invention embodiment, two light pulses are needed to obtain one pressure observation, hence a pulse rate of 1000 Hz produces a pressure reading rate of 500 Hz, with accuracy of <1 mm Hg. This highly accurate, high-frequency, digital readout of intravascular pressure is possible when a sensor is inserted in a patient's artery and has multiple potential advantages analytically. It also is not inherently subject to signal filtration functions applied in standard patient monitors or to 60 Hz interference resulting from electronic signals based on alternating current electrical sources that may be proximal to the patient. However, the collection of digital data based on fiber optic sensor technology at high sampling rates is inherently dissimilar to that obtained via sensors based on analog electrical interference technology such as that in a Wheatstone Bridge and in the sensor technology disclosed above.

Another technology is described in U.S. Patent Application Publication 2007/0287924. In this reference, the signal from an analog sensor passes through an analog-to-digital converter (A/D converter) to produce a digital signal and that signal is transmitted to a second converter (D/A converter) that converts the digital signal into an appropriate analog signal based on the excitation voltage from the patient care monitor. This reference uses a different approach to conversion of an analog sensor signal with variable excitation voltages in its electronics into a signal that communicates with a patient care monitor. It would not be applicable to a technology in which the acquisition technology is a digital sensor technology, such as a Fabry-Perot fiber optic sensor. Additionally, this reference does not provide a means for digital output of the data—it is confined to analog-to-digital and then digital-to-analog circuitry specifically designed to convert a non-Wheatstone Bridge transducer sensor to a Wheatstone Bridge type signal.

Yet another technology is described in U.S. Patent Application Publication 2003/0045781 A1, in which a device for communication of output from medical sensors with patient care monitors is claimed. It constitutes another version of a Wheatstone Bridge emulator in which an electronic signal from an electronic sensor is amplified to match that expected from the excitation signal from a patient care monitor. Again, it is a means of converting from one type of analog signal to a different type of analog signal for means of displaying on a standard clinical monitor.

Fabry-Perot sensors have extensive prior art related to multiple configurations of sensors and their use in medicine and industry, both for temperature and for pressure measurements (see U.S. Pat. Nos. 4,329,058; 4,897,542; 5,297,437). While much of this basic intellectual property protection has expired, multiple variations on construction of sensors have been invented in recent years. However, variations on the structure of sensors or their light properties do not bear on the present invention, which envisions a plurality of potential sensor structures, all based on fiber optic sensor technology with digital output from the signal conditioners with which they are mated. The sensor particulars may all be adaptable to the data management described herein. The primary vascular use of Fabry-Perot sensors has historically been in intraortic balloon pumps, owing to their high sampling rate and high accuracy. However, their routine use in other applications has been hindered by their incompatibility with existing clinical care monitors. While existing Wheatstone Bridge and other electrically-actuated sensors deliver analog outputs compatible with or adaptable to clinical care monitors, the discretely sampled pressures with numerical digital outputs have heretofore not been displayed on clinical care monitors. While such display would have the advantage of utility with widely available monitors, fiber optic pressure sensors deliver information of such fidelity that degradation of the information to that displayed on monitors, combined with the more inexpensive and readily available Wheatstone Bridge technology which is matched to the patient care monitors in fidelity and sampling rate has been an economic impediment to implementation of the Fabry-Perot fiber optic technology in a wider clinical sphere.

The current invention addresses that technological gap by providing a means of conversion of the digital data acquired via a fiber optic Fabry-Perot sensor to an analog signal compatible with patient care monitors (PCMs) while maintaining a separate output (a USB port in some preferred invention embodiments) that transmits the full-fidelity data from the sensor to a device (computer, etc.) capable of higher-level analysis than that enabled by the analog output. Additionally, the present invention provides a display of pressure data taken directly from the fiber optic signal conditioner, thus showing the higher fidelity data acquired from the sensor, even under circumstances where a device may not be attached to the USB port or to the port for the patient care monitor. In a presently preferred embodiment, pressures are sampled at 1000 Hz frequency over four seconds, and the peak pressure during this time period is displayed as the systolic pressure, the trough pressure is displayed as the diastolic pressure, and the arithmetic mean of all pressure readings is displayed as the mean arterial pressure. The cycle refreshes every 4 seconds.

While Wheatstone Bridge emulation for electronic sensors may be construed to exist in prior art (U.S. Pat. No. 7,946,997 B2), such emulation in that disclosure involved the modification of the analog output from the sensor, based on its input current, to match the expected output to a clinical patient monitor, based on the excitation current from the monitor. That differs significantly from the algorithm required to convert the digital stream of data from a fiber optic Fabry-Perot sensor (using an interferometer or ratiometric approach) into an analog output in which the input current from the monitor is read and the numerical readings are converted to an output current that the monitor displays as though it were reading its input from a Wheatstone Bridge, such as is embodied in the current invention.

By achieving display of converted analog-to-digital output from the sensor, output to a patient care monitor through use of the Wheatstone Bridge transformation of the digital output described above, and direct streaming of data through a digital communications port (serial USB, in the current case), the present invention is both novel and more robust and flexible than other current pressure-sensing analytic technologies.

BRIEF SUMMARY OF THE INVENTION

System Overview

The present invention in various embodiments addresses one or more of the above described OBJECTIVES in the following manner. The present invention generally comprises an analog-to-digital-to-analog conversion process in which an analog sensor input is converted to digital and then compensated using calibration factors. The results of this compensated digital data are then converted to analog and presented to a Wheatstone Bridge emulator that receives excitation input from an external PCM (or other stimulus system). The excitation input from the PCM is modulated by the excitation input from the external PCM to emulate the characteristics of a conventional Wheatstone Bridge, resulting in a transparent presentation of the converted analog sensor data to the PCM for analysis/display. This analog-to-digital-to-analog conversion process permits high performance sensors to be attached to conventional PCM system hardware without the need for any PCM modifications. Additionally, individual analog sensor calibration factors ensures that the analog sensors need not be trimmed or compensated for by the PCM to ensure accurate measured sensor results.

Method Overview

The present invention system may be utilized in the context of an overall transducer interface method, wherein the transducer interface system described previously operates in conjunction with application software read from a computer readable medium that executes on a variety of computerized hardware that includes but is not limited to microcontrollers, personal computers, laptops, tablet computers, cellphones, smartphones, and the like.

BRIEF DESCRIPTION OF THE DRAWINGS

For a fuller understanding of the advantages provided by the invention, reference should be made to the following detailed description together with the accompanying drawings wherein:

FIG. 25 illustrates exemplary user alarm state definitions and associated alarm values associated with a preferred exemplary embodiment of the present invention;

FIG. 59 illustrates an exemplary blood pressure measurement fine detail result graph obtained via USB data streaming from a preferred exemplary embodiment of the present invention;

FIG. 63 illustrates an exemplary mechanically generated square-wave rising edge blood pressure measurement fine detail result graph obtained via USB data streaming from a preferred exemplary embodiment of the present invention.

DESCRIPTION OF THE PRESENTLY PREFERRED EXEMPLARY EMBODIMENTS

Figure 1:
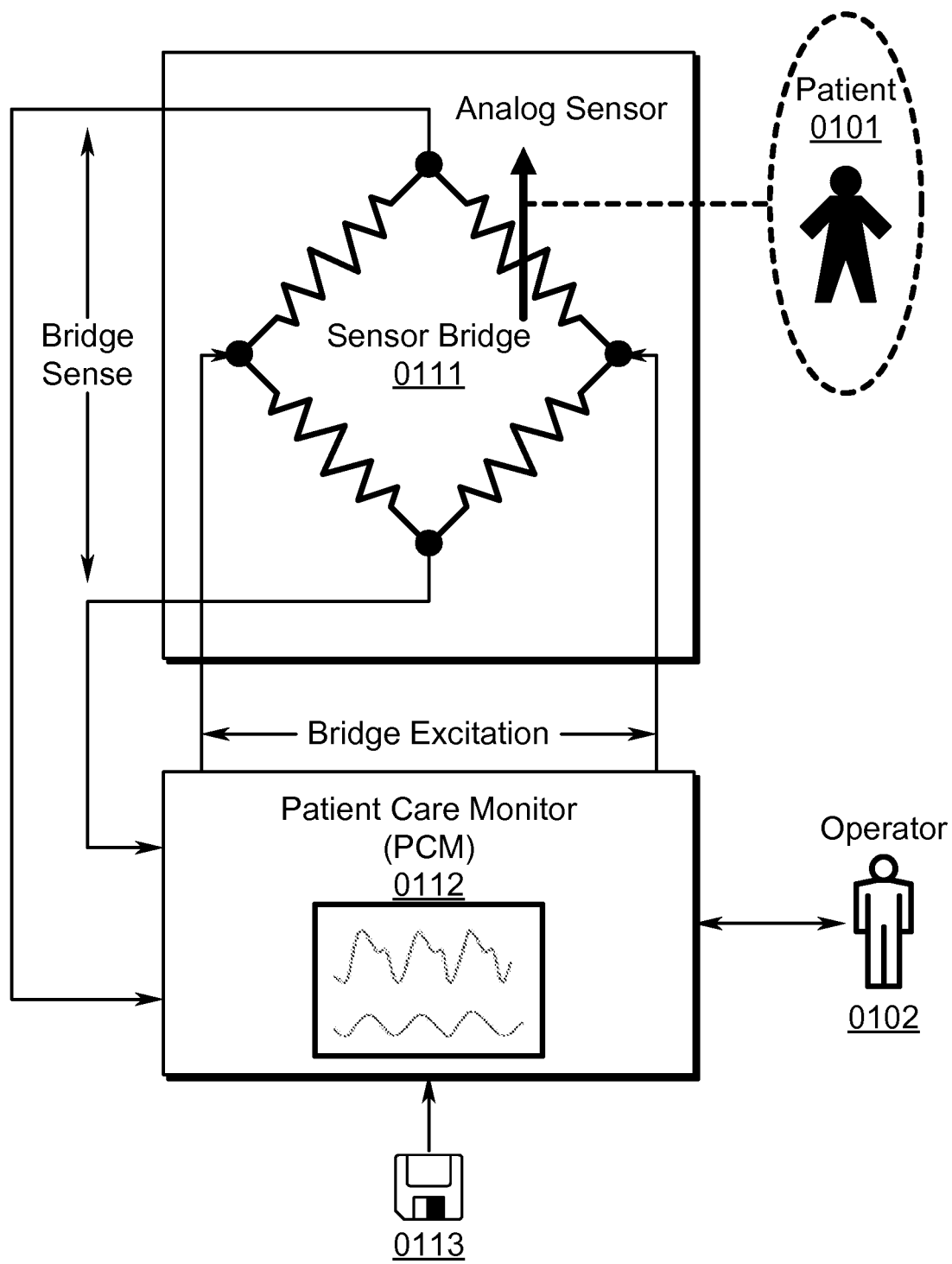
FIG. 1 illustrates a system block diagram of a prior art transducer interface system as applied to an analog patient status sensor monitored by a patient care monitor (PCM)
Figure 2:
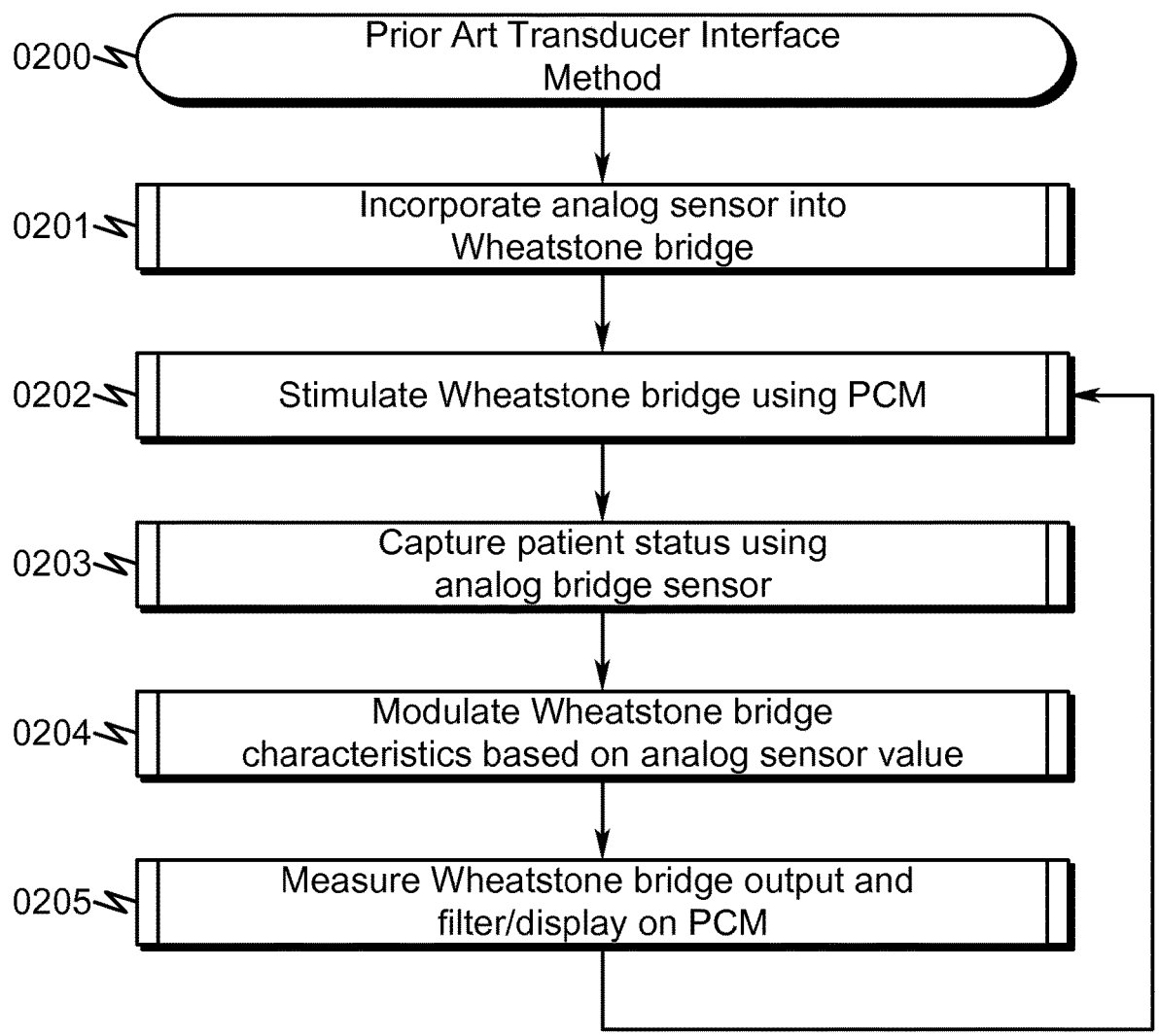
FIG. 2 illustrates a method flowchart of a prior art transducer interface method as applied to an analog patient status sensor monitored by a patient care monitor (PCM)

While the present invention is susceptible of embodiment in many different forms, there is shown in the drawings and will herein be described in detailed preferred embodiment of the invention with the understanding that the present disclosure is to be considered as an exemplification of the principles of the invention and is not intended to limit the broad aspect of the invention to the embodiment illustrated.

The numerous innovative teachings of the present application will be described with particular reference to the presently preferred embodiment, wherein these innovative teachings are advantageously applied to the particular problems of a TRANSDUCER INTERFACE SYSTEM AND METHOD. However, it should be understood that this embodiment is only one example of the many advantageous uses of the innovative teachings herein. In general, statements made in the specification of the present application do not necessarily limit any of the various claimed inventions. Moreover, some statements may apply to some inventive features but not to others.

BPM not Limitive

Much of the discussion of the present invention will center on a blood pressure monitoring (BPM) system embodiment. However, the teachings of the present invention are not strictly limited to the measurement of blood pressure. Thus, while the term "BPM" is used to identify the present invention in a variety of embodiments, it does not limit the invention to blood pressure measurement.

Analog Sensor Not Limitive

Within the context of the present invention, the term "analog sensor" should be broadly construed to include sensors having analog and/or digital interfaces.

Fiber Optic Sensor Not Limitive

The present invention anticipates a wide variety of fiber optic pressure sensors may be incorporated in various invention embodiments, including but not limited to fiber optic sensors utilizing an interferometer and/or ratiometric measurement techniques.

Computer Device Not Limitive

The present invention may utilize a wide variety of computing devices in various embodiments described herein. However, the present invention is not specifically limited to implementation with a given type of computing device. Therefore, terms such as "computer," "microcontroller," "MCU," "digital signal processor," "DSP," "laptop," "smartphone," "tablet computer," and the like should be considered synonymous in this context and given their widest possible interpretation consistent with the remaining teachings of the present invention.

Blood Pressure Sensor Not Limitive

Within the context of the present invention, the term "blood pressure sensor" should be broadly construed to include any sensor that measures pressure, whether applied to blood pressure monitoring or some other type of pressure sensor monitoring.

Pulse Rate Not Limitive

Within the context of the present invention description, the terms "heart rate," "pulse rate," and the like are synonymous.

Computer Not Limitive

The present invention anticipates a wide variety of computing devices may be used to implement the various aspects of the present invention and makes no limitation on the type of computing device that may be used to implement these functions. Thus, the term "computer," "computing device" and their derivatives should be given the broadest possible definition in this context.

Patient Care Monitor (PCM) Not Limitive

Within the present invention description the terms "Patient Care Monitor," "Patient Monitor," and "PCM" are synonymous. Furthermore, these terms should be given their broadest possible meaning in that PCM systems may include a wide variety of digital and/or analog systems used to monitor patient conditions and provide diagnostic information used within the healthcare environment.

Replication Not Limitive

The present invention may in some preferred embodiments implement multiple pressure sensing channels and/or analysis functions. Within this context, the term "replication" shall also include the use of multiplexing, wherein multiple pressure sensor inputs are multiplexed into a single pressure sensor measurement system.

Computer Communication Not Limitive

The present invention anticipates the use of computer communication between a given BPM system and another computer system. This communication may also permit BPM-to-BPM communication for the purposes of supporting multiple BPM measurement systems and multi-way interoperability between a plethora of BPM systems configured to operate cooperatively. Cooperative sharing of data, and processing and storage resources in these configurations allows the ability to combine not only multiple sensors, but also to aggregate data analysis to provide a more timely and comprehensive evaluation of pressure data than could be presented using only data and resources from only a single BPM.

Typical System Context

Overview

The present invention in a preferred embodiment is an electronic interface device that provides compatibility between one or more physiological fiber optic sensors (transducers) and conventional invasive arterial blood pressure (IBP) inputs to a common physiological patient care monitor (PCM). Various invention embodiments integrate the output from a signal conditioner, that itself receives inputs from a fiber optic sensor apparatus, with the output from a physiological monitor originally designed to interface with an external pressure transducer and generates an input to that monitor consisting of an accurate replication of the inputs that would be received from a Wheatstone Bridge external pressure transducer. The signal conditioner may be defined as an electro-optical unit that controls, processes, and converts the pressure modulated light signal from the transducer into electrical signals for subsequent interpretation. The present invention converts the optical sensor data to electrical signals that may then be interpreted by a conventional patient care monitor (PCM) and/or is retained and displayed directly on the device. The embodiment accurately emulates a fluidic IBP transducer and supplies electrical signals to its output that are indistinguishable from a conventional fluidic blood pressure sensor. It also supports modern computer communications interfaces and analog/digital human interface status indicators. Various preferred invention embodiments are designed to be used primarily in surgical procedures and critical patient care situations where the accuracy and timeliness of IBP systolic and diastolic measurements are very important. The present invention explicitly supports disposable fiber optic sensors that may be incorporated into other medical devices such as catheters and sheaths.

Fiber Optic Pressure Transducers

Modern fiber optic pressure transducers are less than 500 microns in diameter and are constructed using micro-machining manufacturing techniques. These tiny silicon-glass transducers are attached to the distal end of a standard fiber optic cable and are surgically placed into a human or animal body for IBP sensing. The proximal end of the sensor cable (which can be arbitrarily long) is attached through a fiber optic connector to an electro-optical signal conditioner unit that controls, processes and converts the pressure modulated light signal from the transducer into electrical signals for subsequent interpretation. Although fiber optic transducer systems have been used for blood pressure measurement as laboratory instruments, they have incompatible electrical output connections that do not allow them to be attached to conventional patient care monitors (PCMs). This limitation has kept these devices from gaining widespread use. The present invention in some preferred embodiments creates the sensor-to-monitor compatibility as well as providing expanded functionality for enhanced applications such as real time analysis of IBP waveforms and dynamic control of data acquisition and display.

PCM Interface

Figure 3:
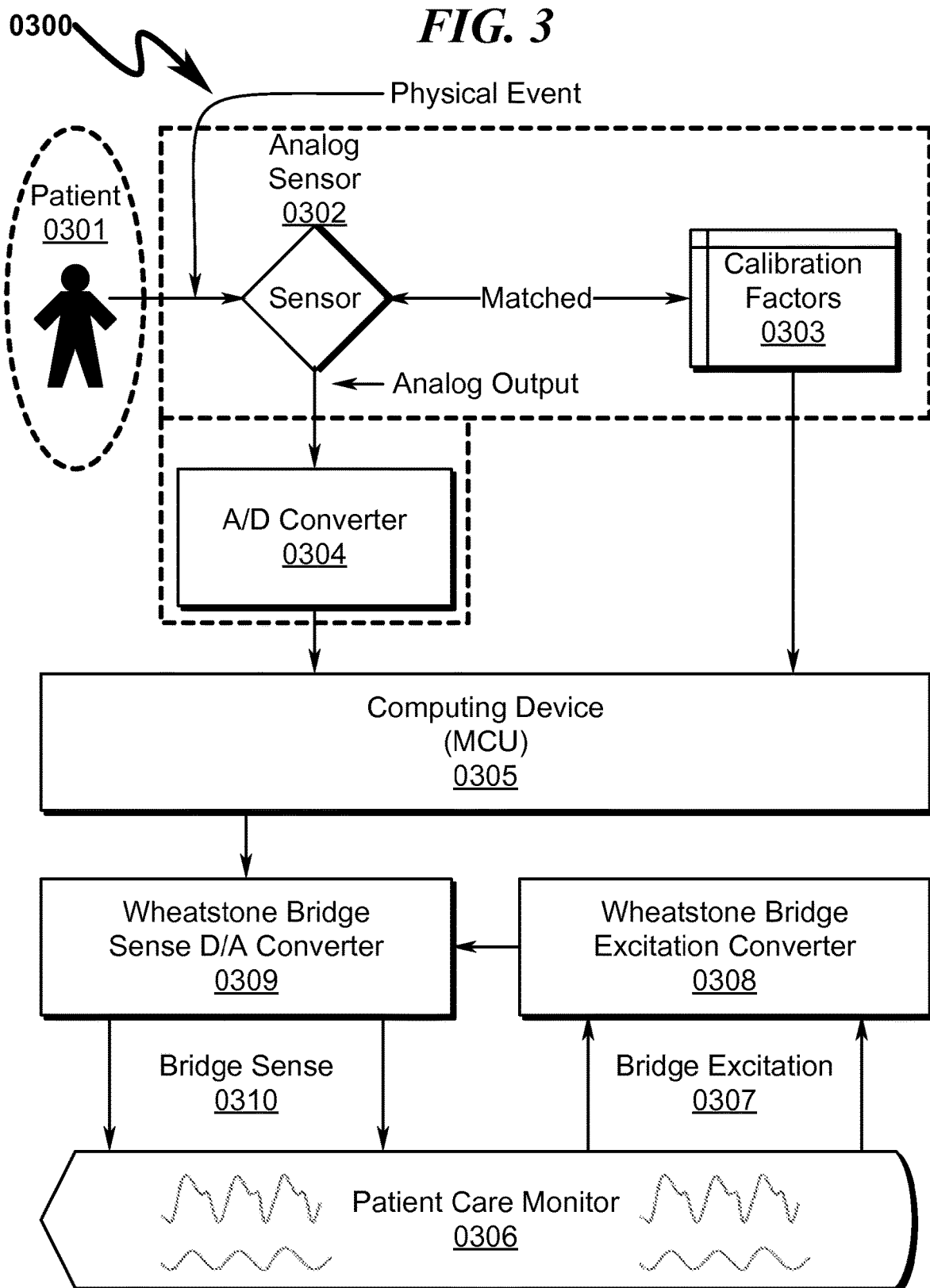
FIG. 3 illustrates a system block diagram of a preferred exemplary system embodiment of the present invention transducer interface system as applied to an analog patient status sensor monitored by a patient care monitor (PCM)

The present invention may be implemented as a self-contained unit that has a fiber optic transducer connection as an input source and communicates with a patient care monitor (PCM) as its output as generally depicted in FIG. 3 (0300). The interface essentially acts to directly emulate the electrical interface characteristics of conventional fluidic pressure transducers (that common patient care monitors (PCMs) are compatible with) while providing much more accurate blood pressure data derived from a fiber optic sensor. Electrically emulating a conventional fluidic transducer uniquely allows a fiber optic pressure sensor to be used with a wide variety of existing physiological patient care monitors (PCMs) without modification of those monitors.

BPM Exemplary Application

Fiber optic pressure sensors are extremely accurate and when placed in an arterial blood vessel provide significantly better real time blood pressure information to a clinician. Specifically, medical personnel such as cardiologists, vascular surgeons, anesthesiologists, neurosurgeons, interventional radiologists, trauma physicians, emergency medical technicians, etc. all need accurate real time indications of a patient's arterial blood pressure during critical care situations. Fiber optic sensors are also immune to the effects of electromagnetic radiation and can be used in intense radiological imaging environments without degradation, thus providing the ability to provide superior real time measurements in many clinical settings.

Basic Theory of Operation

A conventional fluidic IBP sensor uses a Wheatstone Bridge circuit (or a variant thereof) where the legs of the bridge circuit incorporate resistive or strain gauge elements as generally depicted in FIG. 1 (0100). An excitation voltage is applied by a conventional IBP monitor to the input of the bridge to provide an energizing voltage and a reference for the output signal. When pressure is applied to the sensor(s) the bridge becomes unbalanced and creates a small analog signal that is directly proportional to the pressure activated change in the sensor resistance. The most common sensitivity value for these sensors is 5-microvolts/volt/mmHg. Although the sensitivity value is reasonably standard in the industry various manufacturers of patient care monitors (PCMs) use a variety of excitation voltages.

The present invention has an adaptive Wheatstone Bridge emulation function as generally depicted in FIG. 3 (0300) that senses the instantaneous excitation voltage from the patient care monitor (PCM) to which it is connected. It then automatically applies corrections to the absolute fiber optic pressure sensor signal to scale it to the appropriate values needed by the specific patient care monitor (PCM).

The present invention incorporates optional user human interfaces that provide information and control functions. Among these functions are:
- an electronic display capable of showing systolic blood pressure, diastolic blood pressure, mean blood pressure, and/or heart rate values and system status, light indicators showing system condition and alarms, an audio alarm annunciator, and manual switch controls for turning the unit on and off, audio muting, etc.; and
- an automatic zeroing function to atmospheric pressure when the sensor is connected to the signal conditioner prior to the insertion of the device into a body cavity of a patient.

These display and control functions are also available through a computer communications port for software application control.

The present invention may be powered selectively by either batteries or by a standard AC utility outlet. The battery can be either primary cells or rechargeable batteries.

System Overview (0300)

The present invention system may be seen in an overview context as generally illustrated in FIG. 3 (0300), wherein the system is applied to collection of data associated with a patient in a healthcare application context. Within this context, the patient (0301) is monitored by an analog sensor (0302) that has associated with it calibration factors (0303) that describe a conversion from the analog values produced by the sensor (0302) to a normalized set of standardized values. For example, a fiber optic pressure sensor might incorporate calibration factors converting measured optical transit delays (or other measured physical data associated with the optical sensor) to absolute pressure values.

The analog sensor (0302) analog output is converted to digital by an A/D converter (0304) and this information with the calibration factors (0303) is presented to a microcontroller (MCU) (0305) (or other computing device) for integration. In this step the raw analog sensor (0302) information is compensated by the calibration factors (0303) to produce sensor data that may be interpolated if necessary to produce accurate sensor information that is accurate over a wide dynamic range of sensor inputs.

Within this general system context in many preferred configurations a patient care monitor (PCM) (0306) generates analog excitation signaling (0307) that is used as a scaling reference for the Wheatstone Bridge emulator. The analog sensor A/D converter data and the calibration factor data are combined to produce a Wheatstone Bridge sense output that is converted by a D/A converter (0309) for combination with the excitation signaling data and subsequent presentation to the PCM (0306) as an analog bridge sense signal (0310). This analog bridge sense signal (0310) represents a fully compensated and calibrated conversion of the analog sensor (0302) output that is scaled in proper form for processing and display by the PCM (0306).

Method Overview (0400)

Figure 4:
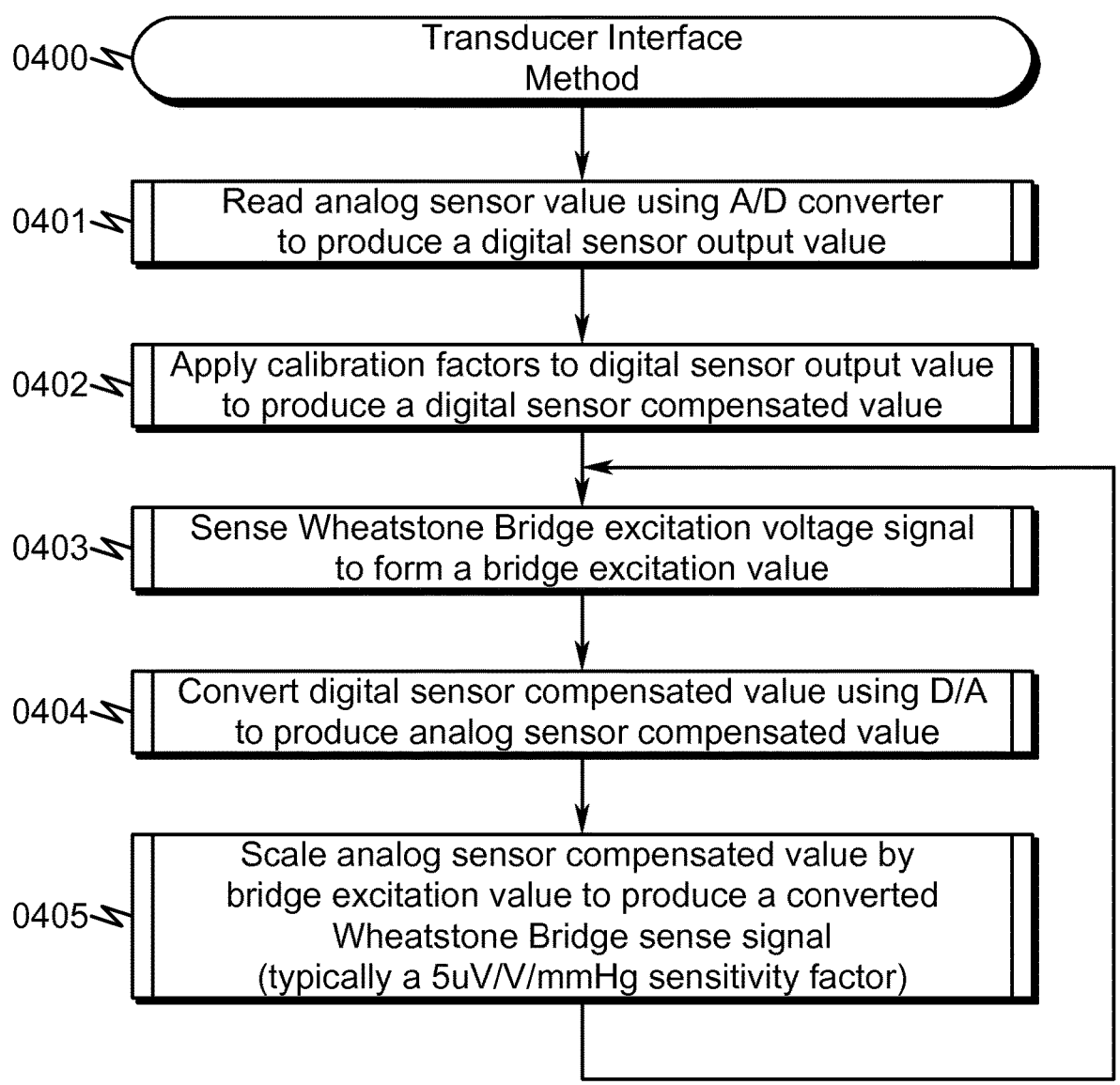
FIG. 4 illustrates a method flowchart of a preferred exemplary method embodiment of the present invention transducer interface method as applied to an analog patient status sensor monitored by a patient care monitor (PCM)

The present invention method may be seen in an overview context as generally illustrated in the flowchart of FIG. 4 (0400), and can be generally described as a transducer interface method that comprises the following method steps:
(1) Sampling an analog sensor output signal using an A/D converter to produce a digital sensor output value (0401);
(2) Applying calibration factors to the digital sensor output value to produce a digital sensor compensated value (0402);
(3) Sensing a Wheatstone Bridge excitation voltage signal to form a bridge excitation reference voltage (0403);
(4) Converting the digital sensor compensated value from digital to analog using an A/D converter to produce an analog sensor compensated value (0404); and
(5) Scaling the analog sensor compensated value by the bridge excitation value to produce a converted Wheatstone Bridge sense signal (0405).

One skilled in the art will recognize that these method steps may be augmented or rearranged without limiting the teachings of the present invention.

System Block Diagram Description (0500, 0600)

Figure 5:
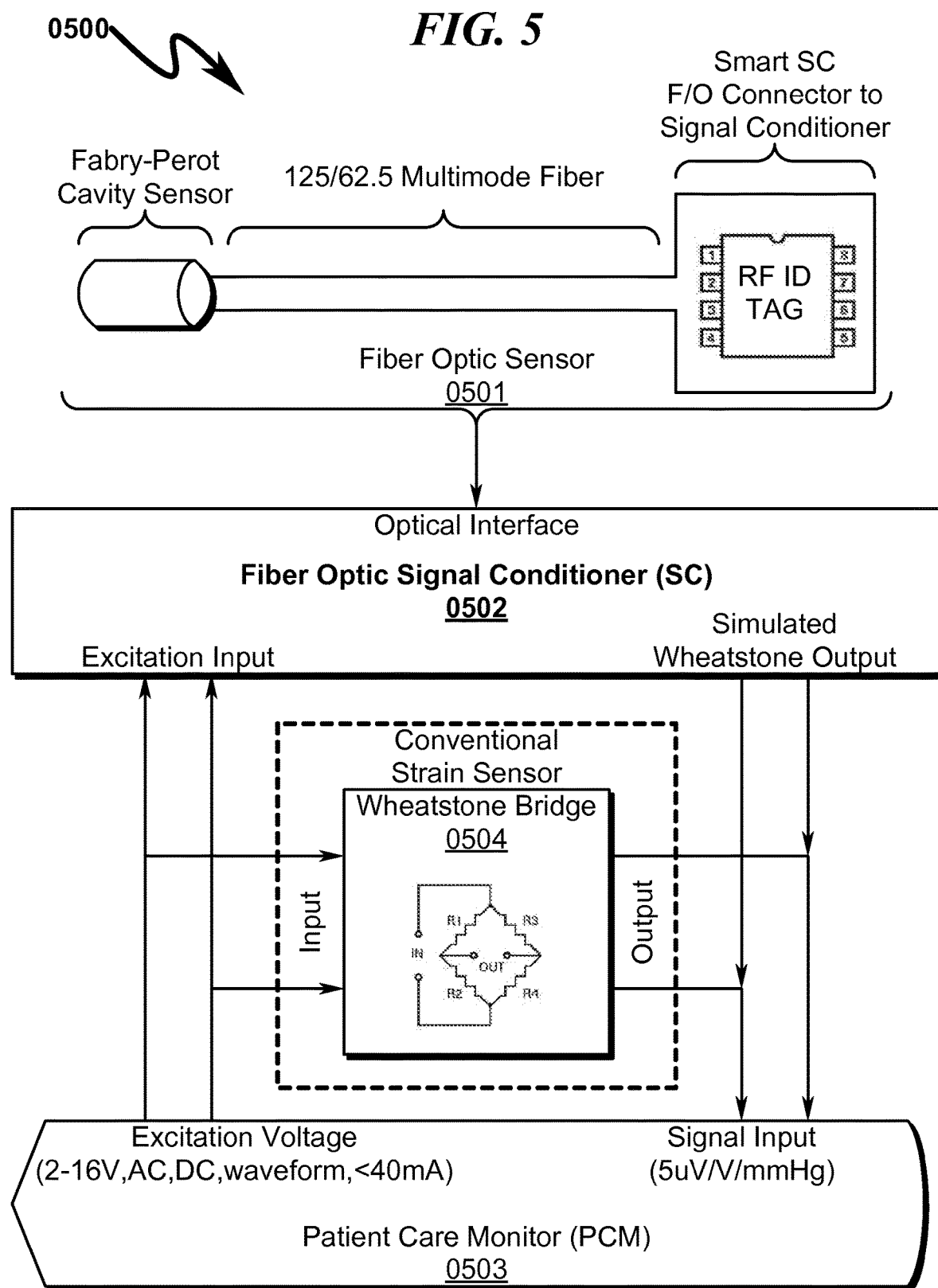
FIG. 5 illustrates an exemplary PCM interface embodiment utilizing teachings of the present invention.

FIG. 5 (0500) depicts the basic components of a blood pressure monitoring system which the present invention makes compatible with conventional PCMs.

FIG. 5 (0500) schematically shows the basic components of a fiber optic pressure sensor assembly (0501). It consists primarily of three parts. One part is a Fabry-Perot (F-P) pressure sensitive diaphragm mounted at the distal end of a cavity which is the transducer itself. Pressure induced deflections of this diaphragm modulate light shining on it and reflect the light down the fiber optic cable which is the second part. The third part is a fiber optic connector that connects to a signal conditioner (0502) and contains a non-volatile memory holding sensor specific gauge factors.

The Fiber Optic Signal Conditioner (0502) detailed in FIG. 5 (0500) represents a schematic block diagram of one instantiation of an electro-optic signal conditioning device that excites a fiber optic Fabry-Perot pressure sensor and processes the reflected light into an electrical signal proportional to the physiological pressure on the sensor. The optical interferometer combines the excitation light and the reflected signal light to produce an optically modulated signal that indicates the pressure-induced deformation of the F-P sensor cavity. This optically modulated signal is detected using photodetectors (or alternatively detected by a CCD imaging array) and converted to an electrical signal that is stored in a digital memory used for subsequent processing. The microprocessor processes the digital pressure data and converts it to a format compatible with a serial digital output and/or supplies the data to a digital-to-analog converter that produces an analog signal output. A power electronics subsystem (not shown) converts a single power input into multiple voltages needed by the various components in the signal conditioner.

The bottom of FIG. 5 (0500) shows the main parts of a conventional IBP patient care monitor (PCM) (0503) and a Wheatstone Bridge resistive pressure sensor (0504). The bridge is excited by a voltage from the patient care monitor (PCM) as shown. The sensor elements change their resistances based on the strain (pressure) on them. These changes in the resistance values unbalance the bridge and produce a voltage proportional to the excitation voltage and the pressure. The fiber optic signal conditioner (0502) substitutes the fiber optic sensor (0501) for the conventional strain sensor (0504) used by the PCM (0503).

Figure 6:
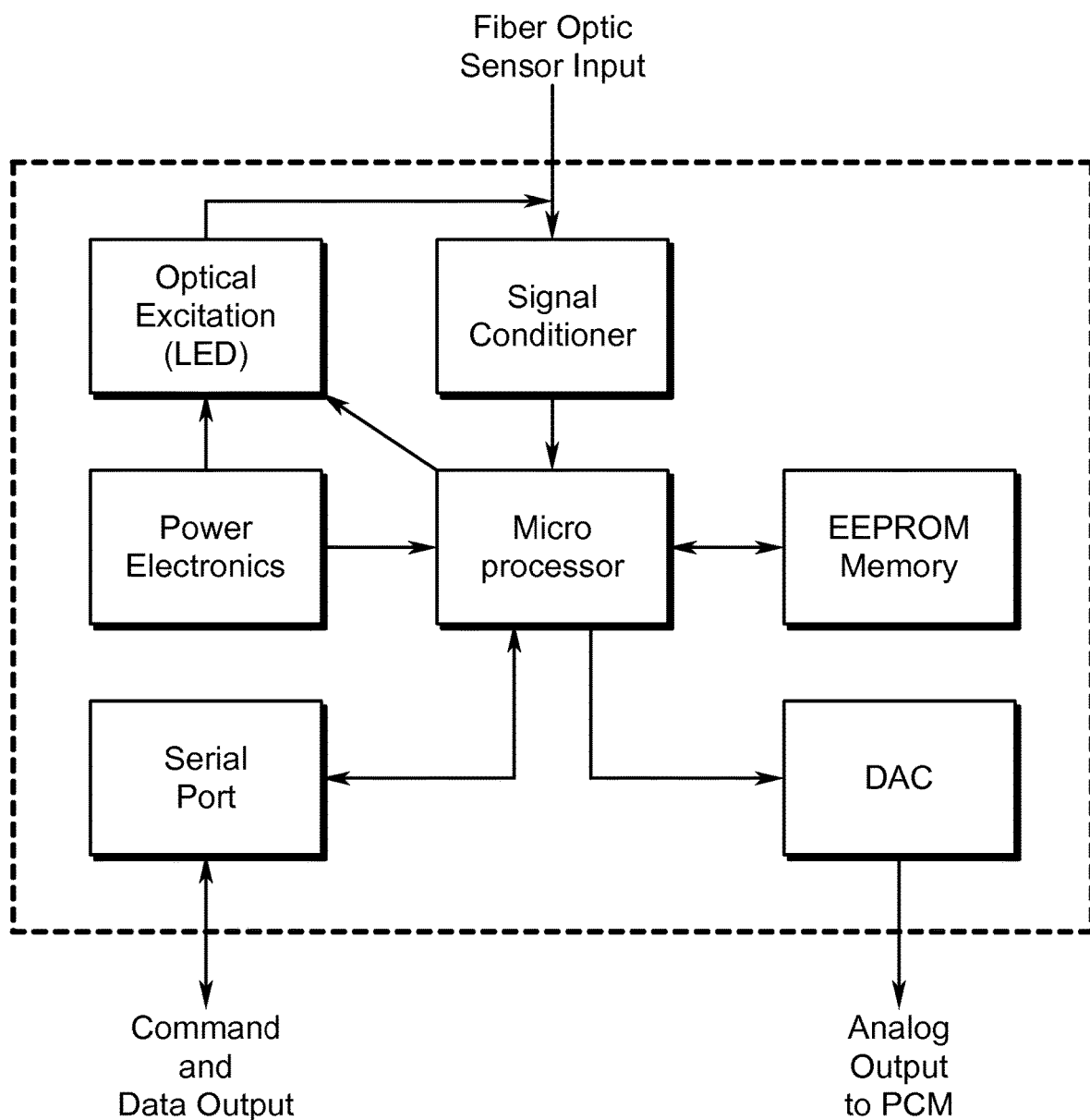
FIG. 6 illustrates exemplary internal logic interface detail of a present invention embodiment that interfaces between a fiber optic pressure sensor, a PCM, and an auxiliary command/data processor.

FIG. 6 (0600) depicts a schematic block diagram of the major components of the present invention including the signal conditioner (0502) previously shown in FIG. 5 (0500) and the conventional patient care monitor (PCM) shown earlier in FIG. 5 (0500). However the Wheatstone Bridge is now replaced by a connection to the fiber optic interface.

Major functions and internal architecture of the present invention (interface) are schematically shown in the large central block. One or more of the outputs of the fiber optic signal conditioner is connected to the interface electronically. Both commands and pressure data travel over the digital connection, where only the pressure information is present on the analog connection. If needed this analog signal is converted to a digital signal by an analog-to-digital converter (ADC) and stored in random access memory (RAM) by the microprocessor for subsequent processing. The digital communications interface block converts the data using the appropriate communications protocol and the data is stored in RAM memory.

The microprocessor is the central processing element in the system and provides the ability to support many other functions than just processing blood pressure data. The microprocessor executes instructions stored in the firmware EEPROM that manage and process functions such as diagnostics, error handling, normal operation, alarms, etc. The input communications interface sends control commands to the fiber optic signal conditioner as directed by the microprocessor. Another major task of the microprocessor is to control the function of emulating a conventional non-fiber optic pressure sensor. This is accomplished through continuously reading the particular IBP excitation voltage present at the patient care monitor (PCM) and conditioning the pressure data to be proportional to it as the monitor expects. The microprocessor processes the data stream and sends it to a digital-to-analog converter (DAC) after which it is scaled to the appropriate values for direct output to the patient care monitor (PCM). During this conversion the microprocessor applies a previously selected sensitivity factor (typically either 5-microvolts/volt/mmHg or 40-microvolts/volt/mmHg)) appropriate to the patient care monitor (PCM) that is connected to the interface monitor output. This emulation ability provides compatibility with conventional patient care monitors (PCMs).

The firmware EEPROM is externally accessible through a second digital communications interface by other computer applications for updating the firmware. This second digital communications interface supports multiple communications protocols. The microprocessor also manages the human interface devices local to the interface. These devices may comprise switches, visual and/or aural indicators, and/or an alphanumeric blood pressure display.

As detailed in subsequent FIGURES, this pressure measurement interface may be powered by either a battery or by a power adapter that converts utility AC power to a DC voltage for the interface. An internal power converted breaks down the main DC power source into multiple DC power voltages used by various components in the interface.

Intelligent Patient Monitor Interface (0700, 0800)

Figure 7:
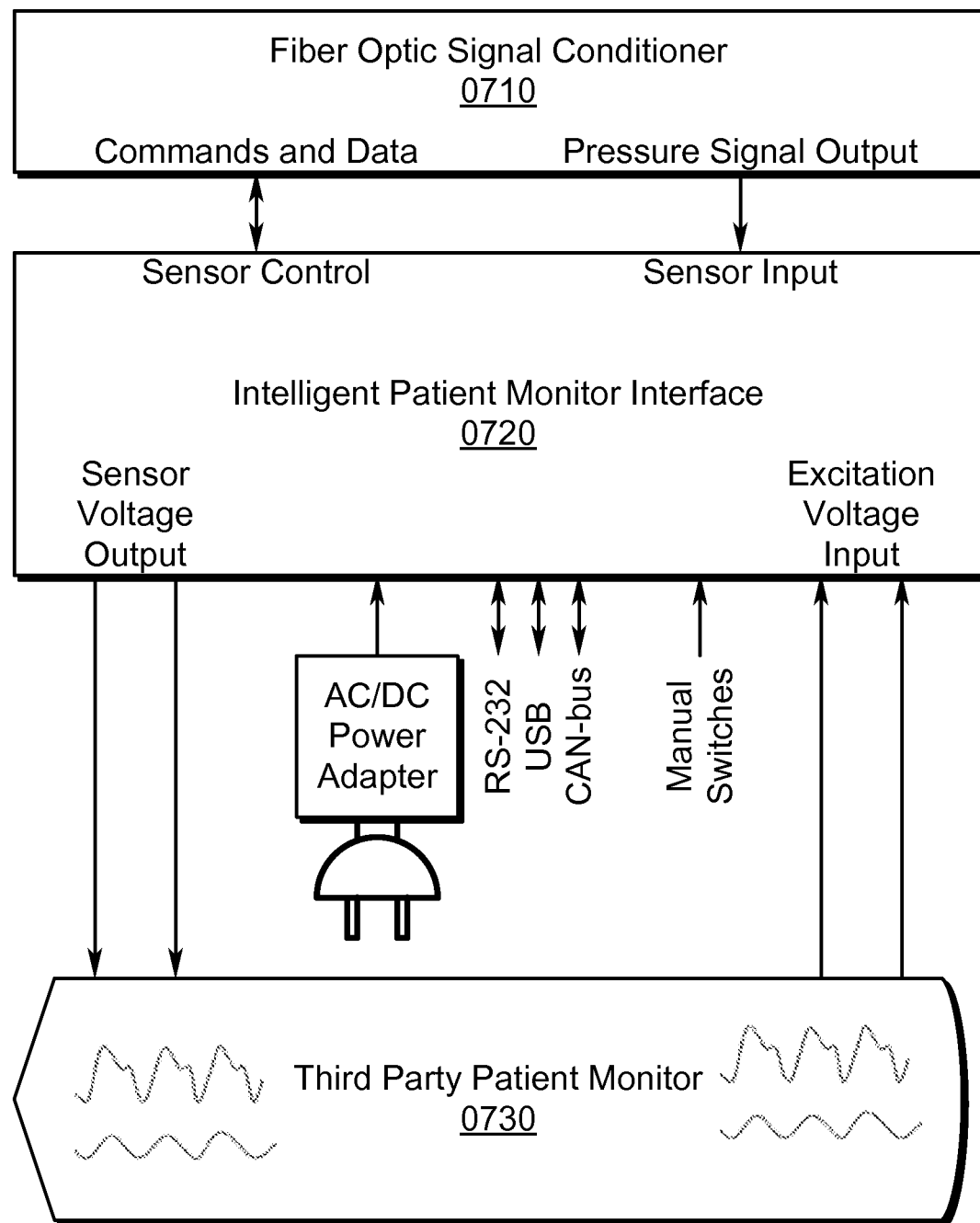
FIG. 7 illustrates a preferred exemplary embodiment of the present invention as applied to an intelligent patient care monitor (PCM) interface.

A preferred embodiment of the present invention applied to a generic pressure sensing application is depicted in FIG. 7 (0700), wherein a fiber optic signal conditioner (0710) interfaces with a fiber optic pressure sensor to generate output signaling based on measured pressure in response to commands and/or data received from an intelligent patient monitor interface (IPMI) (0720). The IPMI acts as the "bridge" between the fiber optic pressure sensor interface (0710) and a third party patient care monitor (PCM) (0730) configured to accept Wheatstone Bridge compatible pressure sensors. Within this context excitation voltages generated by the PCM (0730) are used by the IPMI (0720) to scale/reference the sensor voltage outputs used to driver the Wheatstone Bridge inputs of the PCM (0730).

Figure 8:
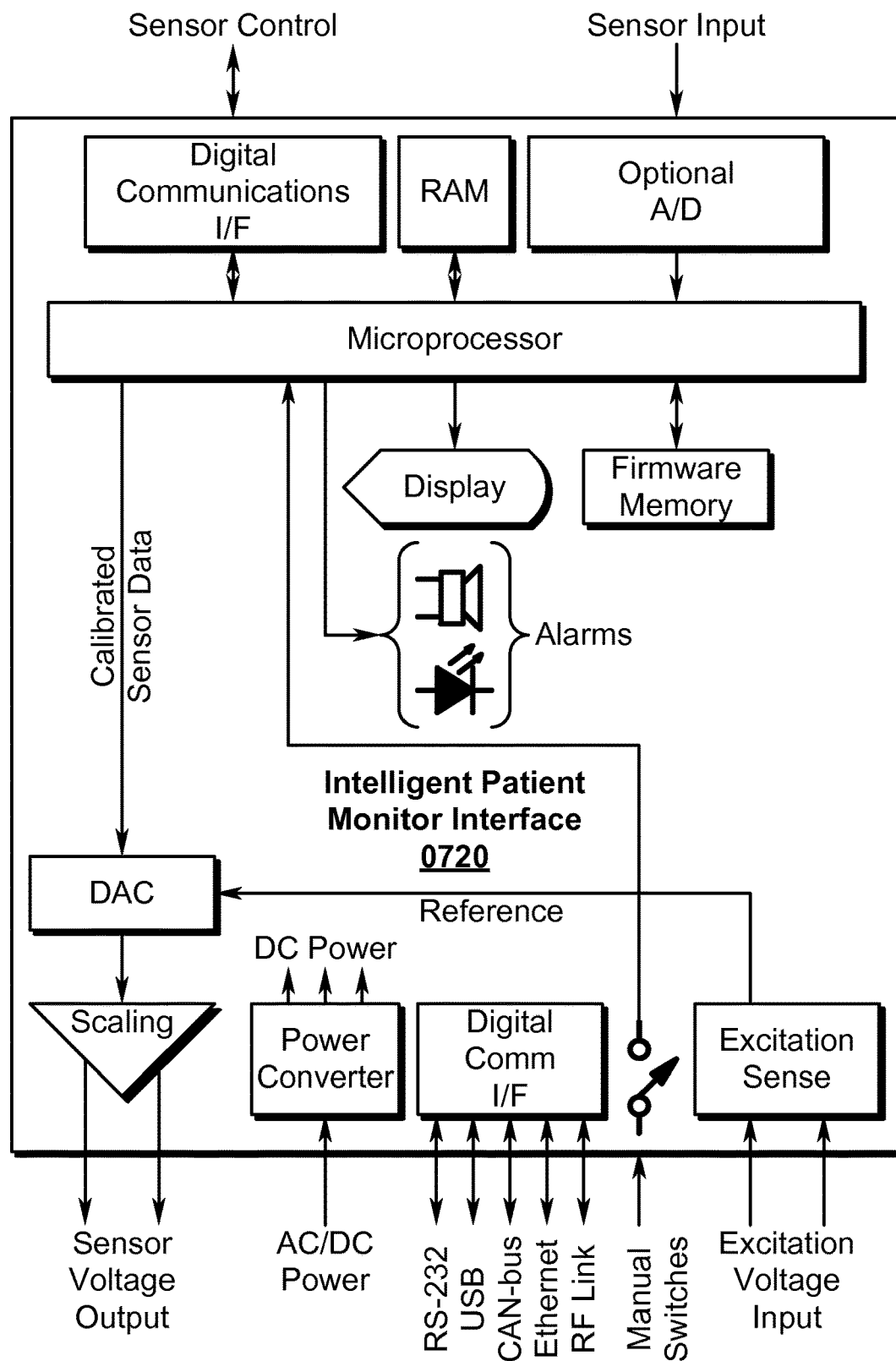
FIG. 8 illustrates a preferred exemplary embodiment of the present invention as detailing the internals of an intelligent patient care monitor (PCM) interface.

More detail of the IPMI in this context can be observed in FIG. 8 (0800) wherein the internals of the IPMI (0720) generally comprise a microprocessor, RAM, digital communications interfaces, optional A/D converter, display, firmware program memory, human interface alarms, excitation sensing and sensor output voltage generation circuitry, as well as power conversion circuitry and provisions for digital communication to other processors.

Exemplary Wheatstone Bridge Interface (0900, 1000)

Figure 9:
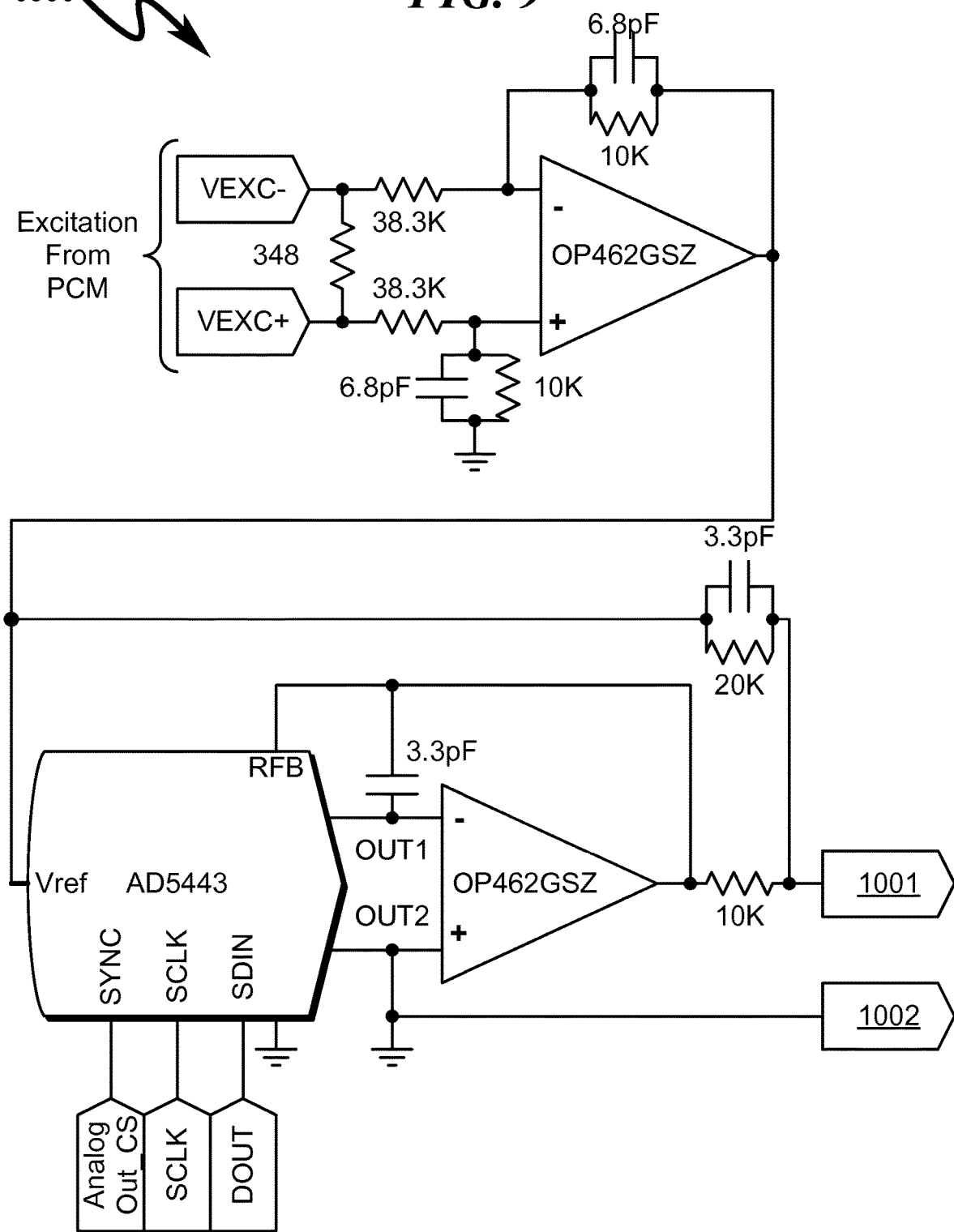
FIG. 9 illustrates an exemplary Wheatstone Bridge interface circuit schematic useful in some preferred embodiments of the present invention.
Figure 10:
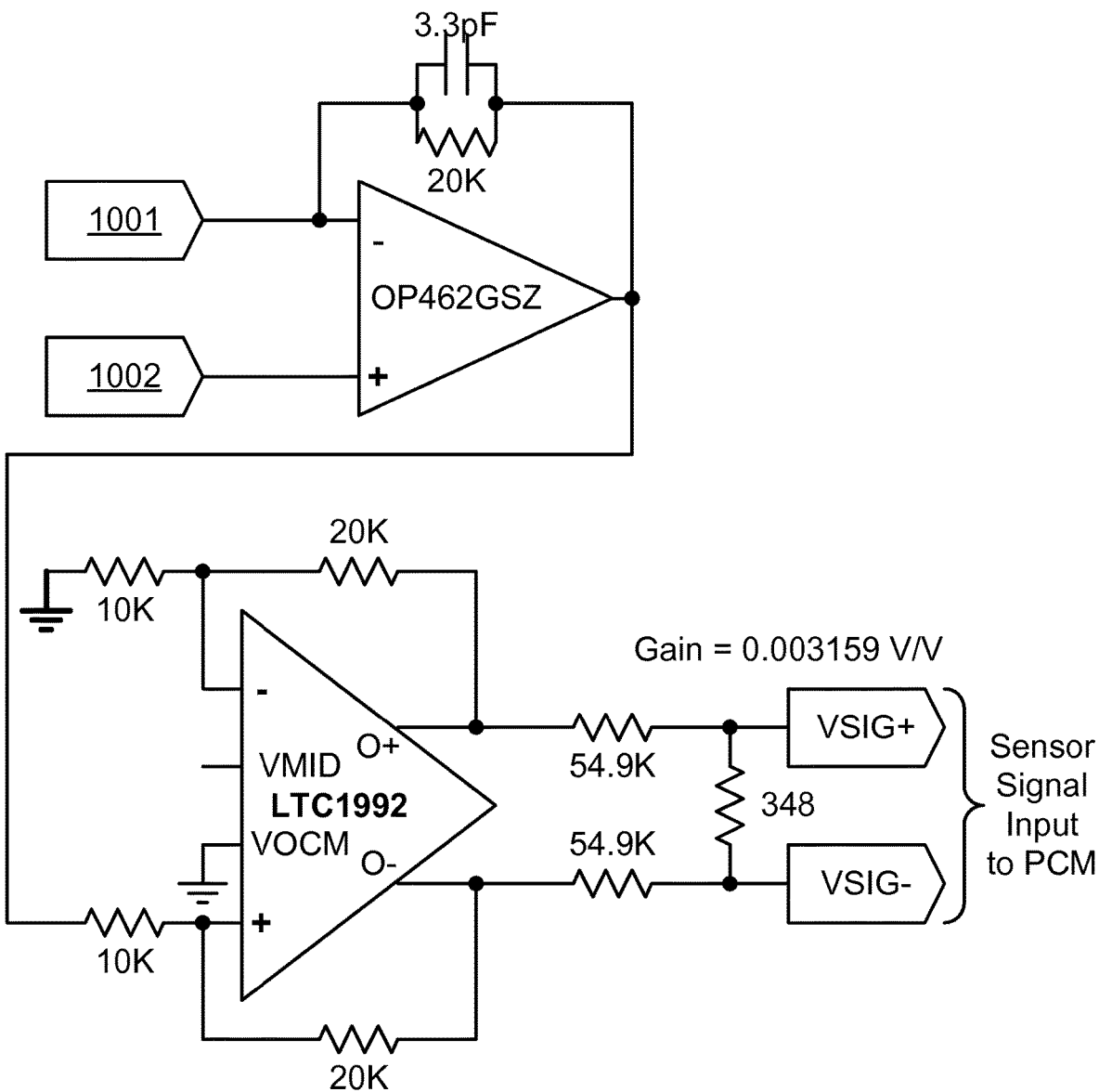
FIG. 10 illustrates an exemplary Wheatstone Bridge interface circuit schematic useful in some preferred embodiments of the present invention.

While the present invention may be embodied in many forms, several preferred exemplary embodiments may make use of a Wheatstone Bridge interface having bridge excitation inputs and simulated bridge sense outputs as generally illustrated in FIG. 9 (0900) and FIG. 10 (1000). One skilled in the art will recognize that the functionality depicted in FIG. 9 (0900) and FIG. 10 (1000) may be embodied in a wide variety of forms, including some configurations in which this circuitry is embodied in an integrated microcontroller unit (MCU) and/or application specific integrated circuit (ASIC).

Advantages to Present Invention Architecture

Although fiber optic IBP measuring systems exist, most are targeted at laboratory animal research or are systems that are used for measuring pressure in other body fluids such as cerebrospinal fluid. The present invention uniquely enables the use of modern fiber optic pressure transducer measurements to be interpreted and displayed directly on the device or on an unmodified conventional patient care monitor (PCM). This creates a "plug and play" capability where a fiber optic sensor device can be transparently substituted for a standard Wheatstone Bridge fluidic sensor without adjustments or modifications to the patient care monitor (PCM). Alternatively it can be used in a standalone mode where no connection to other equipment is necessary to measure systolic and diastolic blood pressure values in real-time.

Another unique aspect of the present invention is the inherent flexibility to adapt to different application requirements. The present invention is specifically designed to accommodate new functionality without significant hardware modifications through software updates. Another differentiating feature of the present invention is the ability to combine the data from multiple sensors and distribute the data individually to separate arbitrary downstream instruments and/or analysis computers, or alternatively distribute selected multi-sensor data streams into partially or wholly aggregated data streams among multiple outputs.

The present invention is optimally implemented using an electro-optical signal conditioner coupled with modern digital electronics to support control, data acquisition, and other functions described herein. The design is based on an embedded programmable microprocessor that executes firmware instructions originating from on-board non-volatile EEPROM memory as generally illustrated in FIG. 6 (0600). This memory is externally accessible from a computer for downloading firmware, debugging, maintenance, control, and diagnostic functions. During normal operation there is no need for an external computer connection and the processor executes embedded firmware instructions that perform only the functions necessary for the clinical application. A separate RAM memory is used for various system functions as well as data processing.

Multiple communications ports may be available for transferring digital commands and data to and from the present invention. A communications port supports one or more standard serial communications such as RS-232 or USB or CAN-bus connectivity. An analog patient care monitor (PCM) data output port emulates a fluidic IBP transducer and supplies analog data to patient care monitor (PCM) that is indistinguishable from a fluidic blood pressure sensor. Communications ports are accessed selectively based on the application via the on-board patient care monitor (PCM) interface, a software application running on an external computer, or by manual means. These connections also support integrating the present invention with other electronic clinical instrumentation.

The present invention also incorporates the ability to access, modify, and create new functionality with little or no hardware modification by only downloading new firmware and/or configuring jumpers. Examples of the value of this enhancement capability include:

easy maintenance and updates (including diagnostic and event logging, version tracking, and performance monitoring);

real-time data analysis (including physiological data analytics, threshold monitoring, alarming, and data quality assurance);

adaptive device configurability (including user-specific configurations such as procedure-specific or physician-specific thresholds and changing the sensor emulation sensitivity).

The present invention may automatically read, identify and configure itself to adapt to the unique characteristics of each fiber optic transducer as well as provide a go/no-go indication of the integrity of the sensor readiness. It may incorporate internal system health status diagnostics and will activate an indicator when the device is unfit for use. Parameters associated with any failure of a diagnostic may be internally logged for either immediate display or maintenance access.

Clinical blood pressure measurements today are typically derived from either:

an external blood pressure cuff;

a fluidic blood pressure transducer connected to an indwelling access port; or an external pressure sensor transducer mounted on an IV pole that connects to a catheter that is inserted into an artery, referred to as an arterial line, or typically referred to as an "ART" line.

These measurement methods vary significantly in their accuracy, ease of use, and timeliness of the readings. These variations are primarily due to being based on inferior pneumatic or hydraulic sensor systems, and mechanical interference between the pressure transducer carrier and other clinical devices introduced into the patient through the same entry site.

The ability to use a highly accurate fiber optic transducer with a high sampling rate and low drift that alleviates many drawbacks of conventional measurement techniques with standard patient care monitors (PCMs) is very attractive.

The present invention enables the use of fiber optic IBP monitoring and all its previously stated differentiators, advantages, and benefits, without requiring hospitals and other care delivery venues to invest in wholly new display technologies.

Besides the benefits of overcoming the problems stated previously, the following are additional advantages of the present invention:

Self-contained, small, light, and portable.

Superior drift, fidelity and accuracy characteristics.

Automatic zeroing function.

Supports EMI immune fiber optic blood pressure sensors.

Adaptable to digital computer interfaces as well as a variety of conventional patient care monitors (PCMs).

Self-diagnostic mode.

Customizable for specific people and/or clinical situations.

Low power requirements.

Automatic calibration to specific fiber optic sensor characteristics.

Adapts to patient care monitors (PCMs) that support different sensitivity factors.

Prior art pressure detection systems do not use fiber optic cable as the primary pressure sensing element.

The use of fiber optic pressure sensors by the present invention permits BPM systems using this technology to be used within an MRI environment, something not possible with wired BPM systems.

The use of fiber optic pressure sensors by the present invention permits the BPM system to take 1000 measurements per second as compared to approximately 50 per second with the prior art.

The present invention permits high precision raw BPM data to be collected for a given patient and then analyzed offline.

The present invention has no electrically conductive invasive patient wires, and therefore is immune to electromagnetic fields and interference (especially power line 50/60 Hz interference) that may be proximal to the patient environment.

The present invention permits near unity ratios of systolic/diastolic pressure ratios to be measured, a feature not possible using the prior art. This feature is especially important at low heart rates, a condition not well handled by prior art BPM systems. It should be noted that near-unity pressure ratios in conjunction with low heart rates are commonly encountered when diagnosing infants and premature babies.

The ability to take spatially disparate blood pressure readings to allow for differential analysis (especially when the differentials measured are small) is possible using the present invention but not available using prior art BPM technologies.

The ability to measure intracranial pressure and venous pressures.

The ability to integrate a pressure sensor and associated structure (catheter, etc.) into an implanted BPM system that is implanted into a patient with data extraction from this device occurring wirelessly.

The ability to calibrate a given pressure sensor to current ambient atmospheric pressure under a variety of patient application conditions. A differentiator available in the present invention is the BPM ability to determine whether a PSS has been zeroed before and act accordingly. This is important in the case when a PSS is unintentionally disconnected and reconnected to a BPM without the ability to achieve a re-zero. The inability to re-zero is the case when a PSS is still inserted in a live patient where the PSS is not exposed to ambient atmospheric pressure. The BPM warns the operator when this happens because, in extreme cases where the disconnection is long enough for ambient pressure to change from the original zero pressure, the operator should be notified. Also, because it detects a pre-zero, the lack of a notification assures the operator that a newly connected PSS will be zeroed with current ambient pressure. This function is incorporated in the logic diagrams, but is not described anywhere else.

While this list is not limitive of the present invention scope, it does provide some insight into the many potential embodiments of the present invention and their possible applications.

Exemplary Application Contexts

The present invention may have many applications, some of the preferred contexts including the following:

Today IBP measurements are mostly isolated to use in procedures requiring general anesthesia. Otherwise typically a pneumatic blood pressure cuff is used in spite of its associated intrinsic and patient condition related inaccuracies. The present invention allows use of high accuracy, real time, fiber optic-based sensor monitoring in a much wider variety of critical care situations.

There is no known signal connection capability between a fiber optic physiological blood pressure sensor and a conventional IBP monitor input. This function of the present invention overcomes the need to redesign the IBP inputs of the tens of thousands of existing patient care monitors (PCMs) to use fiber optic-based IBP sensors. Also it is the prerequisite for solutions to many other problems including those stated below. In concert with a disposable fiber optic blood pressure sensor, it enables significant clinical and operational benefits that have been needed for decades.

There is no fiber optic IBP sensor that can interface to a variety of patient care monitors (PCMs). The present invention overcomes this problem by automatically adapting to each different patient care monitor (PCM) input characteristics.

There is not a clinically adopted IBP monitor/sensor combination today that exhibits the real time accuracy available from fiber optic sensors. Critical care health professionals need a more timely and accurate method of blood pressure monitoring. Real time blood pressure data and accuracy are very important for diagnosis, treatment and subsequent critical care monitoring. Fiber optic sensors enabled through the present invention accomplish this functionality.

There is no known IBP monitor capable of indicating and assuring the integrity of a fiber optic sensor-to-monitor connection. Confidence in the proper operation of the device is essential to its use in clinical medicine.

There is no known fiber optic-based IBP monitor that has the ability to be upgraded and diagnosed in the field. This helps to lower the cost of maintenance.

There is no known fiber optic-based IBP monitor that has the ability to do standalone real time signal data processing and display of patient systolic and diastolic blood pressure. A self-contained fiber optic blood pressure monitor that is not dependent on other clinical instrumentation is highly desired by clinical professionals.

The present invention enables the use of fiber optic IBP monitoring and all its previously stated differentiators, advantages, and benefits, without requiring hospitals and other care delivery venues to invest in wholly new monitoring and display technologies. This capability retains the usefulness of a facilities' inventory of conventional IBP monitors thus decreasing the cost of improved care markedly.

One skilled in the art will no doubt be able to apply the teachings of the present invention to a wide variety of application contexts not specifically detailed above.

Additional Analysis Capabilities

It should be noted that in some preferred application contexts, the use of the present invention as applied to fiber optic blood pressure monitor (BPM) systems results in significantly improved accuracy with respect to detection of correct systolic/diastolic pressures, especially at low heart rates. Traditional PCMs have significant difficulty in analyzing systolic/diastolic pressure readings when the systolic/diastolic pressure ratios approach unity. Additionally, as the heart rate is decreased from a nominal 70 beats per minute (BPM) to say 10-30 BPM, traditional PCMs have difficulty in tracking the correct systolic/diastolic pressures and often register "no pressure" or similar error messages indicating no discernible blood pressure. The present invention when integrated with fiber optic pressure sensors permits a much wider dynamic range of pressure readings to be recorded and as a result can accurately detect very low blood pressure readings and systolic/diastolic pressure ratios even with heart rates as low at 10 BPM.

This capability is important in many situations where the patient is on the border of death or severely impaired. Such might be the case for a neonatal care patient or a trauma patient that has suffered a severe injury or cardiac event. In these situations the ability for the health care professional to discern small variations in systolic/diastolic pressures and to be able to do so at very low heart rates is critical to the ability of the health care professional to provide proper treatment to the patient to restore full cardiac and blood pressure functionality. The present invention, by providing this new BPM capability, drastically extends the capabilities of conventional PCMs to address this critical patient monitoring requirement.

Preferred Embodiment System Summary

The present invention preferred exemplary system embodiment anticipates a wide variety of variations in the basic theme of construction, but can be generalized as a transducer interface system comprising:
  (a) computing device;
  (b) analog sensor A/D converter;
  (c) bridge excitation converter; and
  (d) bridge sense D/A converter;
  wherein
  the analog sensor A/D converter samples an analog signal from an analog sensor and converts the analog signal to a digital sensor value;
  the analog sensor is associated with calibration factors that comprises data used to normalize the analog signal from the analog sensor;
  the computing device applies the calibration factors to the digital sensor value to produce a digital compensated sensor value;

the bridge excitation converter receives an analog Wheatstone Bridge excitation signal and converts the analog Wheatstone Bridge excitation signal to produce a bridge excitation value;

the bridge sense D/A converter receives the digital compensated sensor value and generates an analog compensated sensor value; and the analog compensated sensor value is scaled by the bridge excitation value and normalized to a standardized pressure level to produce a converted analog Wheatstone Bridge sense signal.

This general system summary may be augmented by the various elements described herein to produce a wide variety of invention embodiments consistent with this overall design description.

Preferred Embodiment Method Summary

The present invention preferred exemplary method embodiment anticipates a wide variety of variations in the basic theme of implementation, but can be generalized as a transducer interface method comprising:
(1) sampling an output signal from an analog sensor using an A/D converter to produce a digital sensor output value;
(2) applying calibration factors to the digital sensor output value using a computing device to produce a digital sensor compensated value;
(3) sensing a Wheatstone Bridge excitation voltage signal to form a bridge excitation value;
(4) converting the digital sensor compensated value from digital to analog using a D/A converter to produce an analog sensor compensated value; and
(5) scaling the analog sensor compensated value by the bridge excitation value to produce a converted Wheatstone Bridge sense signal.

One skilled in the art will recognize that these method steps may be augmented or rearranged without limiting the teachings of the present invention.

System/Method Variations

The present invention anticipates a wide variety of variations in the basic theme of construction. The examples presented previously do not represent the entire scope of possible usages. They are meant to cite a few of the almost limitless possibilities.

This basic system and method may be augmented with a variety of ancillary embodiments, including but not limited to:

An embodiment wherein the analog sensor comprises a fiber optic pressure sensor.

An embodiment wherein the analog sensor comprises a Fabry-Perot pressure sensor.

An embodiment wherein the analog sensor comprises a Fabry-Perot pressure sensor located within a medical device.

An embodiment wherein the analog sensor comprises a Fabry-Perot pressure sensor positioned at the distal end of a medical device, the medical device selected from a group consisting of a catheter, catheter incorporating a mounted balloon, vascular sheath, ventriculostomy catheter, ventricular shunt catheter, lumbar drain, and intracranial pressure monitor structure.

An embodiment wherein the analog sensor comprises a Fabry-Perot pressure sensor positioned proximal to the distal end of a medical device, the medical device selected from a group consisting of a catheter, catheter incorporating a mounted balloon, vascular sheath, ventriculostomy catheter, ventricular shunt catheter, lumbar drain, and intracranial pressure monitor structure.

An embodiment wherein the analog sensor comprises a plethora of Fabry-Perot pressure sensors located within a medical device, the medical device selected from a group consisting of a catheter, catheter incorporating a mounted balloon, vascular sheath, ventriculostomy catheter, ventricular shunt catheter, lumbar drain, and intracranial pressure monitor structure.

An embodiment wherein the analog sensor is an invasive arterial blood pressure (IBP) sensor.

An embodiment wherein the analog Wheatstone Bridge excitation signal is generated by a patient care monitor (PCM).

An embodiment wherein the converted analog Wheatstone Bridge sense signal is displayed using a patient care monitor (PCM).

An embodiment wherein the calibration factors are interpolated before application to the digital sensor value.

An embodiment wherein the analog sensor further comprises a non-volatile memory in which the calibration factors are stored.

An embodiment wherein the analog sensor further comprises a RFID TAG memory in which the calibration factors are stored.

An embodiment wherein the analog sensor is zero calibrated to atmospheric pressure.

An embodiment wherein the digital bridge sense value is transmitted to a display device that indicates systolic blood pressure, diastolic blood pressure, mean blood pressure, and/or heart rate values.

An embodiment wherein the system further comprises a visual status indicator, the visual status indicator displaying a pressure value that is selected from a plethora of the digital compensated sensor values within a sampling period.

An embodiment wherein the system further comprises a visual status indicator, the visual status indicator displaying a pressure value that is computed from an analysis of a plethora of the digital compensated sensor values within a sampling period.

An embodiment wherein the system further comprises a visual status indicator, the visual status indicator displaying a pressure value that is computed from a periodic analysis of a plethora of the digital compensated sensor values within a sampling period.

An embodiment wherein the system further comprises a visual status indicator, the visual status indicator displaying a peak pressure value that is computed from an analysis of a plethora of the digital compensated sensor values within a sampling period.

An embodiment wherein the system further comprises a visual status indicator, the visual status indicator displaying a mean pressure value that is computed from an analysis of a plethora of the digital compensated sensor values within a sampling period.

An embodiment wherein the system further comprises a visual status indicator, said visual status indicator displaying systolic blood pressure, diastolic blood pressure, mean blood pressure, and/or heart rate values that are computed from an analysis of a plethora of the digital compensated sensor values.

An embodiment wherein the digital compensated sensor value is streamed via a hardwired serial interface to a remote computer system for analysis of the digital sensor value derived from the analog sensor.

An embodiment wherein the digital compensated sensor value is streamed via a wireless serial interface to a remote computer system for analysis of the digital sensor value derived from the analog sensor.

An embodiment wherein: the analog sensor A/D converter is replicated to permit multichannel input data collection from a plethora of analog sensors; and the computing device comprises multiple digital inputs to enable input processing of data received from the replicated analog sensor A/D converter.

An embodiment wherein: the analog sensor A/D converter is replicated to permit multichannel input data collection from a plethora of analog sensors; the bridge excitation converter and the bridge sense D/A converter are replicated and/or multiplexed to permit multichannel data collection; the computing device comprises multiple digital inputs to enable input processing of data received from the replicated analog sensor A/D converter; the computing device comprises multiple digital inputs to enable input processing of data received from the replicated bridge excitation converter; and the computing device comprises multiple digital outputs to enable output processing of data to the replicated bridge sense D/A converter.

One skilled in the art will recognize that other embodiments are possible based on combinations of elements taught within the above invention description.

Exemplary Embodiment Logic Flow

While the present invention may incorporate a wide variety of implementations, some embodiment configurations incorporate preferred program logic. Within this context, the following discussion details one preferred logic flow for an exemplary BPM implementation.

Terminology

The following provides important information about the exemplary BPM logic diagram views which are discussed below in more detail.

The exemplary logic diagrams are intended to describe the general operational concepts (not necessarily the exact design or implementation) that may be incorporated into the BPM. It is also intended to provide an informal, but more explicit, basis for discussions of BPM functionality as described in the BPM PRD detailed subsequently in this document. The diagram is expected to be modified as needed to reflect the current approach as changes are made. The diagrams explicitly do not include any timeouts for infinite loop conditions or other timing related functions.

Terminology Definitions

The following definitions are operative within this discussion:
BP Blood pressure
COUNT EEPROM Write Zero value counter
EEPROM Electronic storage device that is part of the PSS
Enable Allows a function, but does not activate the function
Disable Inhibits a function from being activated
LED Visible front panel alarm light indicating that an average blood pressure has been sensed that is below a pre-set threshold
PAT Current ambient atmospheric pressure at the BPM
MAP Mean Arterial Pressure
DMAP Displayed MAP value calculated from the current frame
$DMAP_N$ Current frame Display MAP value stored in the BPM
$DMAP_{N-1}$ Stored DMAP value from previous Display frame
AMAP Alarm MAP value calculated from two display frame values
$P_D$ Current diastolic blood pressure value stored in the BPM
$P_L$ Low blood pressure alarm threshold
$P_{MAX}$ Maximum possible full-scale pressure value (all 1's)
$N_{MAX}$ Maximum possible full-scale zero value (all 1's)
$P_s$ Current systolic blood pressure value stored in the BPM
$P_{ss}$ $P_{AT}$ compensated PSS pressure value
$P_v$ Fully compensated blood pressure value
PSS Pressure Sensing Sheath
Set Activate a function
Reset Deactivate a function Assumptions The following are assumptions made in regards to the logic flow diagrams discussed below:
PSS EEPROM stores: calibration factors and their checksum, and zero factor(s).
PSS EEPROM checksum and calibration factors are calibrated and set at the factory.
Factory will set EEPROM Zero factor to $N_{MAX}$ (all 1's) for all sensors before shipment.
Zero factor is stored in the PSS EEPROM by the BPM after zeroing.
After initialization, alarms are triggered or reset from the results of each 4-second frame.

Blood Pressure Monitor Main Process Method (1100)-(2400)

Figure 11:
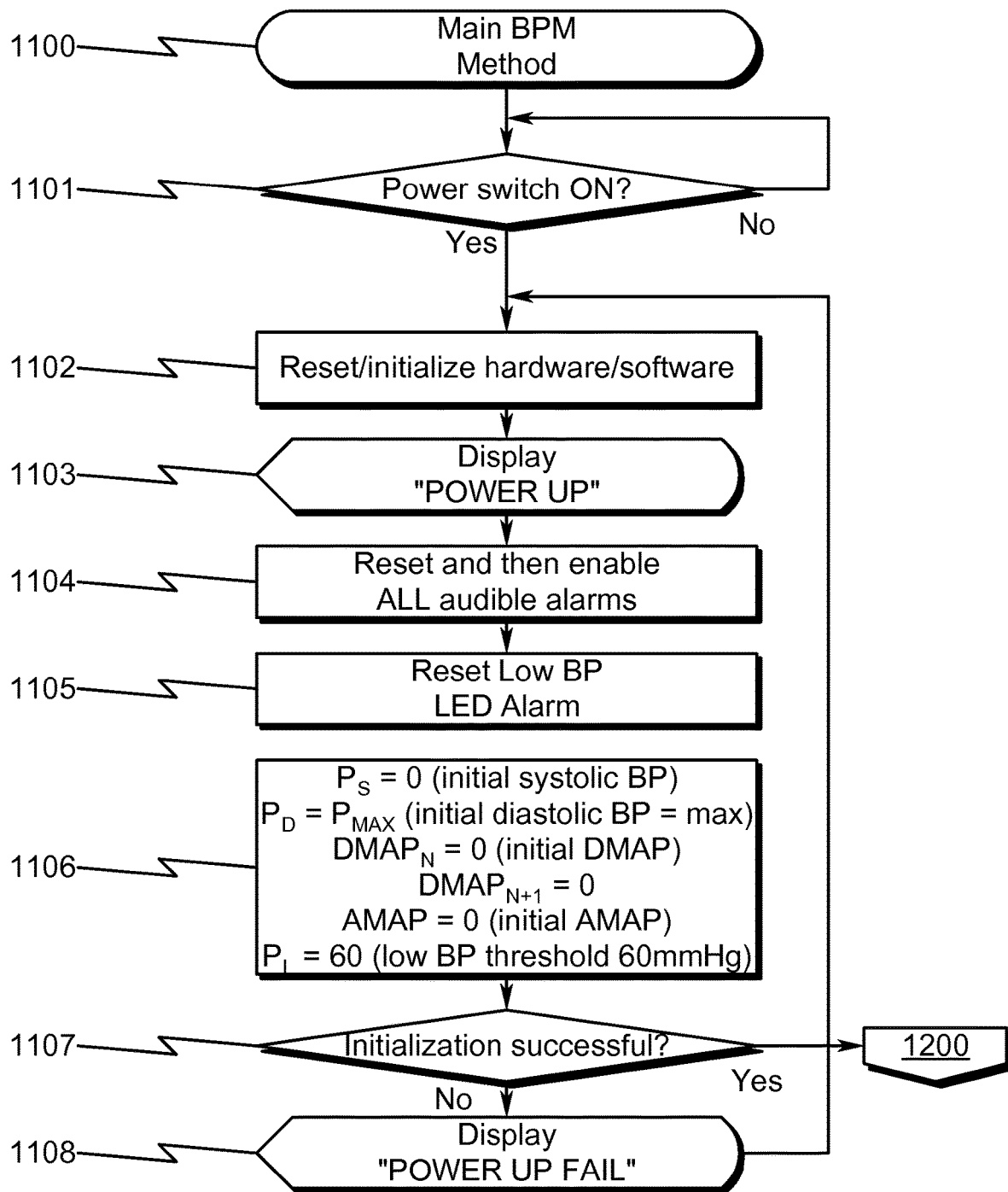
FIG. 11 illustrates an exemplary main process flowchart implementing a BPM incorporating the teachings of the present invention.
Figure 12:
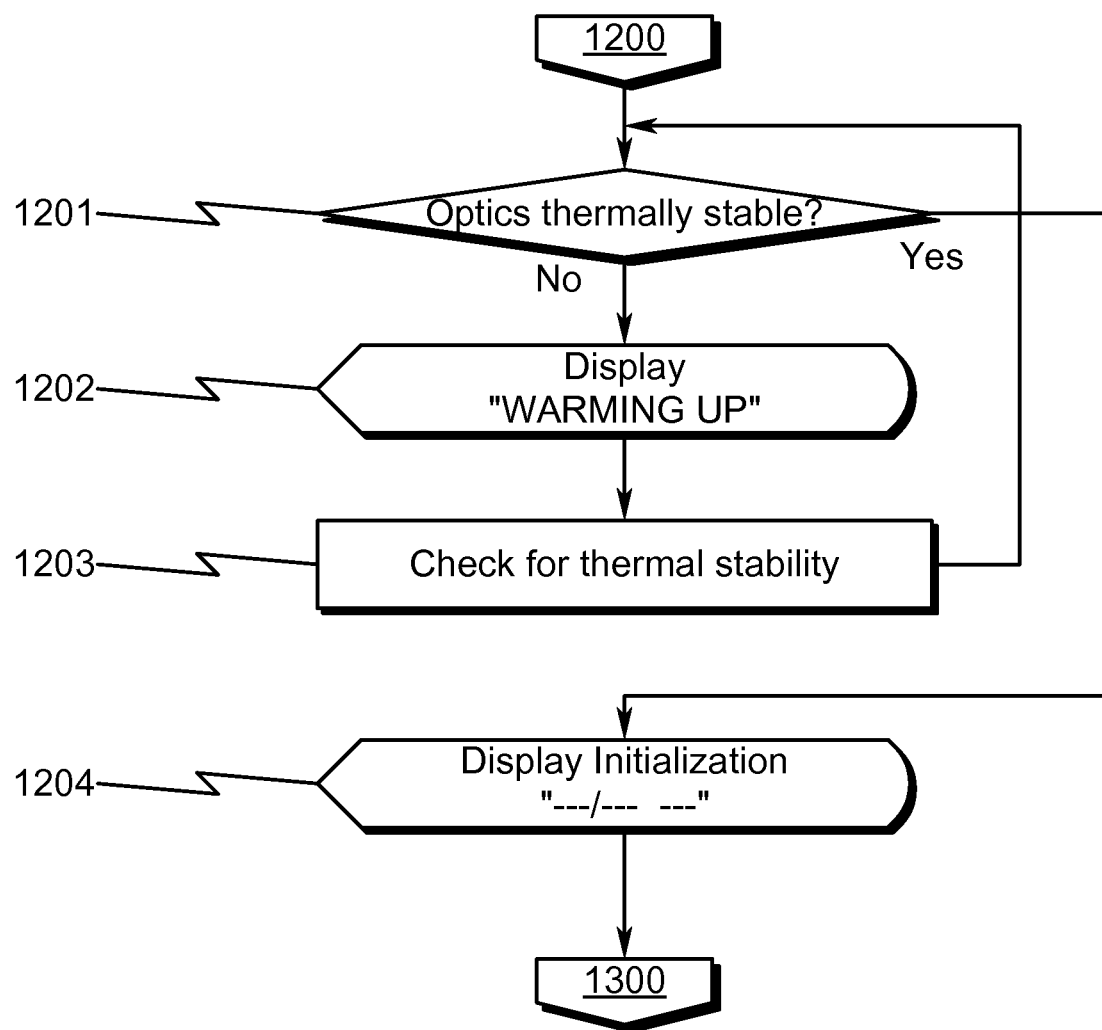
FIG. 12 illustrates an exemplary sub-process detail flowchart implementing sub-functions of the main BPM flowchart that incorporate the teachings of the present invention.
Figure 13:
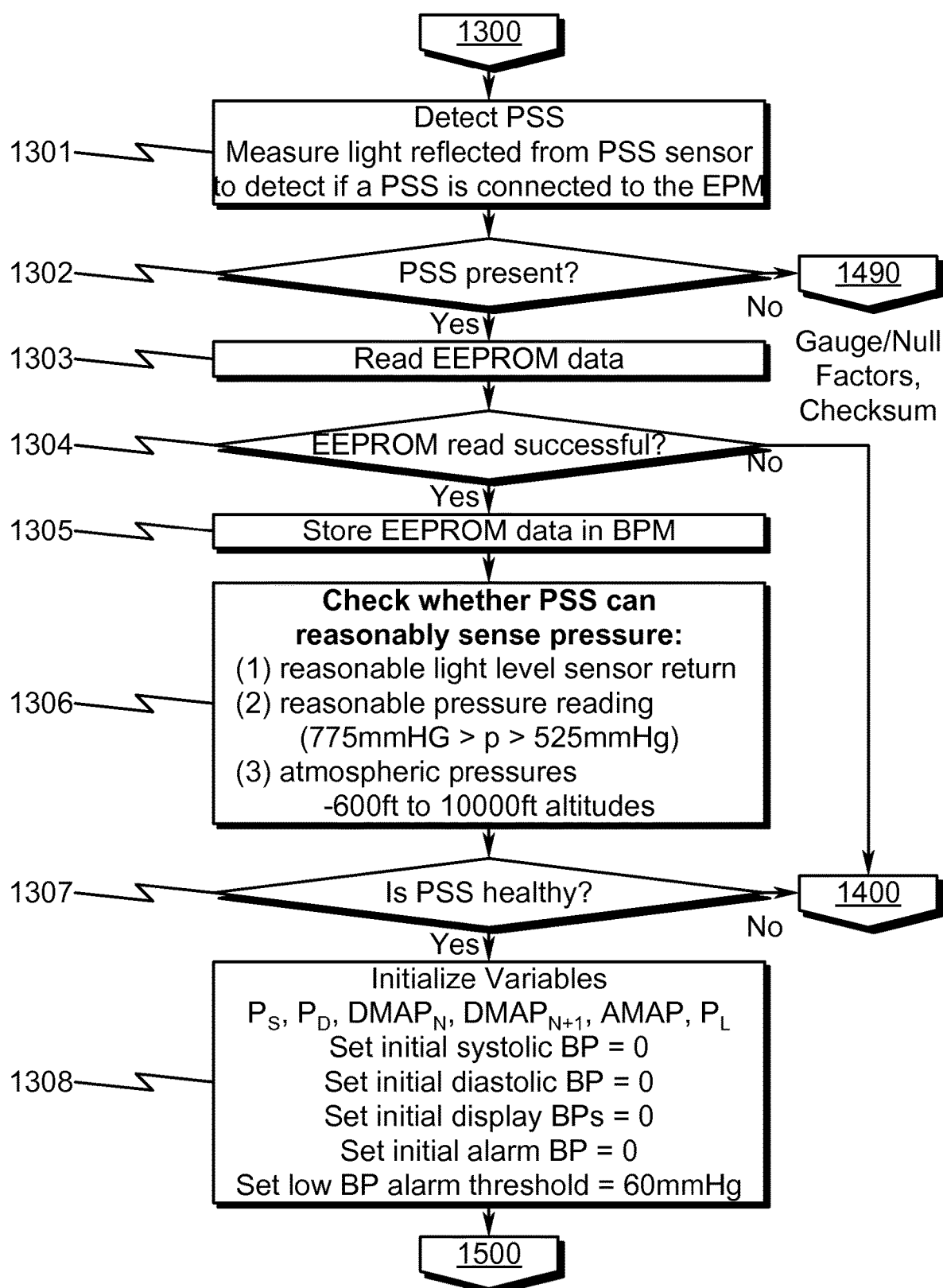
FIG. 13 illustrates an exemplary sub-process detail flowchart implementing sub-functions of the main BPM flowchart that incorporate the teachings of the present invention.
Figure 14:
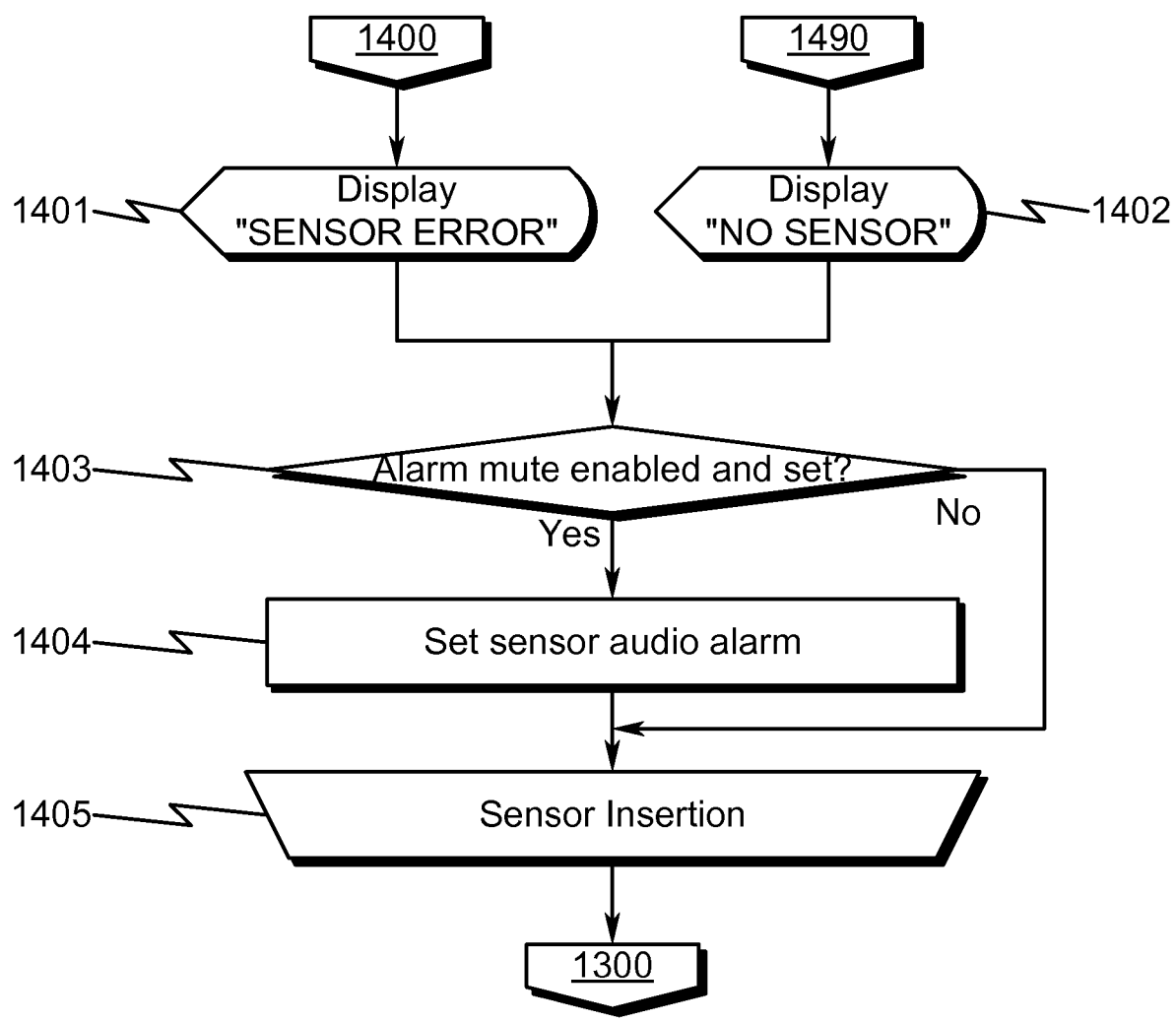
FIG. 14 illustrates an exemplary sub-process detail flowchart implementing sub-functions of the main BPM flowchart that incorporate the teachings of the present invention.
Figure 15:
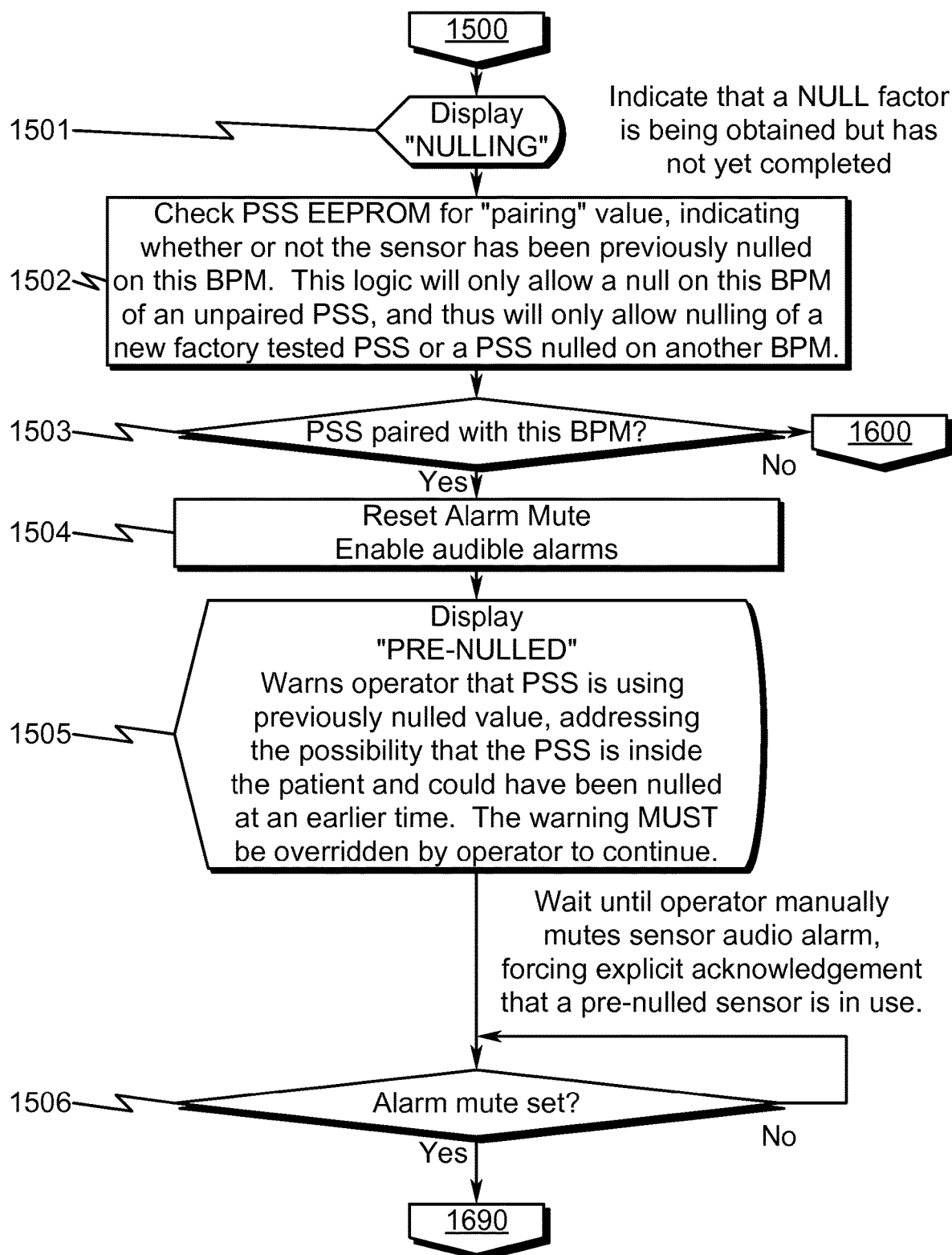
FIG. 15 illustrates an exemplary sub-process detail flowchart implementing sub-functions of the main BPM flowchart that incorporate the teachings of the present invention.
Figure 16:
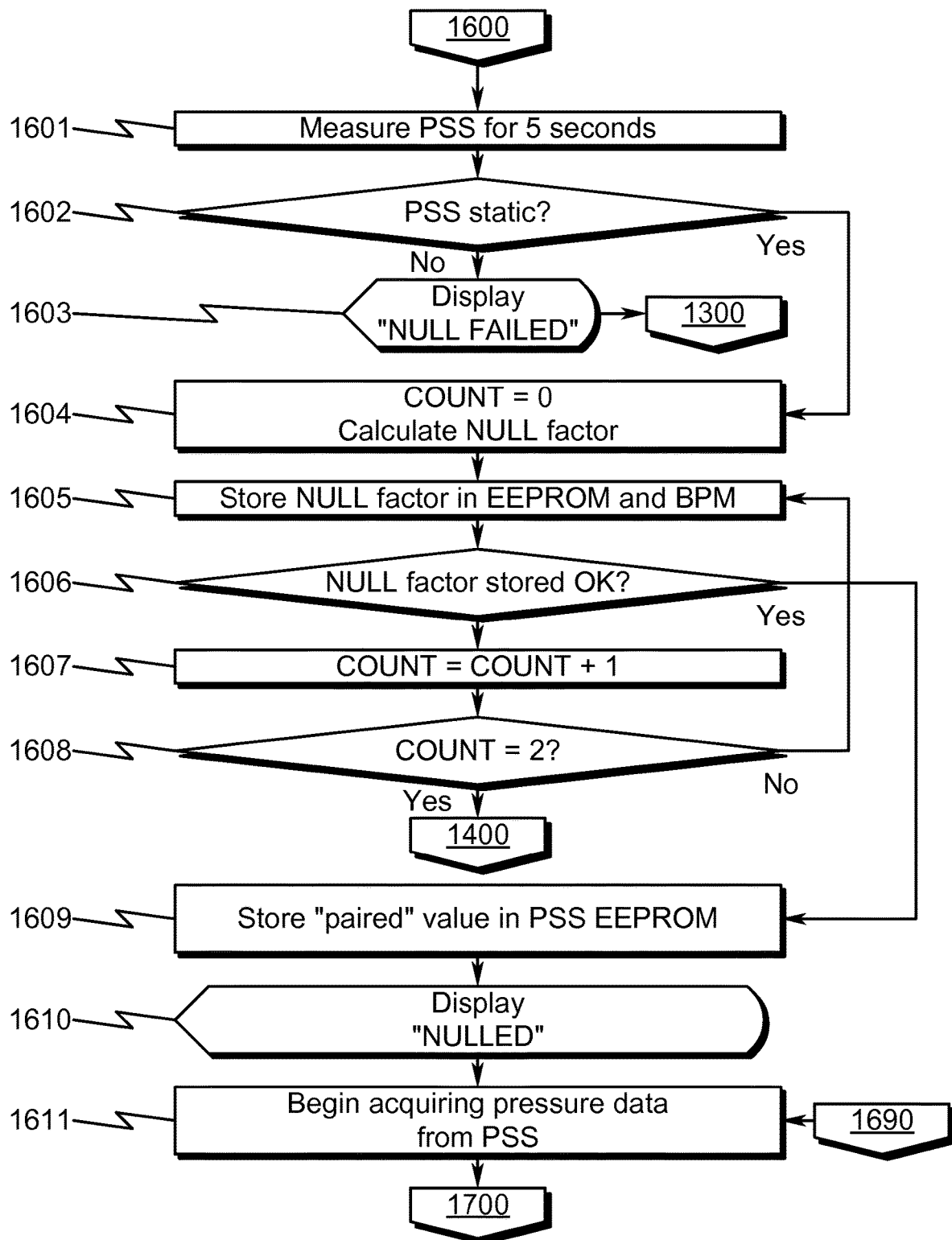
FIG. 16 illustrates an exemplary sub-process detail flowchart implementing sub-functions of the main BPM flowchart that incorporate the teachings of the present invention.
Figure 17:
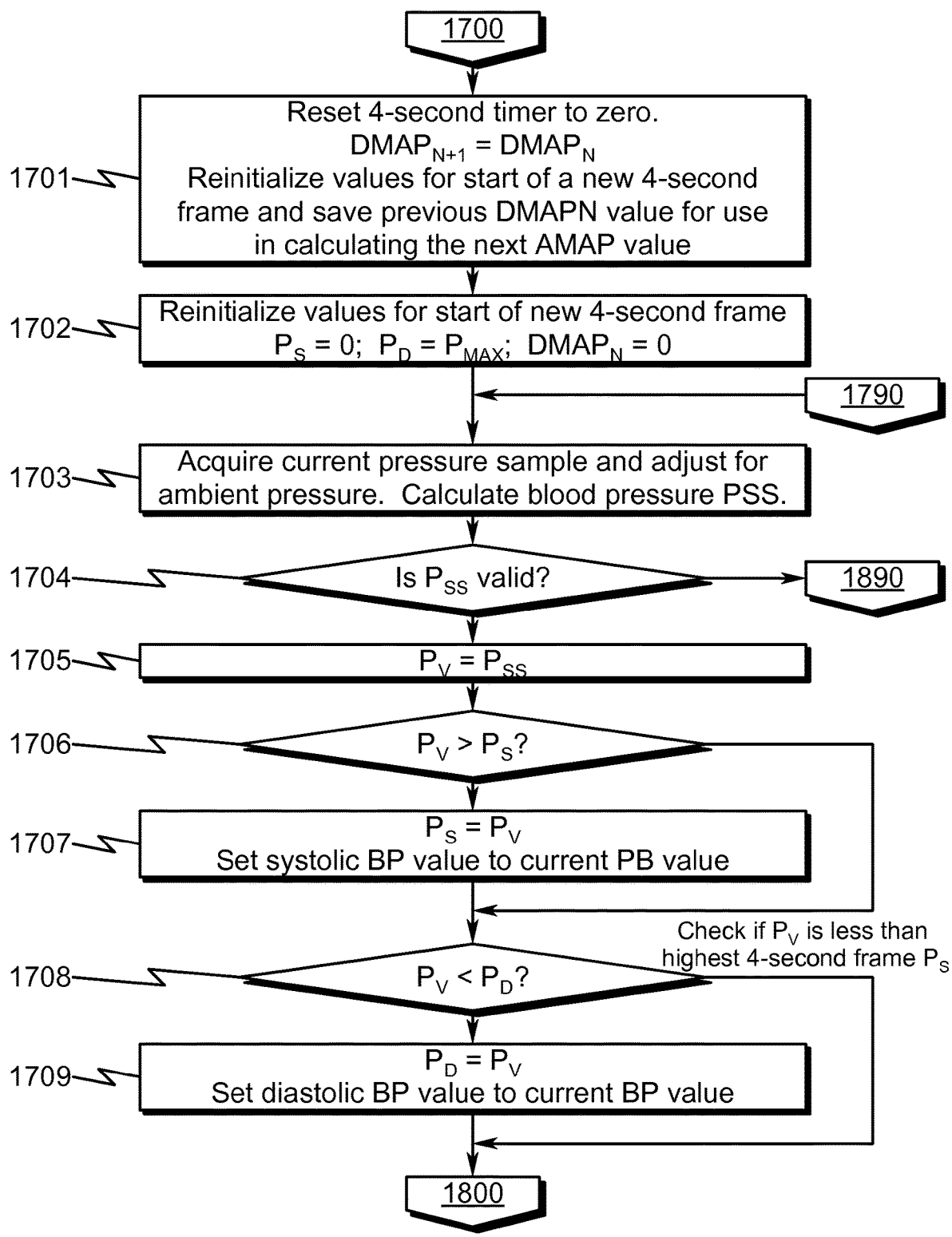
FIG. 17 illustrates an exemplary sub-process detail flowchart implementing sub-functions of the main BPM flowchart that incorporate the teachings of the present invention.
Figure 18:
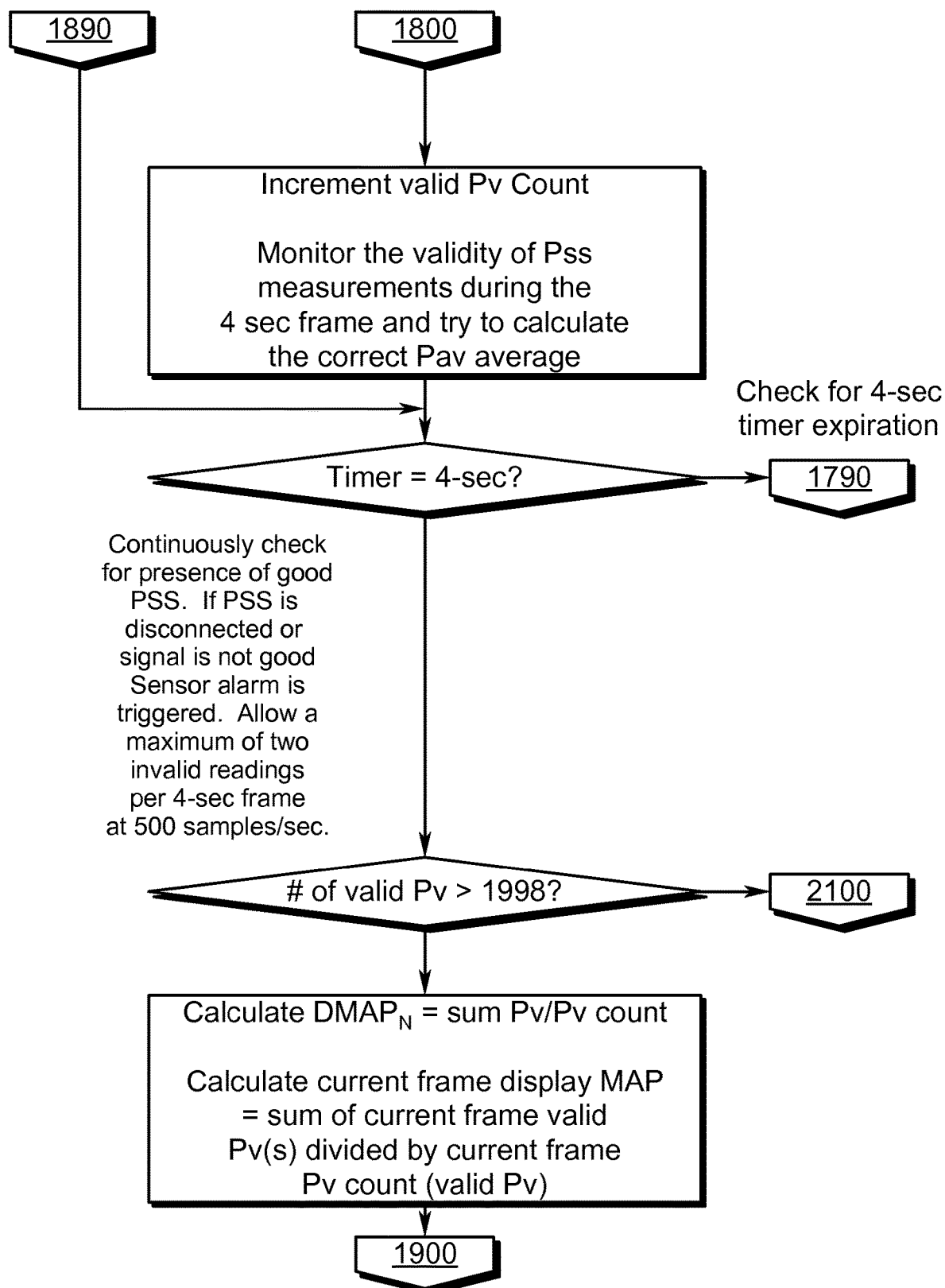
FIG. 18 illustrates an exemplary sub-process detail flowchart implementing sub-functions of the main BPM flowchart that incorporate the teachings of the present invention.
Figure 19:
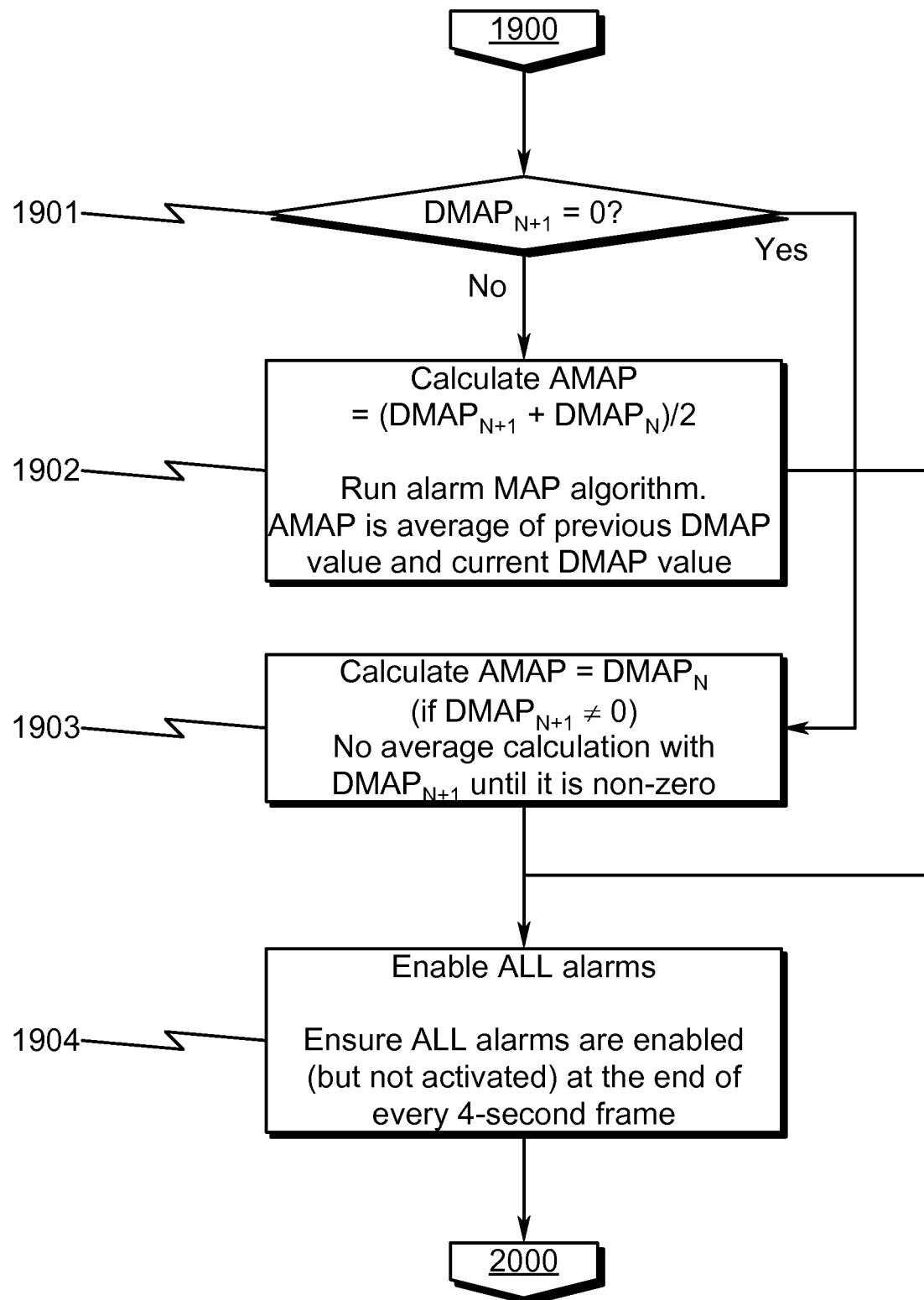
FIG. 19 illustrates an exemplary sub-process detail flowchart implementing sub-functions of the main BPM flowchart that incorporate the teachings of the present invention.
Figure 20:
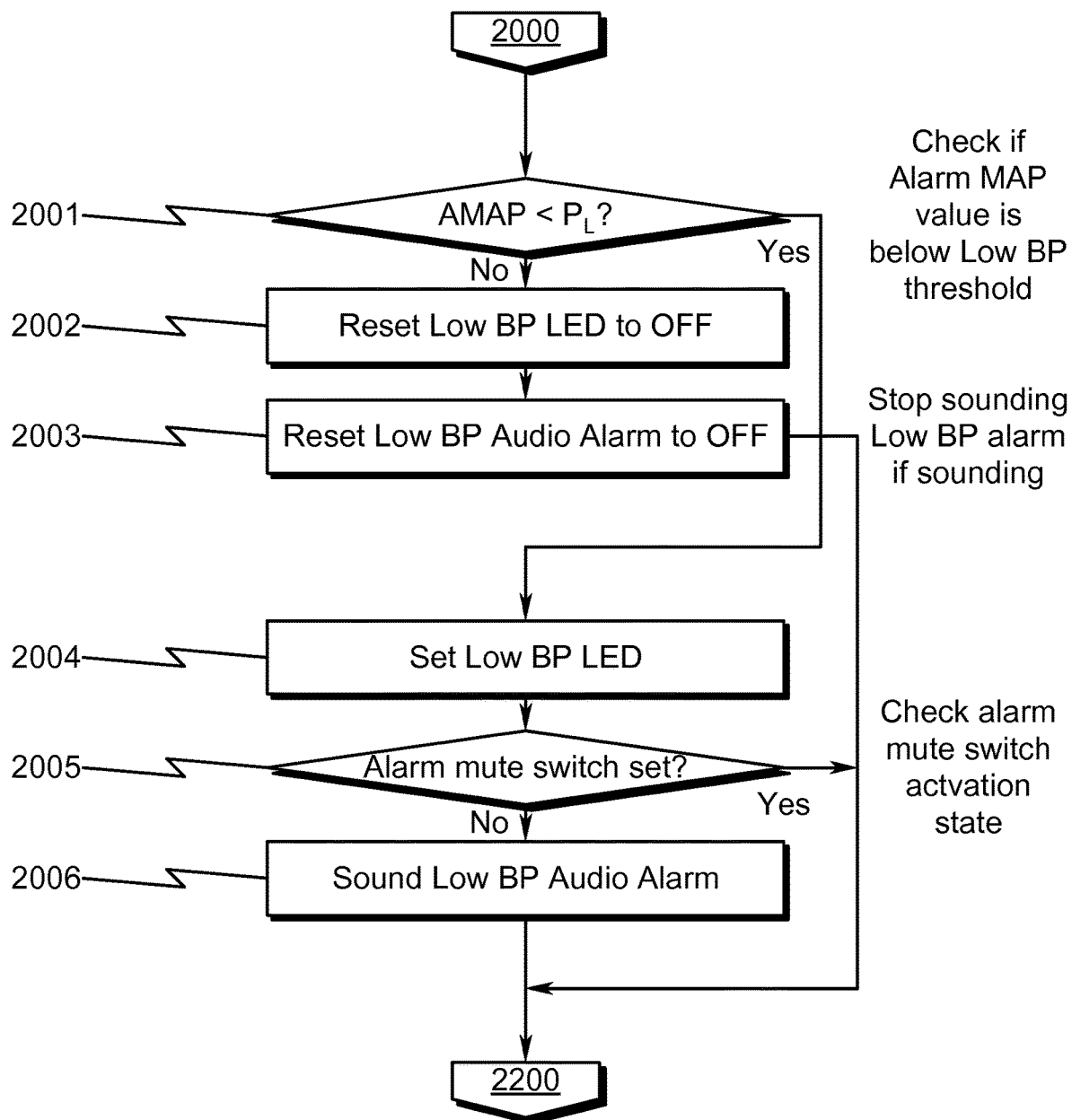
FIG. 20 illustrates an exemplary sub-process detail flowchart implementing sub-functions of the main BPM flowchart that incorporate the teachings of the present invention.
Figure 21:
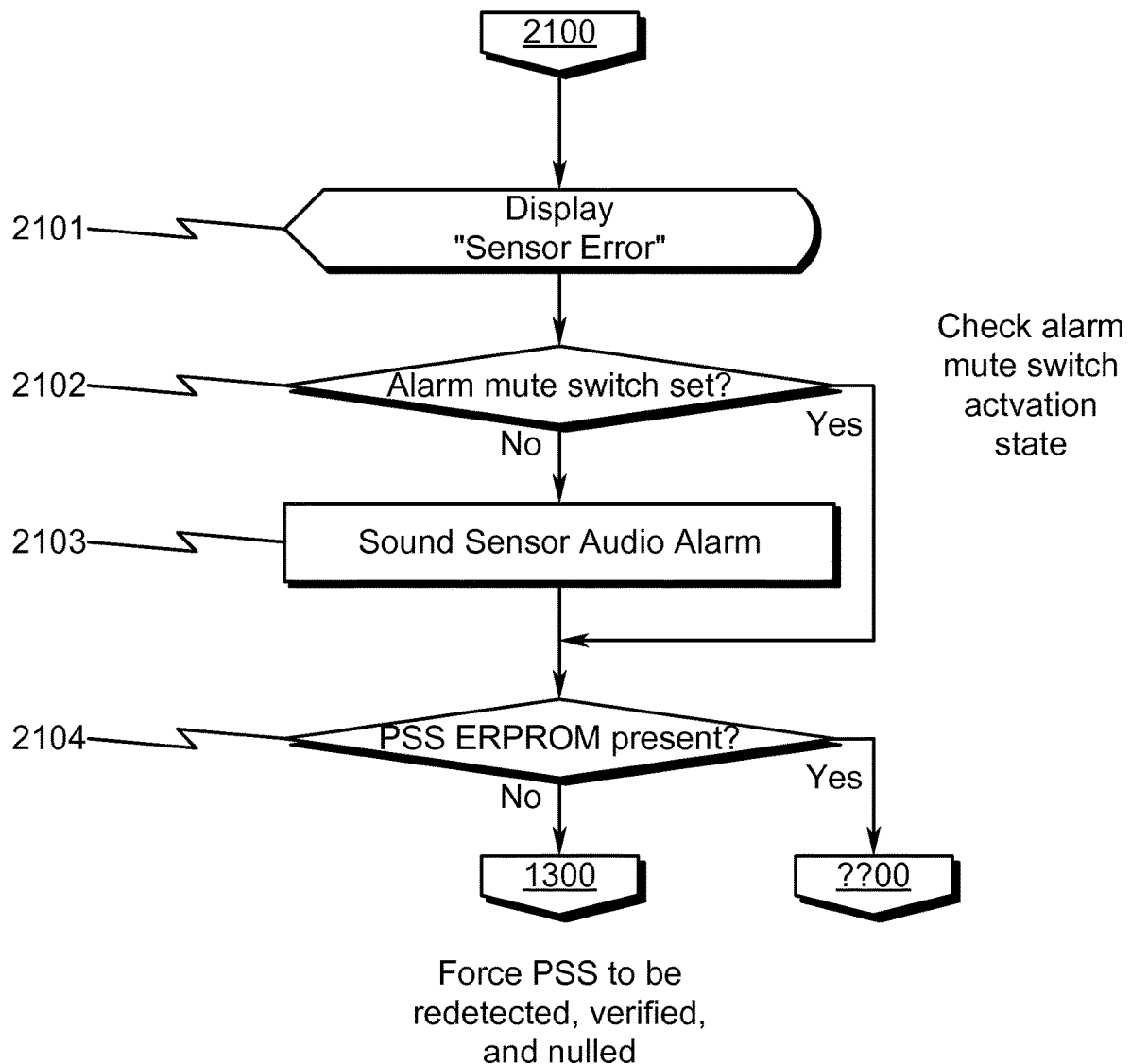
FIG. 21 illustrates an exemplary sub-process detail flowchart implementing sub-functions of the main BPM flowchart that incorporate the teachings of the present invention.
Figure 22:
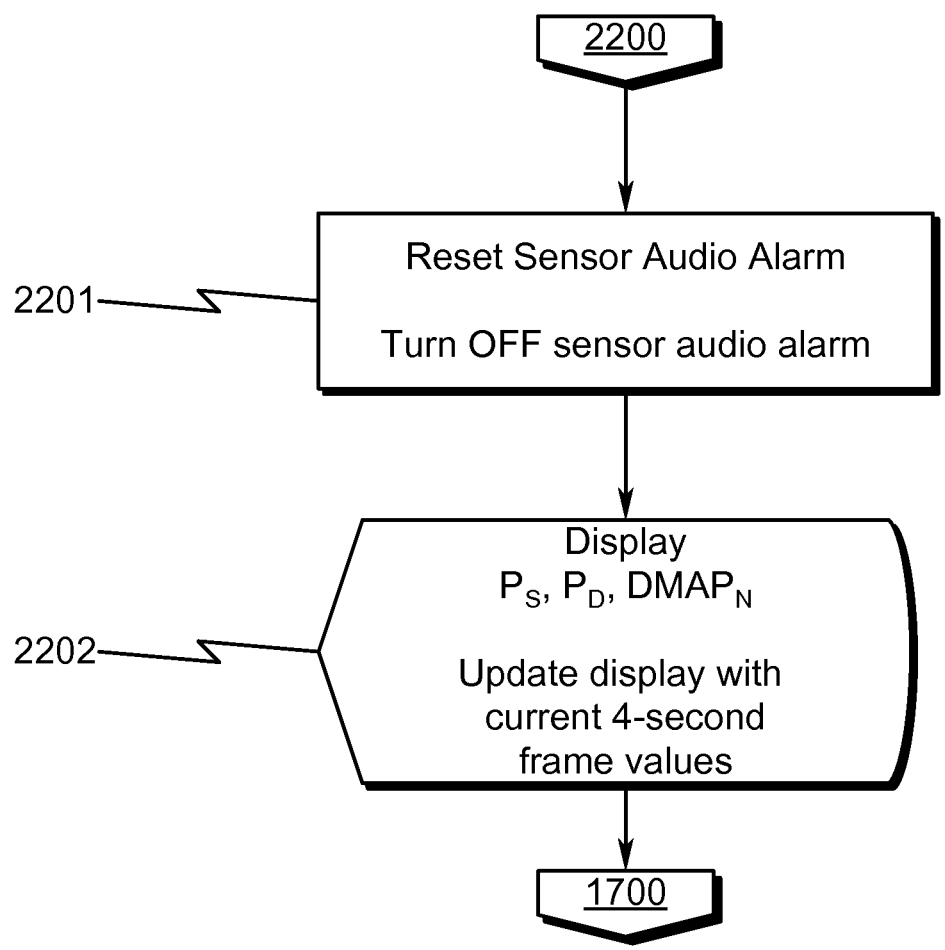
FIG. 22 illustrates an exemplary sub-process detail flowchart implementing sub-functions of the main BPM flowchart that incorporate the teachings of the present invention.
Figure 23:
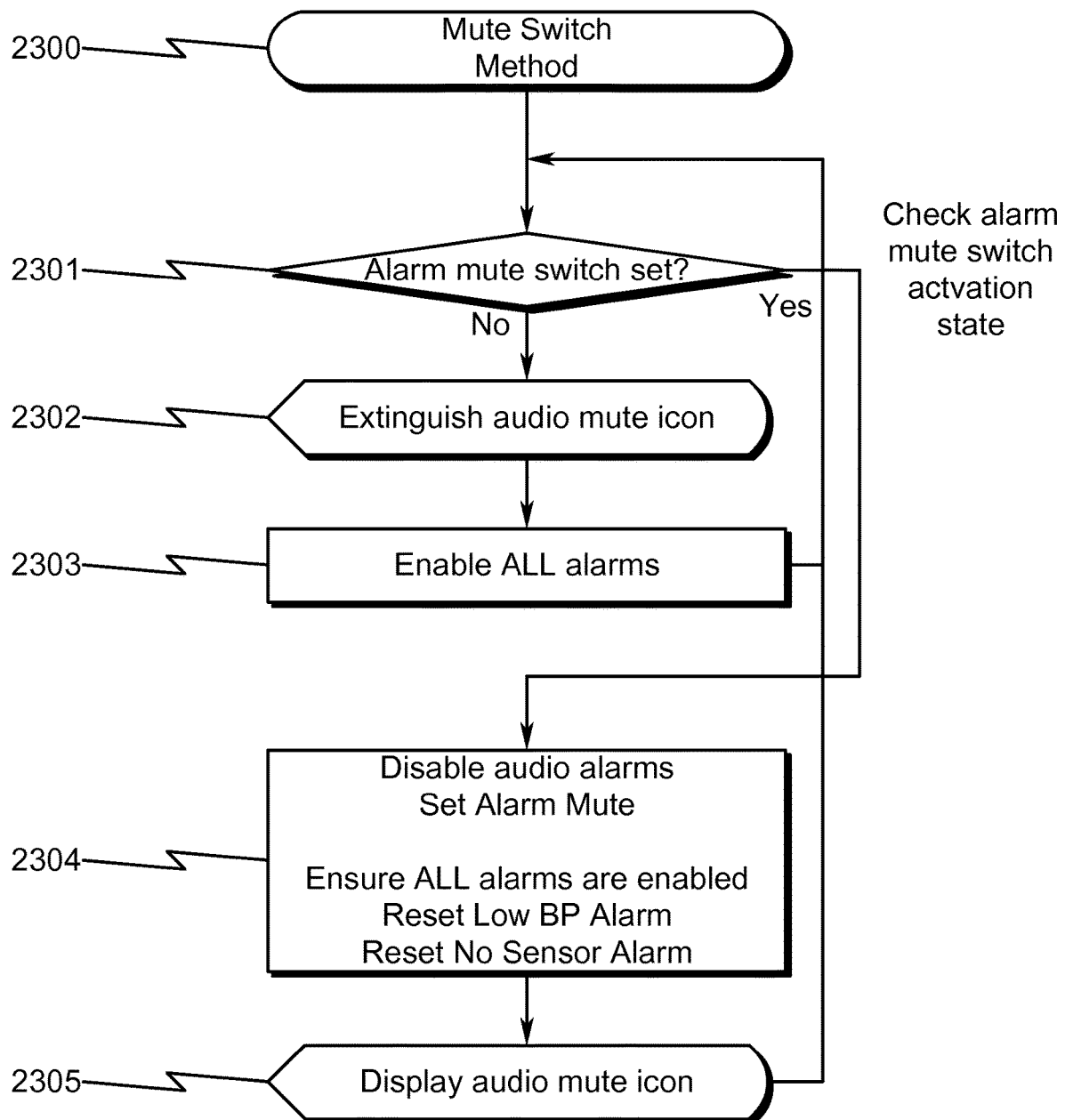
FIG. 23 illustrates an exemplary sub-process detail flowchart implementing sub-functions of the main BPM flowchart that incorporate the teachings of the present invention.
Figure 24:
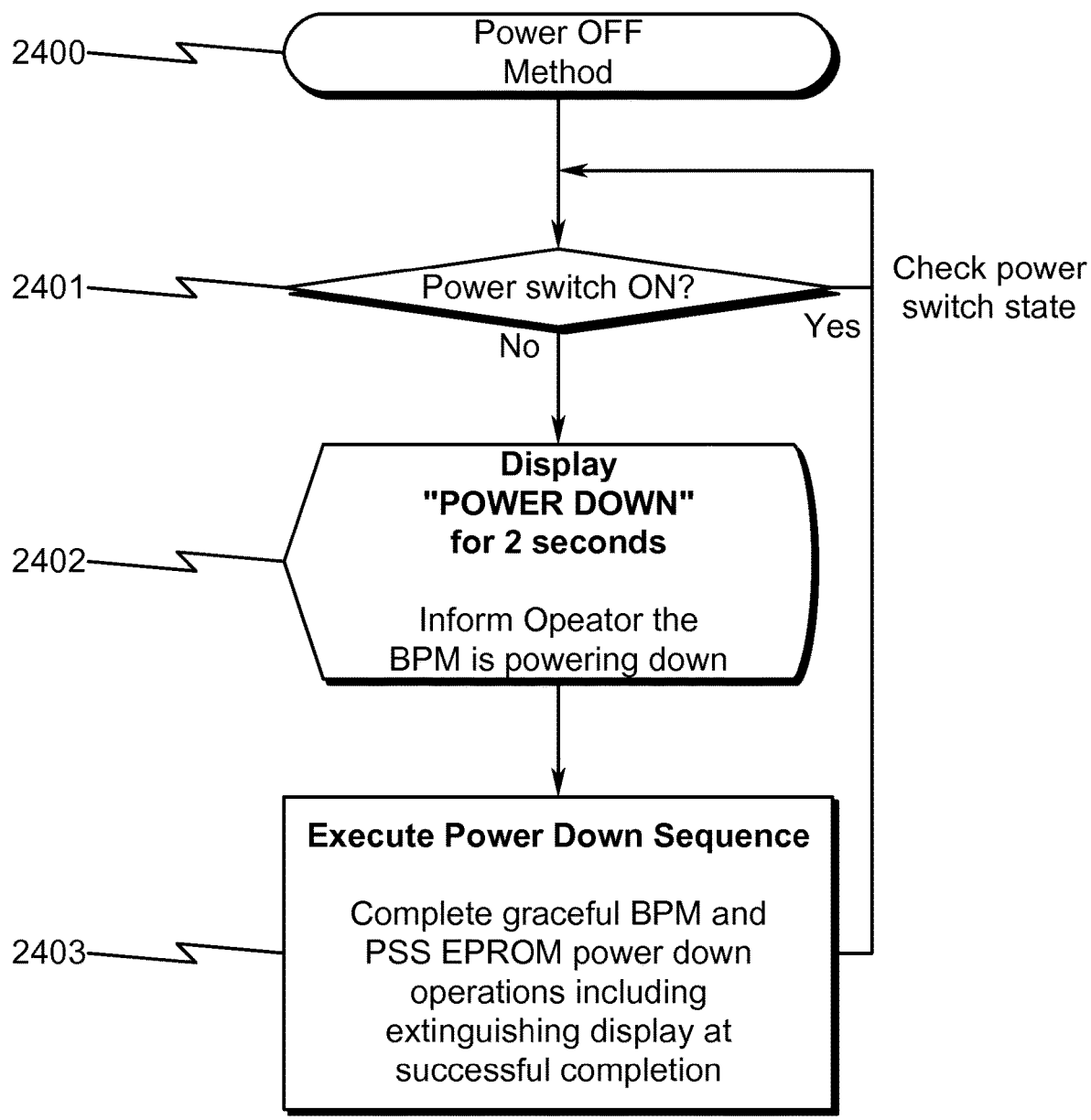
FIG. 24 illustrates an exemplary sub-process detail flowchart implementing sub-functions of the main BPM flowchart that incorporate the teachings of the present invention.

The present invention may be embodied in a wide variety of method variants. However, a preferred method embodiment implementing a blood pressure monitor is generally illustrated in FIG. 11 (1100)-FIG. 24 (2400), with a general user interface flowchart associated with the BPM methodology illustrated in FIG. 25 (2500)-FIG. 32 (3200).

Exemplary Embodiment User Interface (2500-3200)

Figure 26:
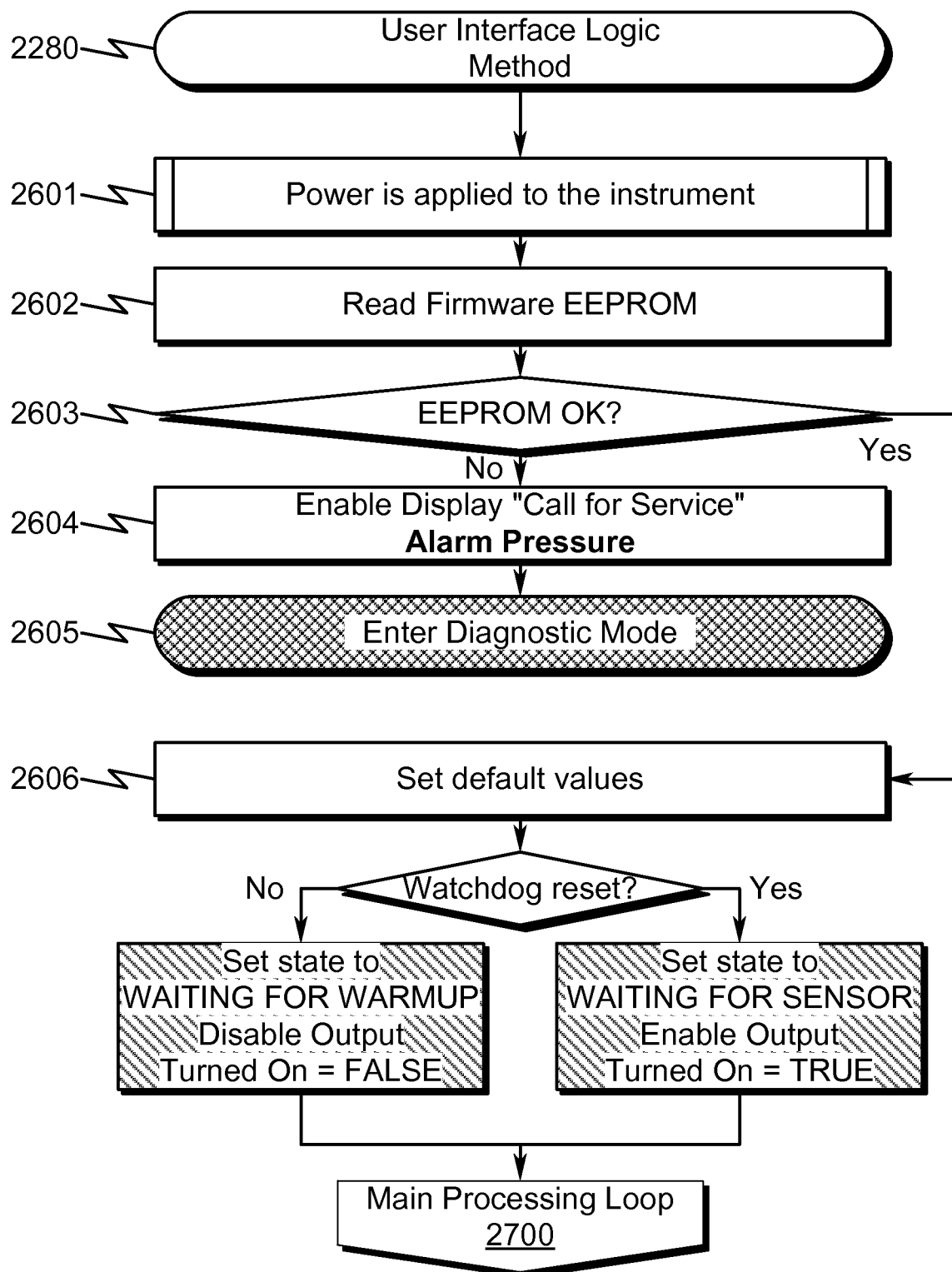
FIG. 26 illustrates a flowchart depicting an exemplary user interface logic method used in some preferred exemplary embodiments of the present invention.

While the present invention may incorporate a wide variety of user interfaces, some embodiment configurations are preferred. Within this context, the following discussion details one preferred user interface.
General Alarm Logic (2500)
As an aid to understanding some possible constructions of the present invention, FIG. 25 (2500) illustrates exemplary user alarm states associated with a preferred embodiment of the present invention. As seen from this flowchart, alarm values may have associated an audible intensity and duration pattern as well as visual indicia of the alarm status with provisions for muting by the operator.
User Interface Logic Initialization (2600)
FIG. 26 (2600) generally illustrates initialization sequences associated with the user interface as well as power-on self-test features.

User Interface Processing Loop (2700)

Figure 27:
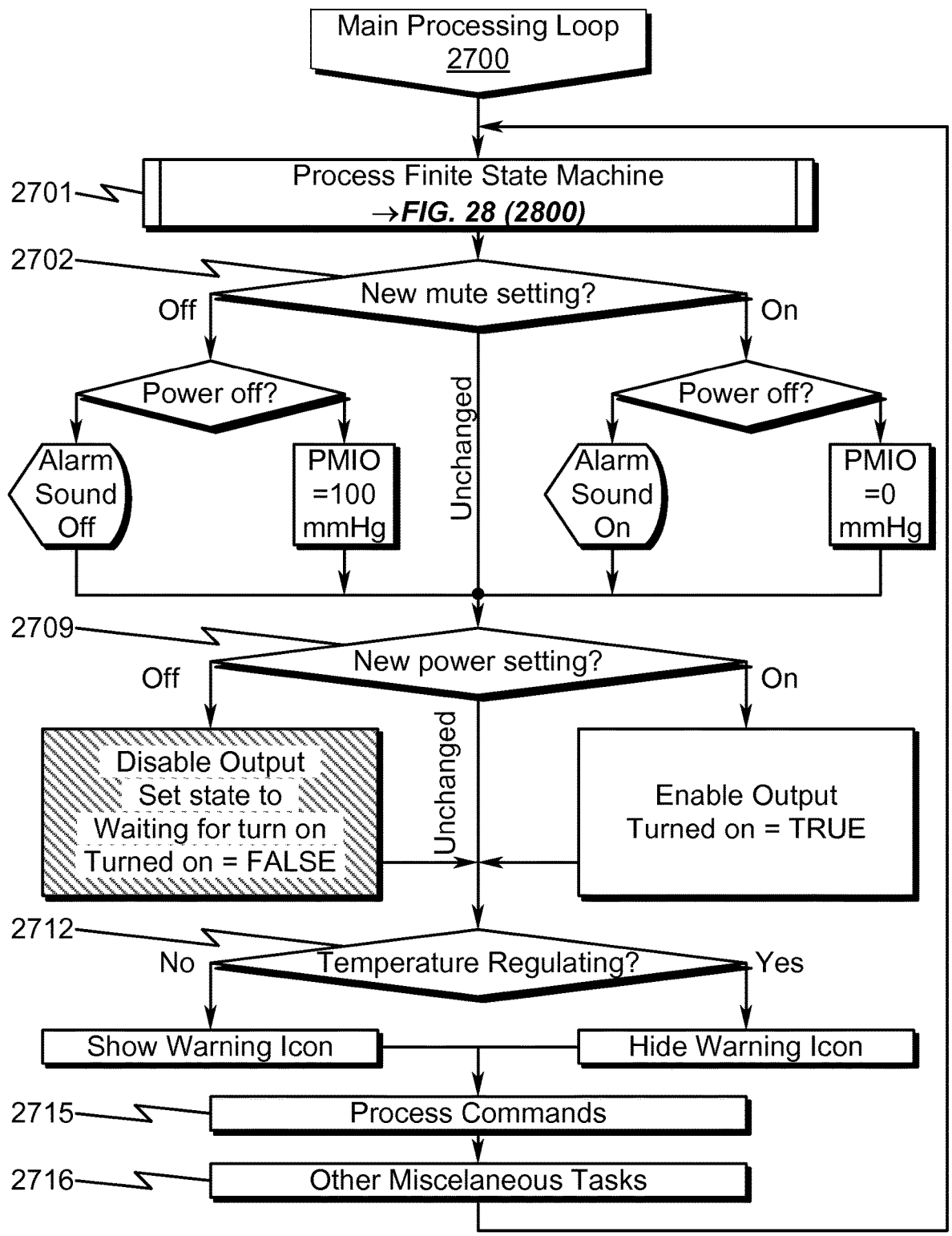
FIG. 27 illustrates a flowchart depicting a main processing loop method used in an alternative preferred exemplary embodiment of the present invention.

FIG. 27 (2700) generally illustrates the main processing loop associated with the user interface. Command processing within this structure normally is completed by a finite state machine detailed below.

User Interface Finite State Machine States (2800)

Figure 28:
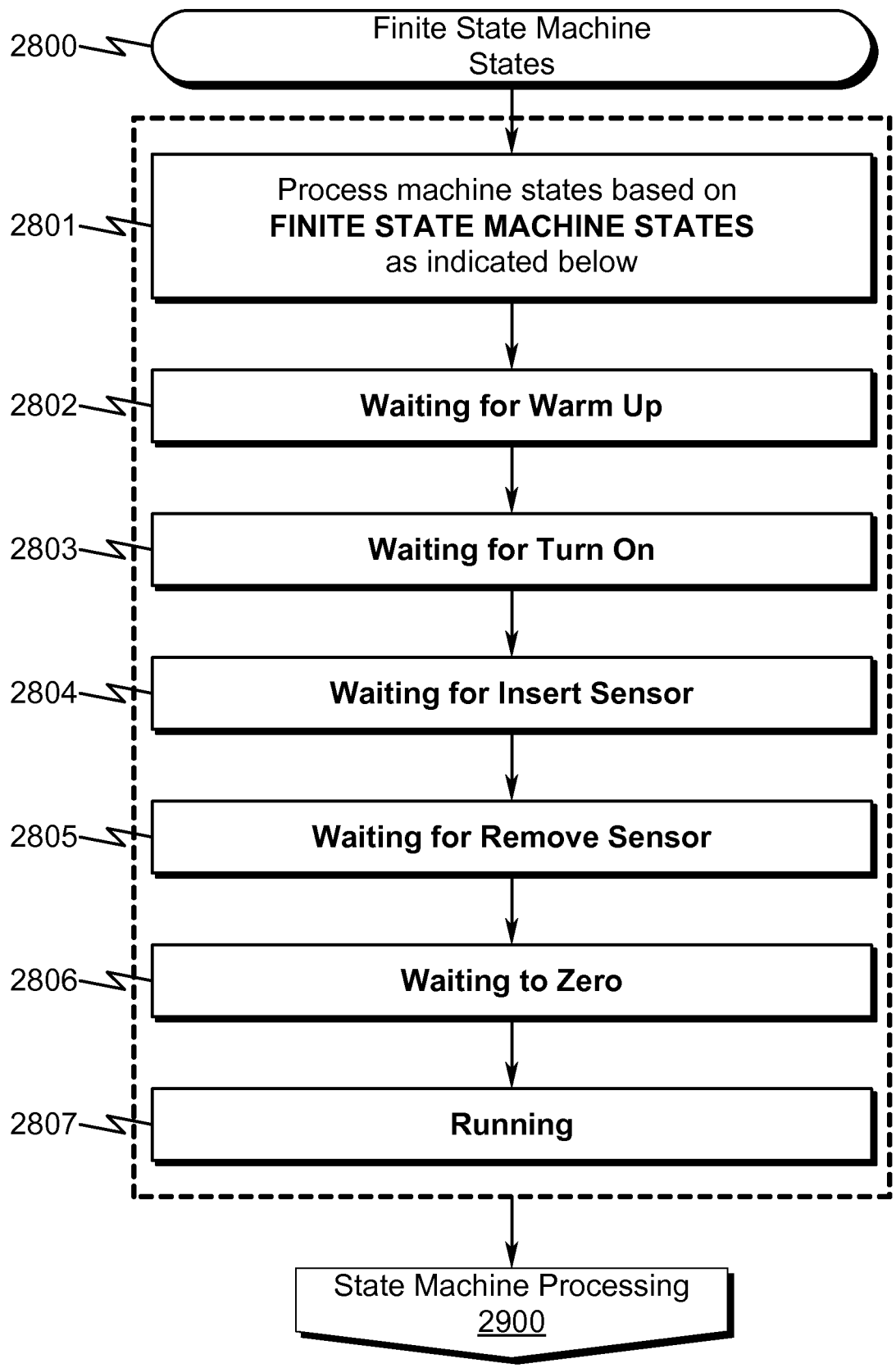
FIG. 28 illustrates exemplary finite state machine states associated with a preferred exemplary embodiment of the present invention.

FIG. 28 (2800) generally illustrates a variety of states associated with a finite state machine that may operate the user interface. Actual processing of these states is accomplished using a finite state machine method detailed below.

Finite State Machine Method (2900)

Figure 29:
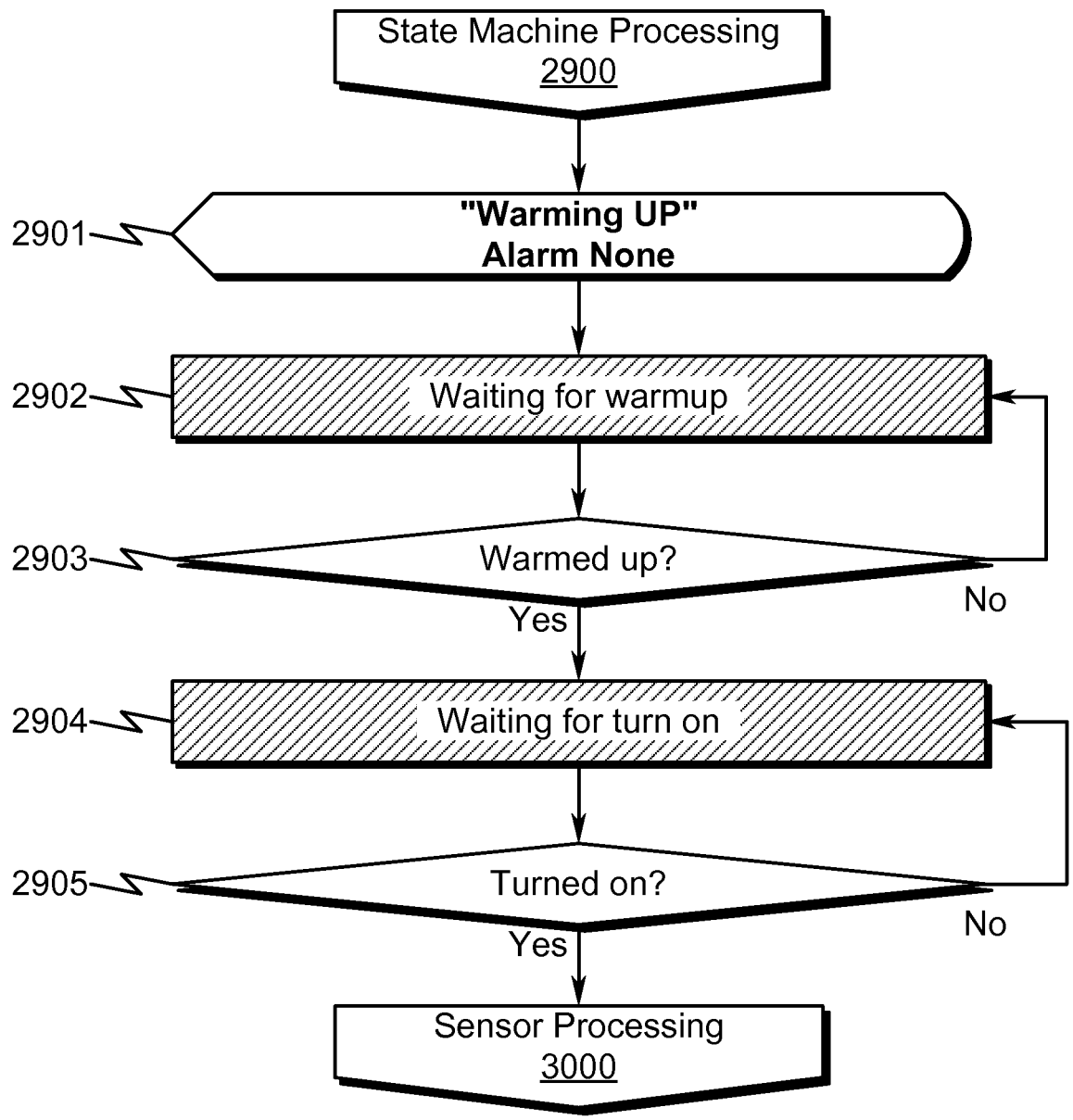
FIG. 29 illustrates a flowchart depicting a finite state machine processing method used in some preferred exemplary embodiments of the present invention.

FIG. 29 (2900) generally illustrates a finite state machine method that may operate in conjunction with status changes to the user interface. Once the BPM is powered on and warmed up, sensor processing begins as detailed below.

Sensor Processing Method (3000)

Figure 30:
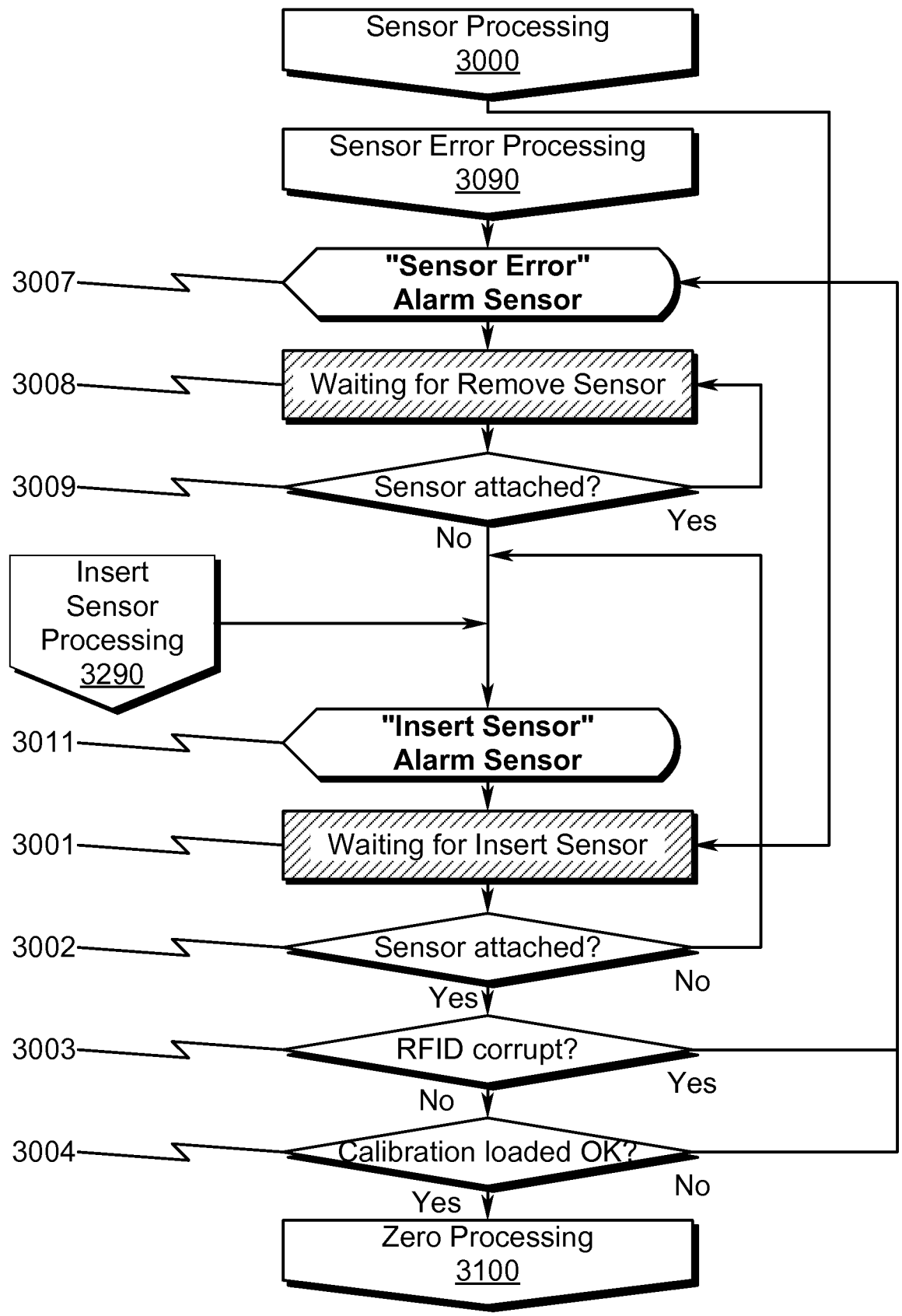
FIG. 30 illustrates a flowchart depicting a sensor processing method used in some preferred exemplary embodiments of the present invention.

FIG. 30 (3000) generally illustrates a sensor processing method that may operate in conjunction with the finite state machine to affect the user interface. Within this sensor processor is an additional zero processing method described below that enables a zero baseline pressure to be accurately determined. The sensor processing method 3000 includes:
  Waiting for Insert Sensor 3001;
  Checking if Sensor Attached? 3002;
    If the answer is no,
    Conducting Insert Sensor Processing 3290 including:
      Displaying "Insert Sensor" 3011; and
      Activating Alarm Sensor 3011;
  Waiting for Insert Sensor 3001;
  Checking if Sensor Attached? 3002;
    If the answer is yes,
    Checking if RFID corrupt? 3003;
      If the answer is yes,
        Conducting Sensor Error Processing 3090 including:
          Displaying "Sensor Error" 3007; and
          Activating Alarm Sensor 3007;
          Waiting for Remove Sensor 3008;
          Checking if Sensor Attached 3009
            If the answer is Yes,
              then repeat wait for Remove Sensor 3008;
            If the answer is No,
              then begin Insert Sensor Processing 3290;
          Displaying "Insert Sensor" 3011; and
          Activating Alarm Sensor 3011;
      Waiting for Insert Sensor 3001;
      Checking if Sensor Attached? 3002;
        If the answer is yes,
        Checking if RFID corrupt? 3003;
        If the answer is "No";
          Load calibration (gauge factors) and check if load ok 3004:
            If the answer is no, then conduct Sensor Error Processing 3090;
            If the answer is yes, then conduct Zero Processing 3100.

Zero Detection Method (3100).

Figure 31:
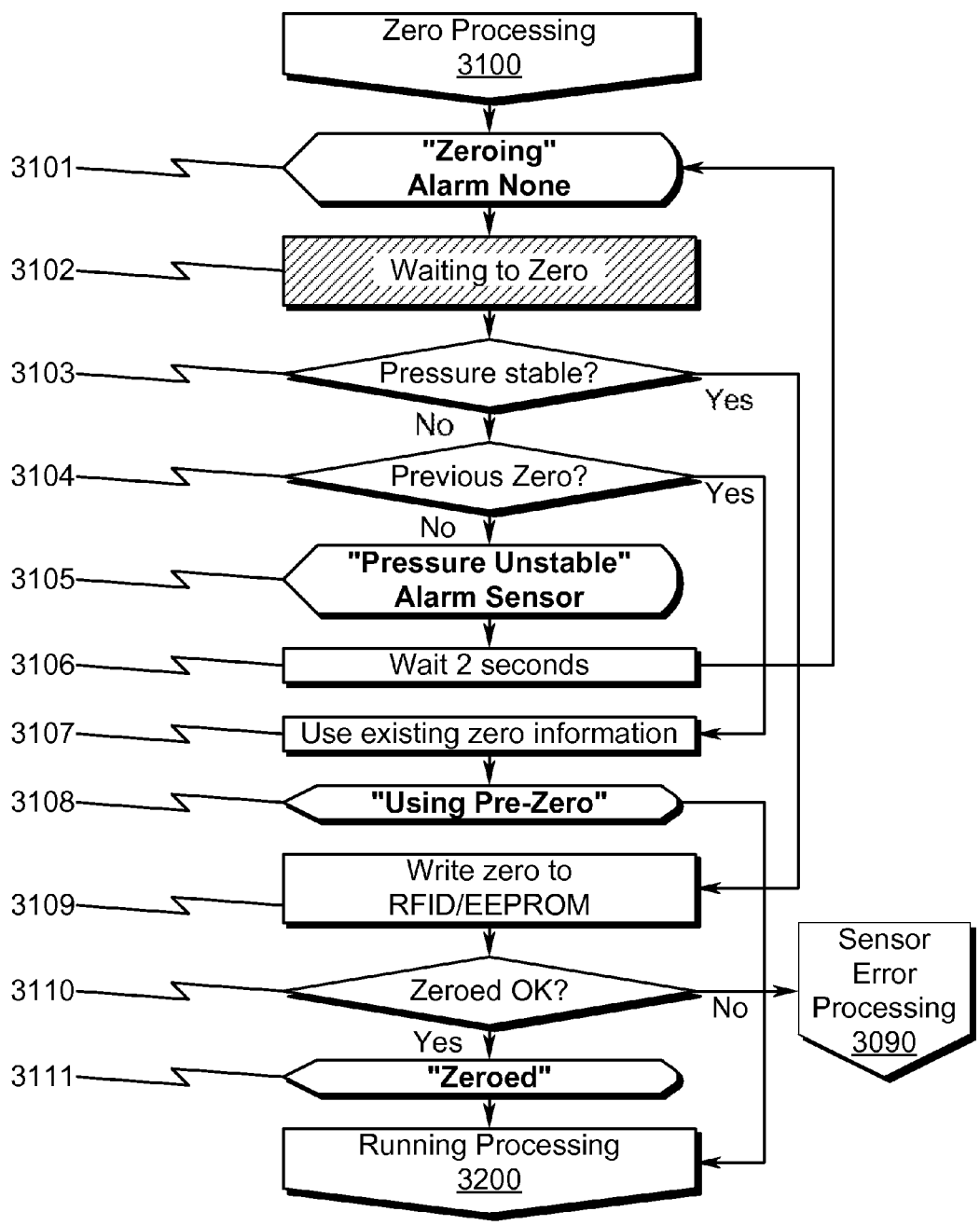
FIG. 31 illustrates a flowchart depicting a zero processing method used in some preferred exemplary embodiments of the present invention.

FIG. 31 (3100) generally illustrates a zero detection method that may operate in conjunction with the finite state machine to properly calibrate the BPM sensor within the context of the user interface. Once zero calibration is achieved, normal running processing is enabled as detailed below. The sensor processing method 3001 includes:
  Displaying "Zeroing" 3101;
  Deactivating Alarm 3101;
  Waiting to Zero 3102;
  Check if Pressure is stable 3103;
    If the answer is no,
      Check for Previous Zero 3104;
        If the answer is no,
          Displaying "Pressure Unstable" 3105;
          Activating Alarm Sensor 3105;
          Waiting 2 seconds 3106;
  Displaying "Zeroing" 3101;
  Deactivating Alarm 3101;
  Waiting to Zero 3102;
  Check if Pressure is stable 3103;
    If the answer is no,
      Check for Previous Zero 3104;
        If the answer is yes,
          Writing zero to RFID/EEPROM 3109;
          Checking if Zeroed Ok 3110;
            If the answer is no,
              Conducting Sensor Error Processing 3090;
            If the answer is yes,
              Displaying "Zeroed" 3111; and
  Running Processing 3200.
In addition, the sensor processing method 3000 includes:
  Displaying "Zeroing" 3101;
  Deactivating Alarm 3101;
  Waiting to Zero 3102;
  Check if Pressure is stable 3103;
    If the answer is yes,
      Writing zero to RFID/EEPROM 3109;
      Checking if Zeroed Ok 3110;
        If the answer is no,
          Conducting Sensor Error Processing 3090;
        If the answer is yes,
          Displaying "Zeroed" 3111; and
  Running Processing 3200.

Running Method (3200)

Figure 32:
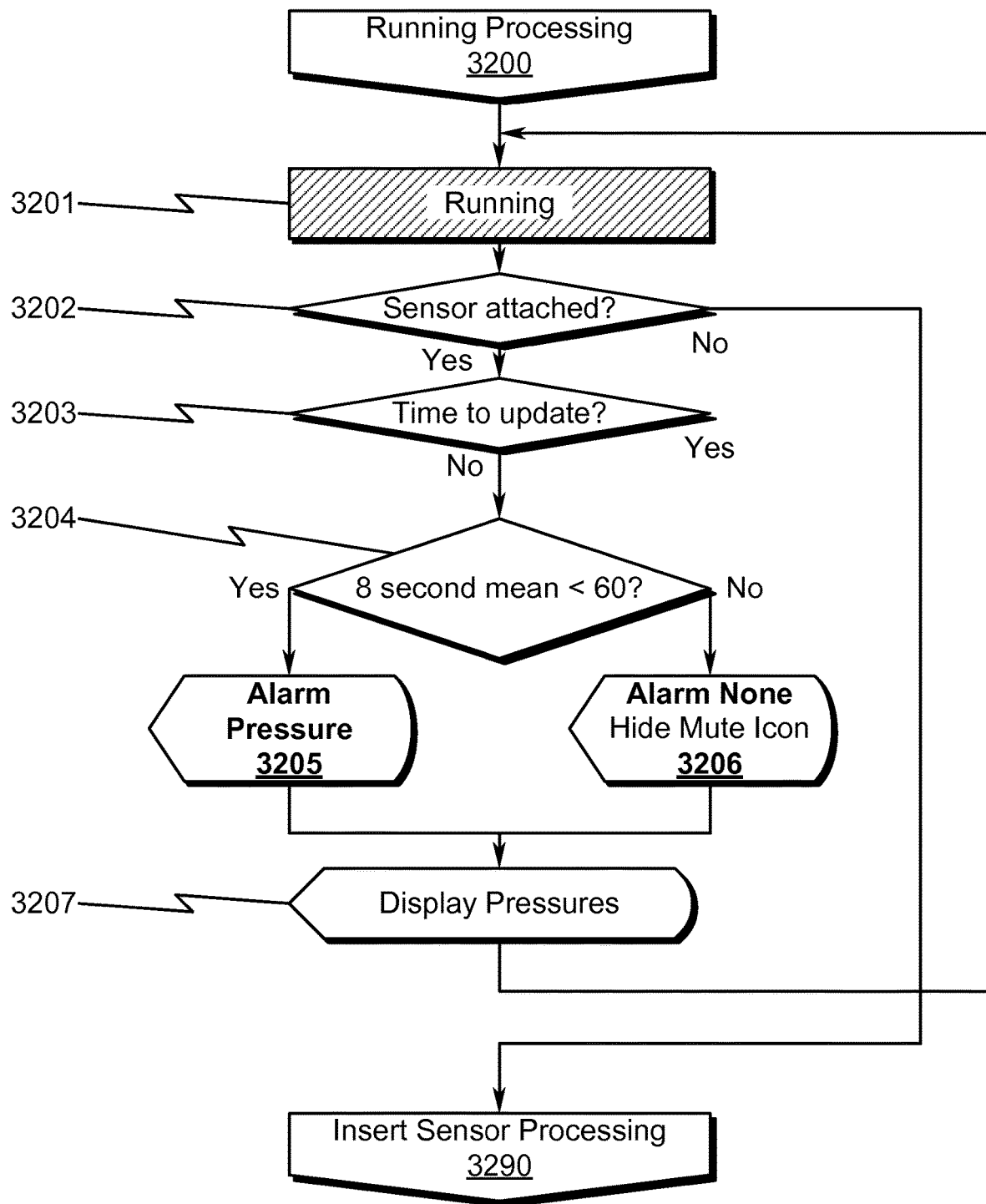
FIG. 32 illustrates a flowchart depicting a running processing method used in some preferred exemplary embodiments of the present invention.

FIG. 32 (3200) generally illustrates a running method that operates with the finite state machine to read the BPM sensor within the context of the user interface and display measured blood pressure values. This processing loop generally continues until the BPM sensor is detected as unavailable for measurement capture.

Exemplary Embodiment Functional Specification

While the present invention may be embodied in many forms, some embodiment configurations are preferred. As an aid to understanding some possible constructions of the present invention, the following product requirement definition (PRD) specification provides additional detail relating to some preferred invention embodiments.

Note that the use of the terms "shall," "will," "must" and similarly restrictive terms are not intended to limit the scope of the claimed invention, but rather to simply present one preferred exemplary embodiment specification that is thought to have optimal commercial value at present. One skilled in the art will recognize that many variations in the specification are possible with such a product requirements document without departing from the spirit of the disclosed invention.

Nomenclature

The following nomenclature will be utilized within this exemplary embodiment functional specification:
AC Alternating current
AMAP Alarm mean arterial blood pressure
ASTM American Society for Testing and Materials
BP Blood pressure C Centigrade
CAD Computer aided design
CAM Computer aided manufacturing
CCD Charge coupled device
CE mark Conformité Européenne, French for "European conformity"
DAC Digital to analog converter
DC Direct current
Diastolic Diastolic pressure is the minimum pressure in an artery
DMAP Display mean arterial blood pressure
EMC Electromagnetic compatibility
EMI Electromagnetic interference
BPM Blood Pressure Monitor
ESD Electrostatic Discharge
EU European Union
F Fahrenheit
FCC Federal Communications Commission
FOMA Fiber Optic Measurement Assembly
FOMS Fiber Optic Measurement System
Hg Chemical symbol for mercury
Hz Hertz
ISTA International Safe Transit Association
LED Light emitting diode
MB Megabyte
mm Millimeter
ms Millisecond
MRI Magnetic resonance imaging
MAP Mean arterial blood pressure
OEM Original equipment manufacturer
PRD Product requirements document
PMI Patient Monitor Interface
PMIO Patient Monitor Interface Output
PSS Pressure Sensing Sheath
RFID Radio Frequency Identification
RMS Root mean square
RoHS Restriction of Hazardous Substances Directive
SC Fiber optic signal conditioner
SCPI Standard commands for programmable instrumentation
Systolic Systolic pressure is peak pressure in an artery
UL Underwriters Laboratory
USB Universal Serial Bus
uA Microampere
uV Microvolt
V Volt
VAC Volts alternating current
VDC Volts direct current Scope Intent This Product Requirements Document (PRD) provides a definition of the functional characteristics of the Blood Pressure Monitor (BPM) product. The PRD is intended to document these characteristics for internal use and to provide a functional description to be used for an engineering organization in developing a project cost and schedule estimate, and subsequently a product specification.

Indentification (3300)

Figure 33:
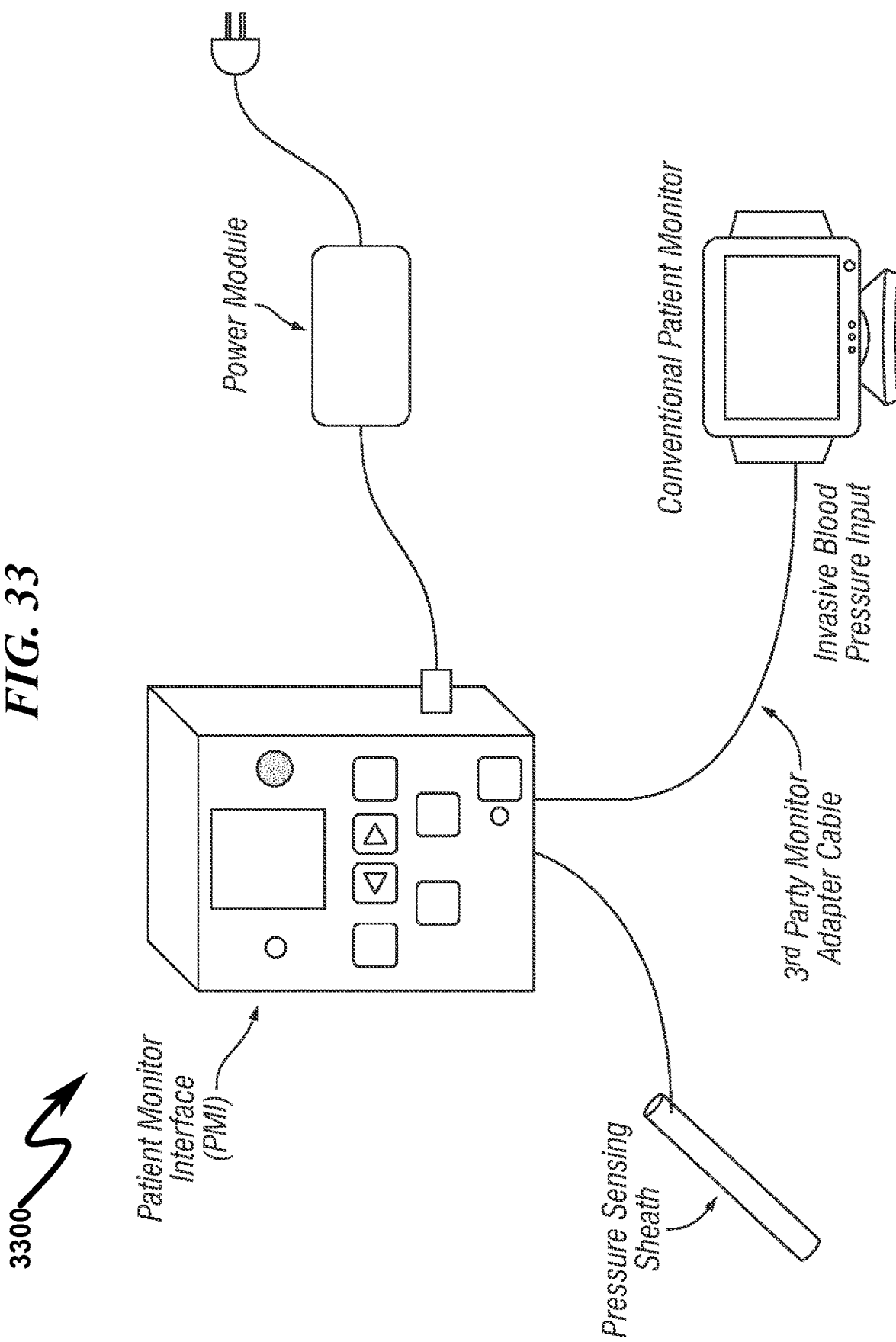
FIG. 33 illustrates a blood pressure monitor sensing sheath system as described by an exemplary product requirements document detailing the construction of a preferred exemplary embodiment of the present invention as applied to a blood pressure monitor (BPM) system.

The following description applies specifically to the BPM that is a subsystem of the Pressure Sensing Sheath (PSS) system. It converts optical data from a fiber optic blood pressure sensor into blood pressure values displayed on the front of the BPM and/or into signals appropriate for input to a standard invasive blood pressure clinical patient monitor. A general overview of this application context is provided in FIG. 33 (3300).

System Overview

The BPM converts optical blood pressure transducer data into blood pressure values useful to clinical personnel. The BPM is meant to be used initially in minimally invasive vascular procedures and critical patient care situations where the accuracy and timeliness of arterial blood pressure measurements are very important. It explicitly supports disposable fiber optic transducers that may be incorporated into medical devices such as catheters and sheaths.

The BPM is an electronic device that provides compatibility between a physiological fiber optic blood pressure sensor (transducer) and conventional invasive arterial blood pressure inputs to a standard physiological patient monitor. The device converts the optical transducer data to electrical signals that are interpreted by a conventional patient monitor and/or are displayed directly on the BPM. The BPM accurately emulates a fluidic arterial blood pressure transducer and supplies electrical signals to its output that are indistinguishable from a conventional fluidic blood pressure transducer.

The BPM is implemented as a self-contained unit that has a fiber optic transducer connection as an input source and communicates with a patient monitor as its output. The BPM acts to directly emulate the electrical interface characteristics of conventional fluidic blood pressure transducers (that patient monitors are compatible with) while providing much more precise blood pressure data derived from a fiber optic transducer placed within an artery. Electrically emulating a conventional fluidic transducer uniquely allows a fiber optic pressure sensor to be used with a wide variety of existing physiological patient monitors without modification of those monitors. Systolic, diastolic, and mean blood pressure values are also displayed directly on the BPM every four seconds.

Background and Overview (3400)

Fiber optic pressure transducers are extremely accurate and, when placed in an artery, provide high fidelity, real time blood pressure information to a clinician. Specifically, medical personnel such as cardiologists, vascular surgeons, anesthesiologists, neurosurgeons, interventional radiologists, trauma physicians, emergency medical technicians, etc. all need accurate real time indications of a patient's arterial blood pressure during critical care situations.

The BPM enables the use of modern fiber optic pressure transducer measurements to be interpreted and displayed. The BPM can also be used in a standalone mode where no connection to other equipment is necessary to measure and display blood pressure values in real time.

Figure 34:
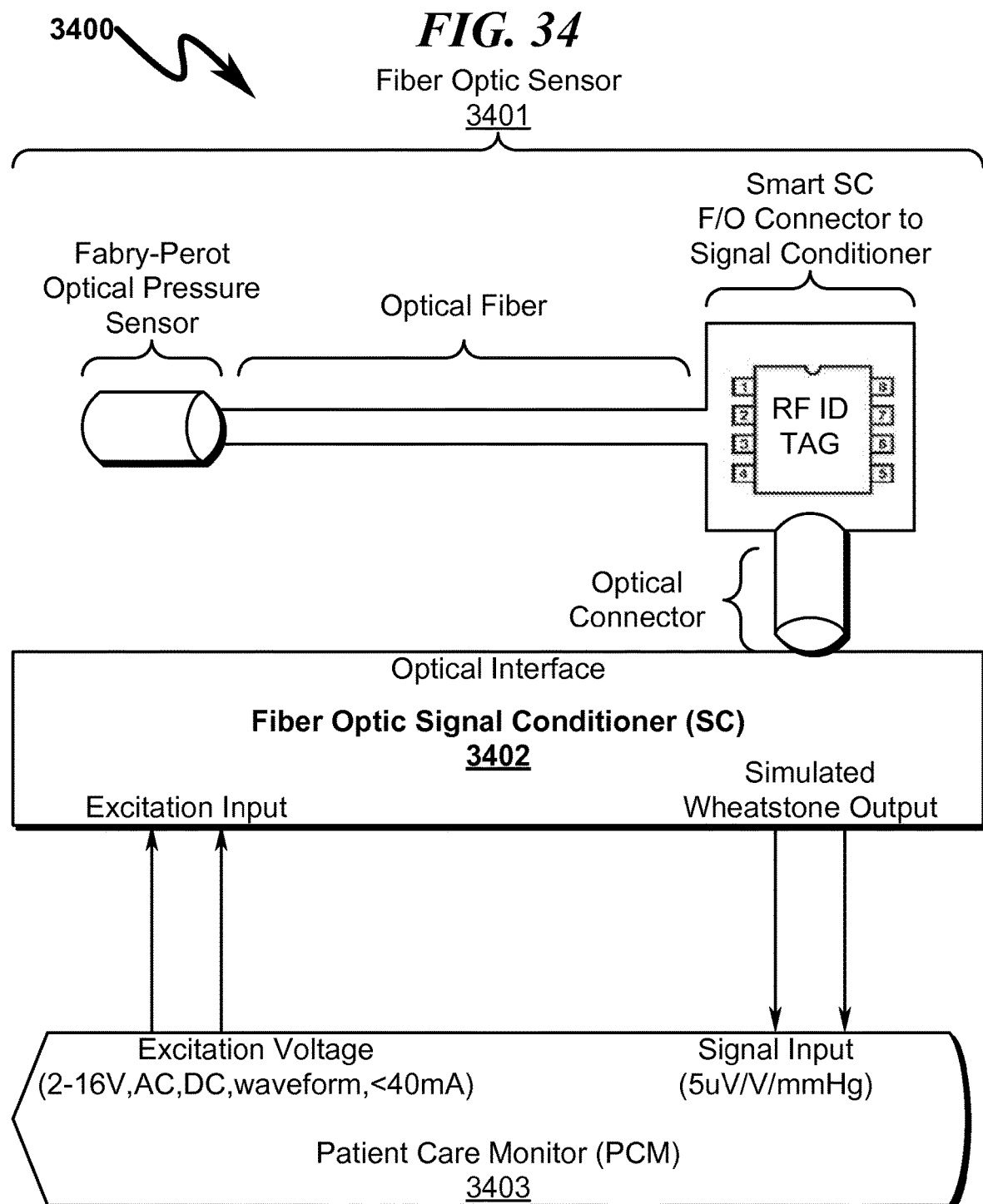
FIG. 34 illustrates a fiber optic pressure sensing system as described by an exemplary product requirements document detailing the construction of a preferred exemplary embodiment of the present invention as applied to a blood pressure monitor (BPM) system.

FIG. 34 (3400) generally illustrates the basic components of a fiber optic blood pressure monitoring system. The figure schematically shows the basic components of a fiber optic pressure transducer assembly. It consists primarily of three parts. One part is a pressure sensitive diaphragm mounted at the distal end of a Fabry-Perot (F-P) cavity which is the transducer itself. Pressure induced deflections of this diaphragm modulate light shining on it and reflect the light down the fiber optic cable which is the second part. The third part is a fiber optic connector that connects to a signal conditioner and contains a non-volatile memory holding transducer-specific gauge factors, an atmospheric correction factor and/or other relevant information.

RJC Fiber Optic Measurement System (FOMS) (3500)

Figure 35:
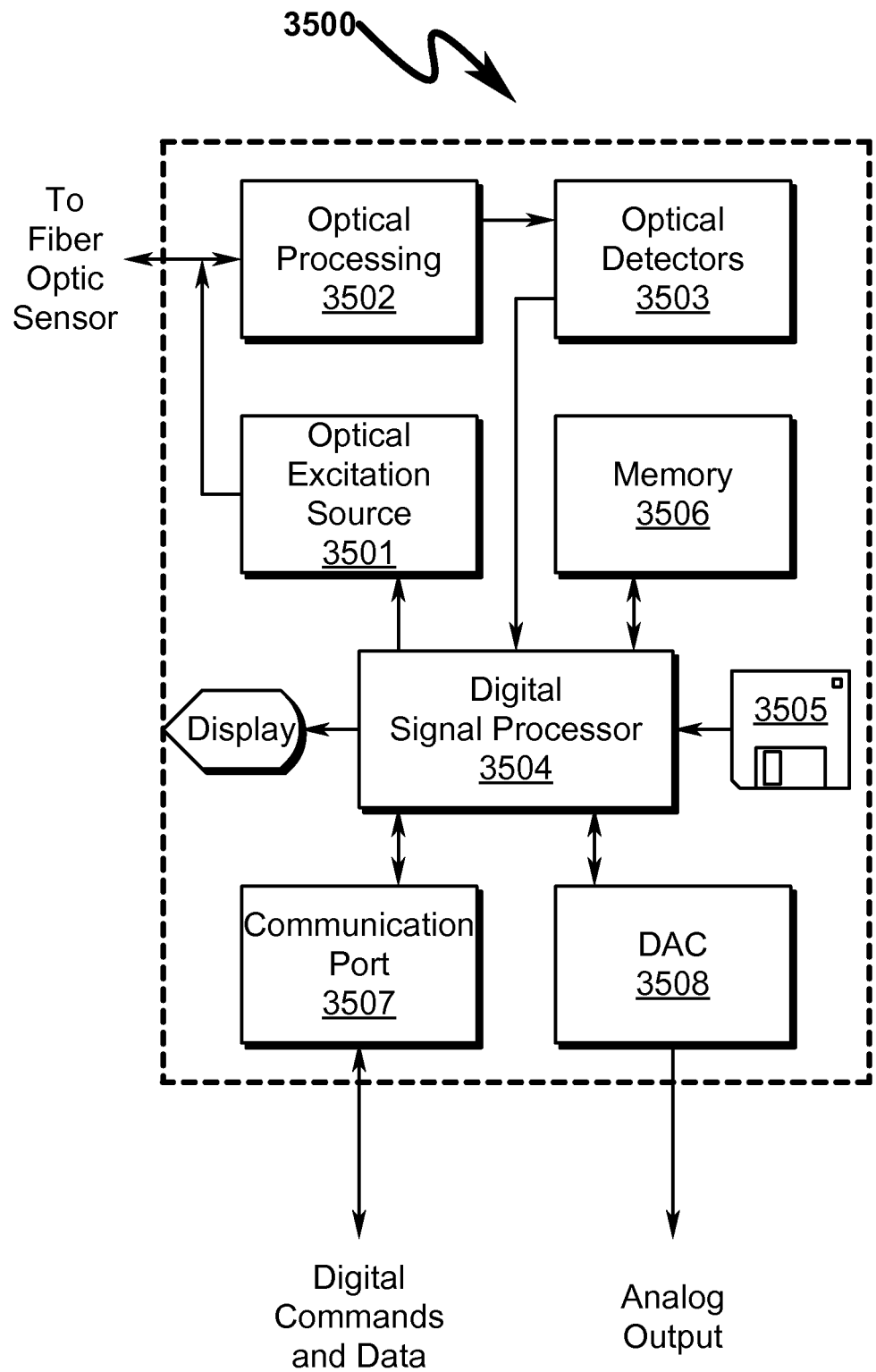
FIG. 35 illustrates a fiber optic measurement assembly as described by an exemplary product requirements document detailing the construction of a preferred exemplary embodiment of the present invention as applied to a blood pressure monitor (BPM) system.

An RJC Fiber Optic Measurement System (FOMS) (available from RJC Enterprises, LLC, 11711 North Creek Pkwy S, STE D-103, Bothell, WA 98011) is the basis for the BPM. FIG. 35 (3500) generally illustrates a schematic block diagram of one instantiation of an electro-optic signal conditioning device that excites a fiber optic F-P pressure transducer and processes the reflected light into an electrical signal proportional to the physiological pressure on the transducer. The FOMS optical module processes the reflected light to produce signals that represent the pressure-induced deformation of the F-P transducer cavity. This processed optical signal is then converted to an electrical signal that is stored in a digital memory for subsequent processing. The FOMS microprocessor processes the digital pressure data and converts it to a format compatible with a serial digital output and/or supplies the data to a digital-to-analog converter that produces an analog patient monitor signal output. The power electronics block converts a single primary power input into multiple voltages needed by the various components in the BPM.

The BPM automatically reads, identifies and configures itself to adapt to the unique characteristics of each fiber optic transducer as well as provides an indication of the integrity of the transducer readiness. It senses internal system status and activates indicators that track its condition.

The BPM incorporates human interfaces that provide information and control functions. Among these functions are:
- an electronic display capable of showing maximum systolic, minimum diastolic, and mean arterial blood pressure readings as well as system status; and
- an automatic zeroing function to adjust to atmospheric pressure when the transducer is connected to the BPM prior to the insertion of the device into a body cavity of a patient.

Exemplary RFID TAG Memory

While many different forms of non-volatile memory may be used in conjunction with the BPM transducer, EEPROM memory and RFID TAG memory are currently considered optimal. One skilled in the art will recognize that a wide variety of EEPROM memory devices may be suitable in this application. The Datalogic/EMS LRP108I RFID TAG used in conjunction with a Melexis MLX90121 RFID transceiver is currently considered an optimal RFID TAG selection for this application. This RFID TAG configuration is available in both a PCB and encapsulated version and utilizes an internal INFINEON chip set.

Conventional Fluidic Arterial BPM Transducer (3600)

Figure 36:
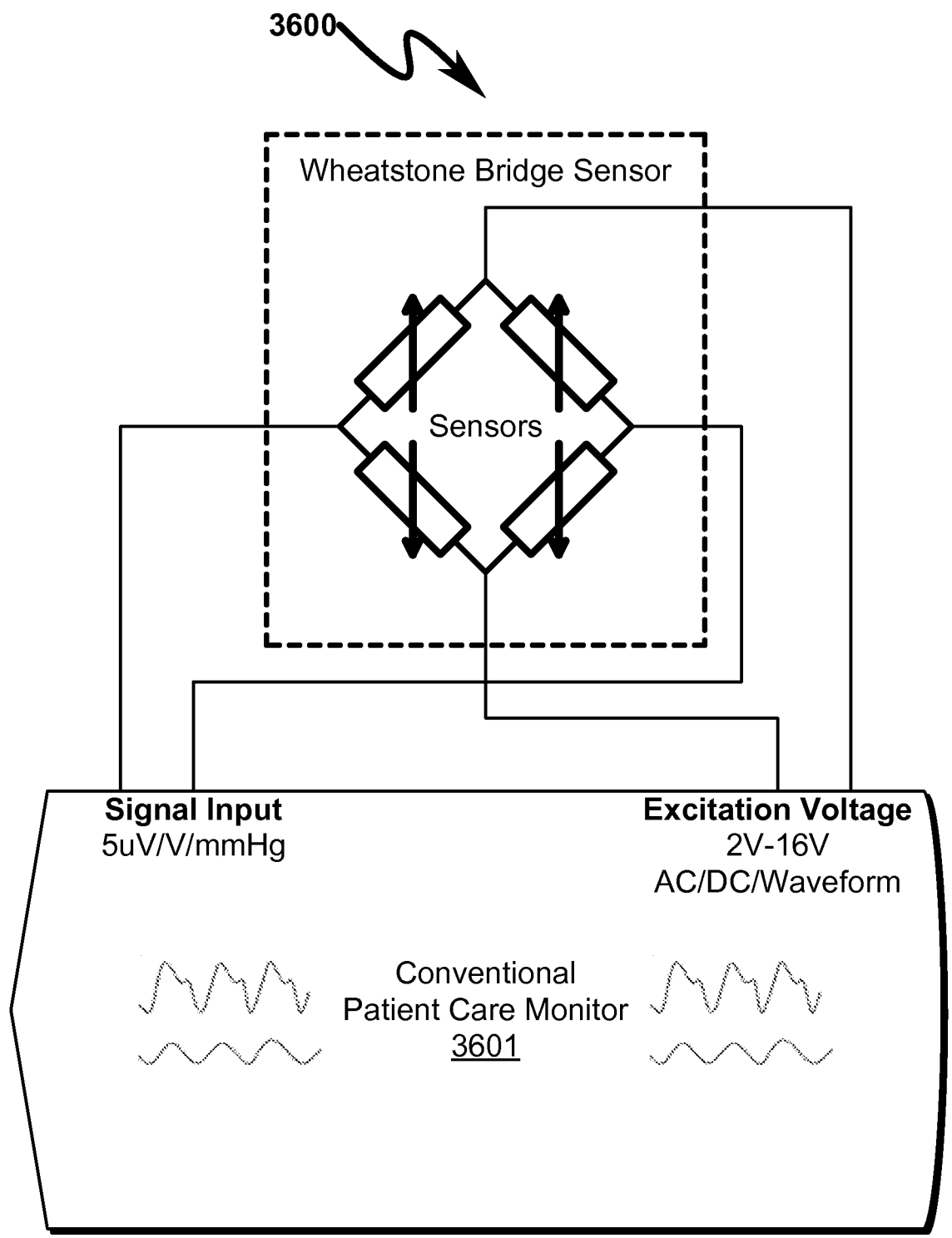
FIG. 36 illustrates a conventional patient monitoring system as described by an exemplary product requirements document detailing the construction of a preferred exemplary embodiment of the present invention as applied to a blood pressure monitor (BPM) system.

A conventional fluidic arterial blood pressure transducer uses a Wheatstone bridge circuit where the legs of the bridge circuit incorporate resistive or strain gauge elements as shown in FIG. 36 (3600). An excitation voltage is applied by a conventional invasive arterial blood pressure patient monitor to the input of the bridge to provide an energizing voltage and a reference for the output signal. When pressure is applied to the transducer, the bridge becomes unbalanced and creates a small analog signal that is directly proportional to the pressure activated change in the transducer resistances. The most common sensitivity value for these transducers is 5-microvolts/volt/mmHg. Although the sensitivity value is reasonably standard in the industry, various manufacturers of patient monitors use a variety of excitation voltages. The BPM supports an adaptive Wheatstone bridge emulation function that senses the instantaneous excitation voltage from the patient monitor to which it is connected. It then automatically applies corrections to the fiber optic pressure transducer signal to scale it to the appropriate values needed by the specific patient monitor.

Exemplary BPM implementation (3700)

Figure 37:
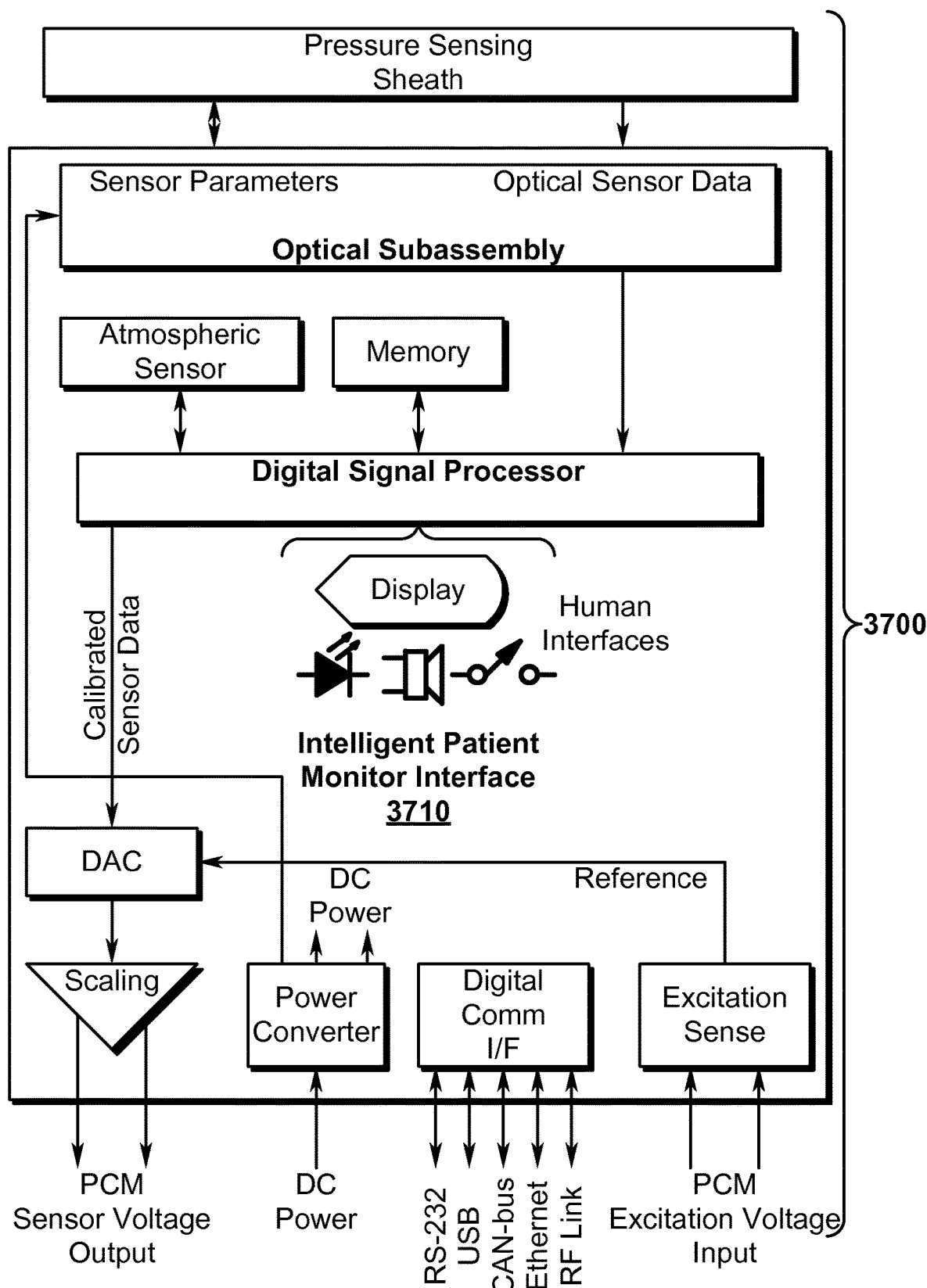
FIG. 37 illustrates a BPM conceptual block diagram as described by an exemplary product requirements document detailing the construction of a preferred exemplary embodiment of the present invention as applied to a blood pressure monitor (BPM) system.

FIG. 37 (3700) generally illustrates a diagram of the major components of an example BPM implementation including the signal conditioner and the conventional patient monitor described previously. However the Wheatstone bridge transducer is now replaced by a connection to the fiber optic interface.

Functional Requirements

High Level Platform Requirements

Function Summary

The following is a high level summary of functionality that is described in more detail later in this document.
- The BPM shall electrically and mechanically interface with standard invasive arterial blood pressure connections to a wide variety of commercial patient monitors.
- The BPM shall accept an excitation voltage from a standard patient monitor and deliver a correspondingly derived optically-sensed blood pressure signal to the patient monitor through an external connector. The interface will emulate the electrical characteristics of a common fluidic arterial blood pressure sensor.
- The BPM shall support a single (1) channel of fiber optic blood pressure data.
- The BPM shall continuously calculate the maximum systolic, minimum diastolic, and mean blood pressure sensed over consecutively repeating four (4) second intervals. The results shall be displayed using the same 4-second sample period for each value in the display format "xxx/yyy" where x represents the systolic reading, and y represents the diastolic reading. The calculated mean arterial pressure "zzz" shall be displayed immediately beneath the systolic and diastolic values.
- The BPM shall have an automatic pressure calibration capability to give a zero pressure reading after compensating for local ambient air pressure.
- The BPM shall derive power from an external primary power supply attached to a standard utility wall outlet.
- The BPM shall have an audible and visual alarm indication that is activated when the Alarm Mean Arterial Pressure (AMAP) value falls below a fixed threshold value of 60 mmHg (low blood pressure alarm threshold).
- The BPM shall have an automatic alarm indication of a failed or absent pressure sensor.
- The BPM shall automatically compensate for any temperature related data dependencies. This compensation shall be effective over the full operating temperature range of the BPM.
- The BPM shall automatically read and adjust for pressure sensor specific data (gauge factors and stored zero factor) from a factory programmed electronic storage device (EEPROM) mounted on the pressure sensor connector. The EEPROM shall store a means of determining whether the PSS and the current BPM to which it is connected have been zeroed together before or not.
- The BPM shall allow factory software updates to be downloaded and verified from an external computer.

Performance Summary

The following is a general summary of BPM performance parameters that are described in more detail later in this document.
- The BPM shall initialize and be ready to acquire a zero value within 5 minutes of power on.
- The BPM shall stabilize enough to achieve all required BPM specifications within five (5) minutes of power on at an ambient temperature of 23° C. (73.4° F.)

The BPM shall support a fiber optic pressure transducer sampling rate of 1000 samples per second.

The BPM shall provide accurate output pressure data between 0 and 300 mmHg

The BPM shall have an internal resolution of at least 0.5 mmHg

The BPM shall provide an accuracy of ±4 mmHg or ±4% of reading whichever is greater.

The BPM shall support real time data processing required to acquire pressure sensor data measurements, convert pressure values to mmHg, and generate maximum systolic, minimum diastolic, and mean arterial blood pressure values over 4-second intervals continuously.

Components and Subassemblies
Fiber Optic Measurement Assembly (FOMA) (3800)

Figure 38:
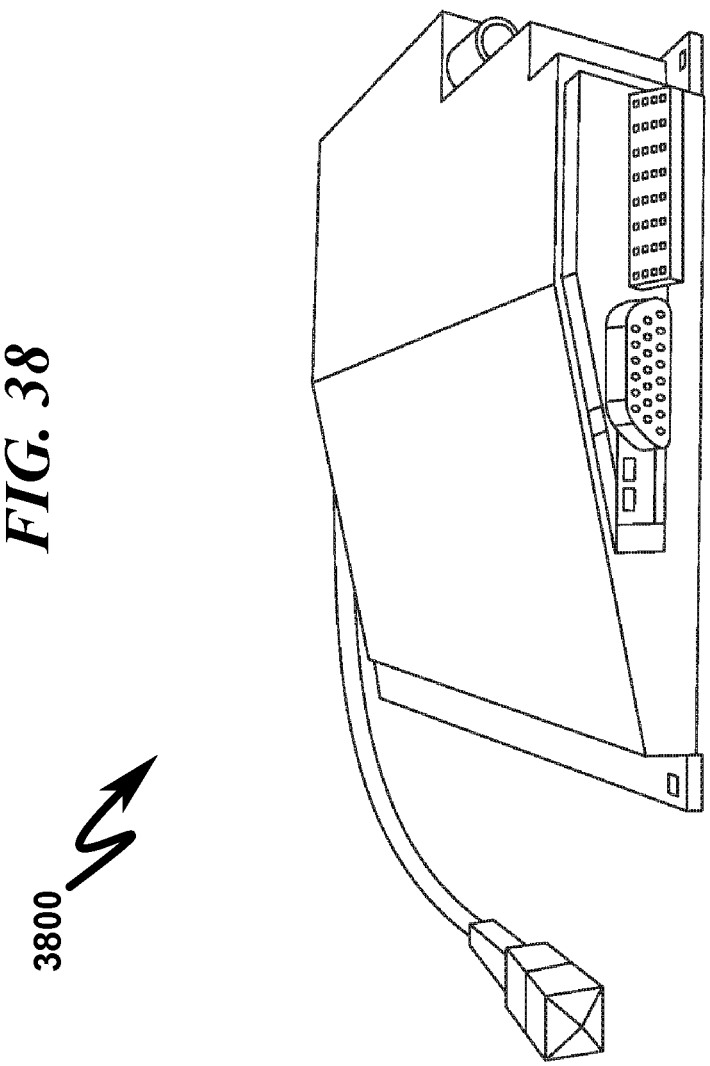
FIG. 38 illustrates an unmodified FOMA signal conditioner as described by an exemplary product requirements document detailing the construction of a preferred exemplary embodiment of the present invention as applied to a blood pressure monitor (BPM) system.

The BPM shall use the RJC FOMA signal conditioner product as the basis for the BPM design. The BPM's primary function is to convert the optical pressure sensor data stream into appropriate electronic signal for display and interface of systolic, diastolic, and mean blood pressure values. The FOMA standard product design shall be modified to achieve the requirements in this document. A general mechanical view of a typical FOMA standard product design is generally illustrated in FIG. 38 (3800).

The signal conditioner has the responsibility for achieving the required specifications for pressure data signal quality at its outputs. The remainder of the BPM functions shall not degrade that quality insofar as the necessary mathematical algorithms allow.

Signal conditioner specifications (unmodified):
Number of channels: 1
Sampling rate: 1-4096 Hz
Communications interface: analog (−0.5 to 3.0 VDC, 10 mV/mmHg) & digital (RS232 & USB) Input voltage range: +8 to +16 VDC, +12 VDC±5% (nominal)
Maximum input current (startup): 2070 mA at 12 VDC
Maximum input current (nominal): 290 mA at 12 VDC
Internal voltage regulation: self-regulated from primary power supply
Input power (startup): 25 W Input power (nominal): 3.5 W
Dimensions: <160 mm×<130 mm×<30 mm (approximate) Weight: <400 gm
Storage temperature: −40° C. to 70° C. Operating temperature: 15° C. to 40° C. Humidity: 0-95% non-condensing
Ambient pressure sensing range: 500-800 mmHg
Integrated thermal control: yes
Sensor optical connection: EC connector
Sensor parameters: read from an RFID tag or Datakey Interface Requirements
Data and Signal Interfaces The data and signal interfaces to the BPM shall be user-friendly and tolerant to the clinical environment. The BPM shall have the following signal interfaces described below.

Ambient Air Pressure Sensor

The BPM shall incorporate an embedded ambient air pressure sensor (manometer). The internal manometer shall be used to correct the PSS sensor pressure values for changes in ambient atmospheric pressure.

Fiber Optic Pressure. Sensor Interface

A fiber optic sensor will be incorporated into a disposable blood pressure sensing sheath (PSS) intended for introduction into a human artery. The fiber optic transducer is embedded into the sheath and exits the sheath as a single fiber optic cable. This cable is terminated in an EC-type fiber optic connector. However, the EC connector is modified to include a passive RFID tag that retains specific information unique to that sensor assembly (gauge factors, null, etc.). This device shall be mounted externally on the sensor connector to communicate with the BPM. The corresponding BPM EC socket must securely mate with the sensor optical and RFID interfaces. After this connection is made, control and signal processing are determined by the BPM. The selection of this connector design shall be done in close cooperation with the pressure sensing sheath design. Cleanliness of this connector is very important, thus a means of protecting the connector when not in use shall be used. A suggested method for accomplishing this is to use press-fit flexible silicone rubber tethered cap.

Patient Monitor Interface (3900)

The BPM shall accept standard analog invasive arterial blood pressure fluidic strain gauge connections from a wide variety of commercial patient monitors. The BPM shall accept an excitation voltage from the patient monitor and deliver a correspondingly derived optically-sensed blood pressure signal to the patient monitor through an external connector. The interface shall automatically detect the presence of a patient monitor and adjust its output based on the sensed excitation voltage applied. The interface will electrically emulate a common fluidic invasive arterial blood pressure transducer interface.

This interface shall be continuously active at all times after the BPM has successfully completed initialization. During periods when blood pressure sensor data is not being acquired from a fiber optic sensor, the signal output shall be zero (0) mmHg.

The following patient monitor interface characteristics shall be accepted or achieved by the BPM:

Excitation input voltage range: 0 to +8 Vrms
Excitation voltage frequency range: DC to 5000 Hz
Excitation load impedance: >200 ohms (350 ohms, ±5%, nominal)
Output sinusoidal phase shift: <5°
Output sensitivity: 5 uV/V/mmHg
Output impedance: <3000 ohms, (350 ohms, ±5%, nominal)

The fiber optic sensor pressure signal delivered to the patient monitor through this BPM analog interface shall have the following characteristics. Although some of these parameters are dependent on the characteristics of the sensor, the BPM must maintain these specifications when connected to a conforming sensor.

Figure 39:
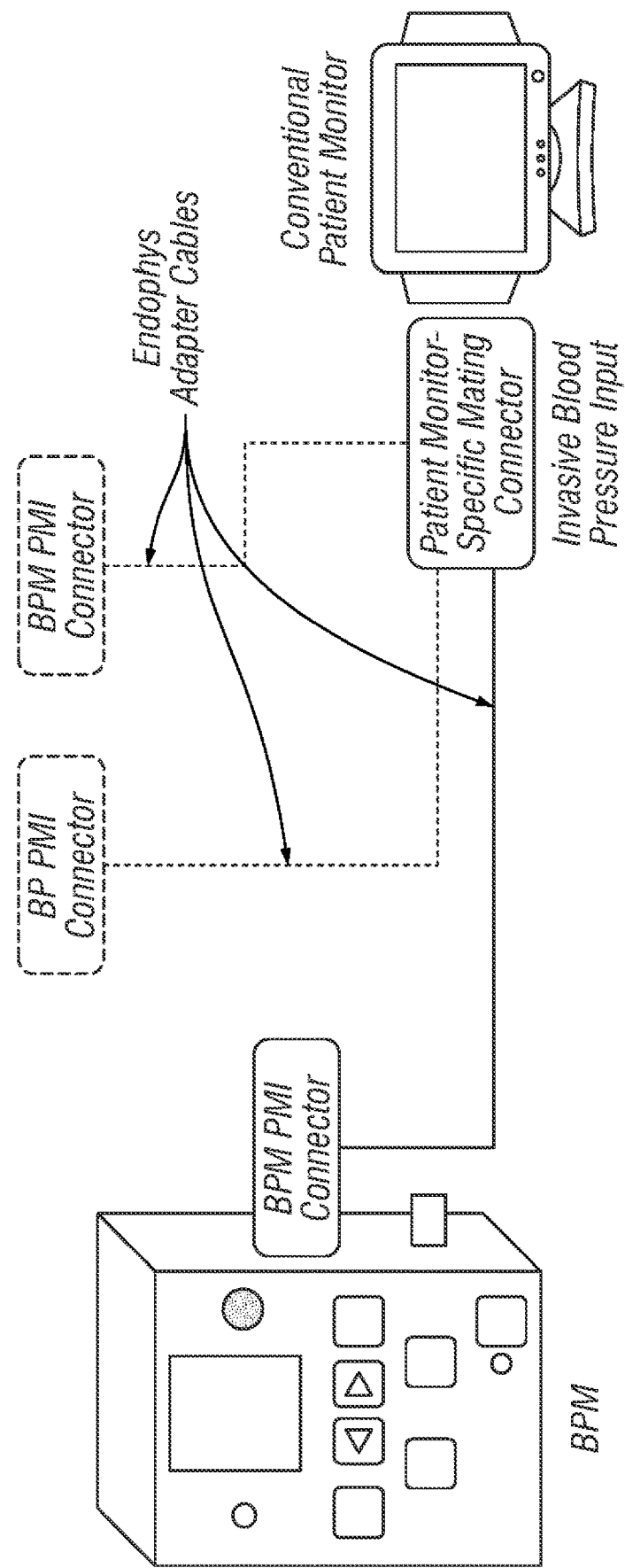
FIG. 39 illustrates exemplary patient monitor cabling as described by an exemplary product requirements document detailing the construction of a preferred exemplary embodiment of the present invention as applied to a blood pressure monitor (BPM) system.

Pressure range: 0 to 300 mmHg
Resolution: 0.5 mmHg
Accuracy: ±4 mmHg or ±4% of reading whichever is greater.
Thermal drift: ±2 mmHg/within 1 hour after 5-minute warm-up As generally illustrated in FIG. 39 (3900), the BPM case shall have a single patient monitor interface (PMI) connector that shall physically and electrically mate with a reusable interface cable that connects to the fluidic invasive pressure transducer connection on a conventional patient monitor. This will be done using an adapter cable converting the BPM case mounted connector to a vendor-specific, invasive fluidic transducer patient monitor interface connector. The present invention anticipates BPM adapter cables for use in interfacing to a variety of patient monitors. These cables are considered independent PSS system elements. These cables will initially support patient monitors manufactured by General Electric Health Care Systems and Phillips Health Care Systems.

USB 1.x/2.0 Communications

The BPM shall provide one (1) external USB 1.x/2.0 communications port. Both 1.x and 2.0 USB communications shall be supported. Five volt (+5 VDC, 500 mA) power shall be supplied through this interface for external use according to industry standards. A USB standard B receptacle shall be provided on the outside of the PMI case for this interface.

External Data Acquisition and Control

The PMI shall support real time communications with an external computer through the USB communications interface. The BPM shall automatically sense the presence of, and respond to, an external computer connected to the USB communication port. The port shall have the ability to communicate with an external computer equipped with a standard USB 1.x/2.0 communications port. This communications port shall be normally accessible to users.

After BPM initialization, the external USB port shall continuously stream full resolution real time digital pressure data at the sensor sampling rate (1000 samples per second) to an attached computer whether a PSS is present or not. The data stream shall reflect the same atmospherically corrected blood pressure values used in calculating the display values. If the BPM detects an invalid blood pressure value, that value shall be included in the data stream. It shall be the responsibility of the data acquisition computer to capture and filter the data stream as it becomes available from the BPM.

After successful power-on initialization but prior to establishing the connection of a healthy PSS, the BPM shall output a stream of artificial zero (0.0 mmHg) pressure values unless interrupted by higher priority internal processing activities. After connection of a healthy PSS, and the start of acquisition of atmospherically compensated pressure data (either using a current zero or pre-zero) the BPM shall initiate streaming of sensed PSS pressure data values. If a healthy PSS is disconnected from the BPM while acquiring pressure data, the output stream shall revert to a pressure value of zero (0.0 mmHg) until a healthy PSS is connected and zeroed.

When values (either zeros or acquired pressure) are streaming from the USB port and an interruption of that sequential data occurs, a single instance of the value minus 99x (−99x) shall be prepended to the first sample of any new data stream to indicate that a prior interruption of the new sequence has occurred. The value "x" is a numerical character 0-9 that may be optionally used for factory diagnostic purposes. The default value of "x" is nine (9) if no other optional values are used.

Factory Maintenance Communications

The BPM shall have a privileged maintenance capability that will respond to external computer control instructions that perform various maintenance activities. Details of these functions appear later in this PRD under the Maintenance section.

Internal Clock

The BPM shall employ an internal clock with a resolution capable of generating a display update period of 4-seconds.

Human Interfaces,

The human interfaces to the BPM shall be user friendly and tolerant to the clinical environment. More detailed operation of these indicators and alarms can be found in the accompanying document entitled BPM High Level Functional Logic Diagram.

Visual Indicators

The BPM shall provide visual indicators as described below. Each full display screen shall have at least 0.5-second duration.

Initialization Status

The BPM shall indicate "POWER UP" on the display immediately after a power on is initiated. After successful completion of the basic initialization sequence, the BPM shall display the message "WARMING UP" until the BPM has reached a thermally stable state where all its performance characteristics are satisfied.

The BPM shall indicate "NO SENSOR" on the alphanumeric display when a PSS is not connected. The BPM shall display "SENSOR ERROR" when it detects a defective PSS.

Low Blood Pressure Alarm

A red LED on the front panel shall illuminate when the low blood pressure alarm is triggered by an Alarm Mean Arterial Pressure (AMAP) value less than the low blood pressure alarm threshold of 60 mmHg. The low blood pressure LED alarm shall extinguish when the AMAP value has returned to a value equal to or above the alarm threshold set value. In the event of a simultaneous "Sensor" alarm and a Low Blood Pressure alarm, the "Sensor" alarm will take priority on the display.

Zero Status

Upon connection of a PSS, or after the initialization of the BPM is complete with a PSS already connected, the BPM shall check the health of the PSS, display "ZEROING", and determine whether the PSS has been zeroed with the currently connected BPM before by interrogating the PSS RFID tag. If the check indicates the PSS has not been zeroed on the BPM, then the process will proceed to check for a stable PSS pressure measurement for 5-seconds. The intent of this check is to automatically determine if the PSS sensor is exposed to ambient atmospheric pressure or is instead placed in a live patient.

If the PSS pressure is stable, the BPM shall automatically calculate the appropriate atmospheric compensation zero value. Stable (or static) pressure in this context is defined by 50 sequential pressure samples taken at 0.1 second intervals for a contiguous 5 second period deviating from each other by no more than 0.5 mmHg. After achieving a zero, the BPM shall proceed to store the zero value in the PSS RFID tag and BPM memory, store a value in BPM memory indicating that the PSS has been zeroed on the particular BPM, display "ZEROED", and then begin displaying blood pressure values every 4-seconds.

If the PSS pressure is fluctuating, and the BPM reads a stored PSS RFID tag value that indicates a valid zero has never been achieved with the PSS, the BPM shall display "PRESSURE VARIES" and repeatedly attempt to generate a current zero value by waiting for a continuous 5-second period of static PSS pressure until successful. After achieving a zero the BPM shall proceed to store the zero value in the PSS RFID tag and BPM memory, and begin displaying blood pressure values every 4-seconds.

Alternatively, if the PSS pressure is fluctuating and the BPM reads a stored PSS RFID tag value that indicates a valid zero has previously occurred for that PSS at some other time, the BPM shall display a "PRE-ZERO USED" message, a warning icon, as well as sound an audible alarm indicating that the BPM is using a zero value obtained at an earlier time. The "PRE-ZERO USED" message shall be removed from the display and the audible alarm silenced when the ensuing first 4-second blood pressure values are displayed. However the warning icon shall remain on the display until the currently attached sensor is removed or the BPM performs a subsequent successful zero operation, after which it will extinguish in either case.

If an invalid zero value is read, the BPM shall display "SENSOR ERROR".

Display

The BPM shall incorporate an alphanumeric display on the front panel. The display shall have the following characteristics:

Technology: low power, transreflective, 128×64 pixels, chip-on-glass (COG) LCD.

Overall display size: as large as necessary to accommodate the character matrix.

Display color: black characters on a white background.

Display characters: two (2) lines of at least 8 alphanumeric characters or acceptable equivalent functionality. The characters shall also be capable of displaying a forward slash ("/") delimiter and an Alarm Mute icon, or acceptable equivalents.

Character size: Upper case characters shall be no less than 0.96 cm high.

Back light: Back lighting is required. Back lighting shall always be active while the BPM is turned on.

Orientation and layout: The display shall show a continuous and simultaneous visual indication of systolic, diastolic, and mean blood pressure.

The pressure readings shall each continuously show the three (3) most significant integer digits of each reading in whole units of mmHg unless otherwise indicated below. No fractional digits are required.

If a displayed pressure value is non-zero, any leading zero(s) [more significant than the left-most non-zero character] shall be suppressed and not displayed.

If a displayed pressure value is zero, a single zero (0) shall be displayed.

The systolic reading shall be displayed to the left of the diastolic reading. These values shall be separated by a forward slash character ("/") and be immediately adjacent to the slash character.

The displayed mean arterial pressure (DMAP) reading shall display centered immediately below the systolic and diastolic readings.

Alarm functions: The display shall support an icon indicating when the Alarm Mute function is activated.

Horizontal viewing angle: within 40° off axis.

Each 3-digit blood pressure display value position shall be labeled with its respective description on the front panel.

The display will be optimally positioned on the front of the case to be easily observed by the operator. It will be placed in an optimized ergonomic location to minimize interference with manual operation of controls.

Switches & Controls

Power On-Off Switch

The BPM shall have a single button push-on/push-off power switch. The switch shall be ergonomically placed on the front panel. The switch shall typically be of the membrane type.

Power on activation shall start a hardware and software initialization sequence from a powered down condition. Software initialization shall not require more than ten (10) seconds to complete. Hardware initialization shall not require more than 5-minutes to reach a full operational state. Power off activation shall discontinue all current activities, initiate a power down sequence to gracefully shut down the BPM and extinguish any indicators and displays.

The switch shall be clearly labeled with the generally recognized international power on-off symbol as well as a "Power" label on the panel below it.

Audible Alarm Mute

The BPM shall provide a single membrane type push-on/push-off switch on the front panel to mute alarm sounds while continuing to allow any visual alarms. Initially depressing this switch shall mute (disable) any audible alarm sounds. Depressing this switch again shall re-enable the ability to hear any aural alarms. This switch shall subsequently toggle between enabling and disabling aural alarm sounds. The initial condition on power up shall be enabled.

Audible Alarms

The BPM shall include four (4) different audible alarms to indicate:

Low blood pressure—when the 4-second AMAP blood pressure value falls below the alarm threshold value of 60 mmHg (low blood pressure alarm);

Sensor—to indicate an absent or failed PSS;

Unstable pressure required for zeroing; or

The required use of a pre-zero value from an earlier successful zero calculation.

The alarm sounds will consist of two (2) distinctly differentiable sounds at a fixed volume level. Each sound will be obviously acoustically distinct from the other. The low blood pressure alarm shall exclusively be distinct from the other alarms. The second distinct alarm sound shall be common to the other conditions.

All audible alarms shall discontinue when the associated parameter has returned to above the threshold alarm value or the alarm has been muted by the operator. The low blood pressure alarm shall discontinue when the 4-second AMAP blood pressure is 60 mmHg. The sensor alarm shall discontinue when a healthy PSS has been connected. The unstable pressure alarm shall discontinue after an attempt to zero a sensor is started. The pre-zero alarm shall be discontinued when the first 4-second pressure values are displayed. In the event of multiple simultaneous alarms the sensor and low blood pressure alarms will take priority in that order. The unstable pressure and pre-zero alarms are mutually exclusive.

Power Requirements

Primary Power Sources (4000)

Figure 40:
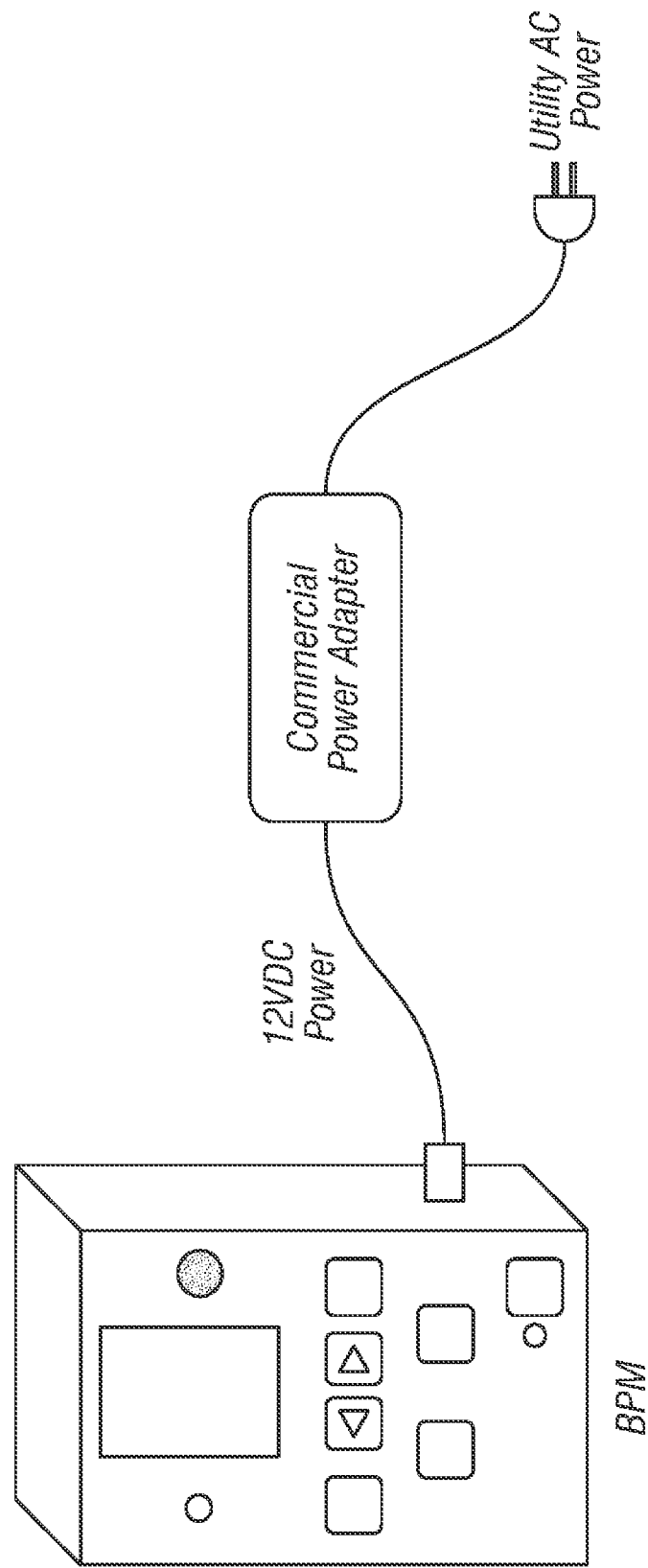
FIG. 40 illustrates a primary power supply as described by an exemplary product requirements document detailing the construction of a preferred exemplary embodiment of the present invention as applied to a blood pressure monitor (BPM) system.

As generally illustrated in FIG. 40 (4000), the system shall use utility AC power for its operation. The BPM shall use an external power adapter that converts utility AC wall power into a single +12 VDC primary voltage required for BPM operation. The AC power adapter and the BPM shall be connected by a cable that is permanently attached at the power module and detachable at the BPM connection. This BPM AC power input connector shall use a standard power connector acceptable to regulatory agencies. It is preferred that the AC power adapter be procured as a prequalified OEM product with multiple sources.

AC Primary Power Supply

The utility based AC primary power supply will consist of an external power adapter that connects to utility AC power and converts it to the nominal +12 VDC primary power input of the BPM. The utility power module will typically have the following minimum characteristics:

Nominal AC input voltage: 100 VAC to 250 VAC

AC input current: <1.8 A

AC input frequency: 50 Hz-60 Hz

DC output voltage: single voltage +12 VDC

DC continuous output current: 3.5 A

DC output regulation: ±5%

AC input connector: USA standard male, 3-blade AC plug, or foreign country-specific plug
AC input cable length: 5 feet (1.5 meters)
Power adapter to BPM cable length: 5 feet (1.5 meters)
OEM power adapter approved for use with FDA Class 2 medical equipment
Dimensions: no greater than 65 mm (W)×125 mm (L)×50 mm (D)
MTBF: ≥50,000 hours
Environmental: shall equal or exceed those of the BPM BPM Internal power Conversion Subsystem The internal BPM power subsystem is responsible for creating and conditioning the separate voltage rails necessary for the internal components. BPM power subsystem input power shall be provided with electrical power from a primary power source with the following characteristics:
Primary input voltage: +12 VDC
Maximum input current: 3.5 A
Maximum continuous input power: 35 W
Primary input regulation: ±5% or better
Sensing: The power subsystem shall have an internal protection capability to:
  Prevent damage to the BPM when the primary source input voltage is not within specifications
  Prevent damage to the primary power supply when an internal failure causes an over-current condition (e.g., fuse)
  Prevent operator safety concerns when a BPM internal failure occurs Initialization and Maintenance
Initialization
Cold Start Initialization The BPM shall automatically initialize upon powering up from an extended power off state and prepare the unit for proper operation. This initialization will execute before any normal operational tasks are started. Under normal circumstances the initialization shall complete in less than 5-minutes from a cold start condition. During initialization the following actions shall be completed when a healthy PSS is connected:
Energize and reset hardware to a known state.
Automatically verify the integrity of the system firmware.
Enable all alarms, and initialize all operational parameters.
Sense and verify the optical module is at the targeted stable temperature before proceeding to execute normal operational functions.
Begin monitoring for detection of a connected PSS.
Display "INSERT SENSOR" if a healthy PSS is not connected.
Detect connection of a healthy PSS.
Read and store the sensor parameters from the PSS in the BPM.

PSS Initialization

The following automatic actions are subsequent to Power On initialization and connection of a PSS. Attaining thermal optics stability at the specified temperature and connection of a PSS shall not require more than ten (10) seconds to complete after the PSS is exposed to a steady ambient atmospheric pressure:
Display "ZEROING" to indicate that a zero function has been initiated.
Determine whether the PSS has been previously zeroed on this BPM.
Detect static ambient pressure for at least 5 seconds.
Calculate and store the zero value in the PSS RFID TAG and BPM memory.
Upon success, display "ZEROED" to indicate the zero function is complete.
Begin acquiring, processing, and displaying pressure samples.

More detailed operation of the initialization sequence can be found in the flowcharts incorporated in the attached FIGURES.

Maintenance
Cleaning

Cleaning of the BPM shall be done using only water, alcohol, and/or mild liquid surface cleaning detergents applied with a damp cloth or equivalent as needed. The BPM is not intended to be submersed or subjected to excessive moisture.

USB Maintenance Interface

The BPM shall have a maintenance capability that will respond to external computer control instructions that perform factory maintenance activities to monitor, verify, or enhance the operational capabilities of the BPM. An external computer shall have the ability to send commands and data between it and the BPM USB communications port. The following functions shall be supported as a minimum:
The BPM shall respond to external computer control instructions that perform maintenance activities to identify, monitor, verify, download and/or upload the software contained in the BPM. An external computer shall have the ability to send commands and data between it and the BPM USB communications port to perform factory manufacturing and maintenance tasks.
The BPM shall respond to RJC FOMA-specific commands by passing these commands and any associated data to and from the BPM external USB communications port interface. This function shall support the RJC FOMA supported commands specifically including all 'Report' and 'Monitor Mode' commands. This function shall allow maintenance access to control and monitor active and static internal information needed by factory maintenance personnel.
The factory maintenance capabilities shall be reserved and protected from user level access. The BPM shall support a maintenance password to gain access to the privileged maintenance commands and information described in this section.

Software Functional Requirements

Identification and Verification

This PRD uses the terms "software" and "firmware" interchangeably to describe any volatile or non-volatile internal instructions available to be executed in support of the BPM functions whether embedded or otherwise. The BPM software shall employ a means for an external computer to identify the specific version of software resident in, or downloaded to, the BPM when accessed via the maintenance port. Each software load shall also employ a checksum to indicate and verify the integrity of the code after it has been downloaded to the BPM.

Applications Supported

A custom embedded application will handle the operation of the BPM. Details of these functions can be found above and the flowcharts detailed in the attached FIGURES. This application will support the following major functionality:
Initialize the system at power on.
Monitor important BPM system parameters.
Perform evaluation of the pressure sensor connection status and integrity.

Acquire and process pressure sensor data.

Calculate and display systolic, diastolic, and MAP blood pressures.

Respond to human interface inputs and internal signals to perform control functions.

Generate required alarms.

Support a remote download capability allowing monitoring and maintenance of the BPM and its firmware through a maintenance communications port.

Support the ability to perform specified diagnostics and report the results.

Shut down the system in an orderly manner when powered off by an operator.

Read and write the PSS RFID TAG.

Algorithms and Definitions

Acquisition Frame Time

Blood pressure data shall be acquired at a 1000 samples per second rate with one sample being continuously acquired every 1 ms. This 1 ms time period represents an acquisition frame time. There is no predefined beginning or end to the data flow as it is a real time continuously streaming process.

Display Frame Time

Blood pressure data shall be continuously acquired and processed during operation of the BPM after successful power-on initialization. Data acquisition shall be partitioned into display frame times with a period of four (4) seconds/frame. The initial display frame shall be started with the first pressure data sample available after commencing acquisition. Each subsequent display frame shall be contiguous with earlier and subsequent display frames. This display frame period shall be repeated continuously throughout data acquisition. Each 4-second display frame time will consist of 4000 each, 1 ms. acquisition frames.

Systolic Blood Pressure

The systolic blood pressure value displayed shall be computed by comparing each valid sequential blood pressure value (calibrated to ambient atmospheric pressure and rounded to the nearest whole mmHg) to the previous highest current display frame value. Limit checking shall be done prior to this computation to determine if the current blood pressure value is between 0 mmHg and 300 mmHg to assure data quality. If the blood pressure value is outside this range, the value shall still be used in this computation. The result of the comparison shall retain the higher of the two values as the new current value. This process iterates continuously until the start of a new display frame occurs, at which time the retained result is displayed and the initial value is reset to zero (0) mmHg. This computation occurs at a data rate of 4000 samples per display frame and is synchronous with the diastolic arterial pressure data processing and display. In no case shall a calculated systolic blood pressure value of less than 0 mmHg or greater than 300 mmHg be displayed, even if the result of the calculation is outside that range. If the calculated result is less than 0 mmHg, then the displayed pressure shall be 0 mmHg. If the calculated result is greater than 300 mmHg, then the displayed pressure shall be 300 mmHg.

Diastolic Blood Pressure

The diastolic blood pressure value displayed shall be computed by comparing each valid sequential blood pressure value (calibrated to ambient atmospheric pressure and rounded to the nearest whole mmHg) to the previous lowest current display frame value. Limit checking shall be done prior to this computation to confirm the current blood pressure value is between 0 mmHg and 300 mmHg to assure data quality. If the blood pressure value is outside this range, the value shall still be used in this computation. The result of the comparison shall retain the lower of the two values as the new current value. This process iterates continuously until the start of a new display frame occurs, at which time the retained result is displayed and the initial value is reset to three hundred (300) mmHg. This process occurs at a data rate of 4000 samples per display frame and is synchronous with the systolic arterial pressure data processing and display. In no case shall a calculated systolic blood pressure value of less than 0 mmHg or greater than 300 mmHg be displayed, even if the result of the calculation is outside that range. If the calculated result is less than 0 mmHg, then the displayed pressure shall be 0 mmHg. If the calculated result is greater than 300 mmHg, then the displayed pressure shall be 300 mmHg.

Mean Arterial Pressure

Displayed Mean Arterial Pressure

The displayed mean arterial pressure (DMAP) shall be the value that is displayed below the systolic and diastolic pressure values on the front panel of every display frame. It shall be computed by adding each sequential blood pressure sample value (calibrated to ambient atmospheric pressure and rounded to the nearest whole mmHg) acquired throughout the current display frame and dividing the sum by the total number of valid pressure data samples in that frame. The value displayed shall be the three (3) most significant integer digits of the resulting quotient, rounded to the nearest whole number. This process iterates continuously until the end of each display frame, after which the initial mean value shall be reset to zero (0). This computation and display process is concurrent and synchronous with the diastolic and systolic pressure data processing and display (i.e., display of the current systolic, diastolic, and mean pressures occur simultaneously after each display frame). In no case shall a calculated systolic blood pressure value of less than 0 mmHg or greater than 300 mmHg be displayed, even if the result of the calculation is outside that range. If the calculated result is less than 0 mmHg, then the displayed pressure shall be 0 mmHg. If the calculated result is greater than 300 mmHg, then the displayed pressure shall be 300 mmHg.

Alarm Mean Arterial Pressure

The alarm mean arterial pressure (AMAP) shall be the value which is compared to the low blood pressure alarm threshold at the end of every display frame, however AMAP is not displayed. It shall be computed by adding each valid sequential blood pressure sample value (calibrated to ambient atmospheric pressure and rounded to the nearest whole mmHg) acquired throughout the two (2) most recent display frames and dividing the sum by the total number of pressure data samples in those frames. The value computed shall be the three (3) most significant integer digits of the resulting quotient, rounded to the nearest whole number. This process iterates continuously at the end of each display frame, after which the initial mean value shall be reset to zero (0) mmHg. This computation and threshold comparison process is concurrent with the diastolic, systolic, and displayed mean arterial pressure data processing and display (i.e., display of the current systolic, diastolic, and mean pressures, and alarm threshold comparison occurs simultaneously after each display frame).

Automatic Atmospheric Pressure Compensation

After BPM initialization and upon connection of a pressure sensing sheath, the BPM shall execute an automatic "zero" or "null" function that will measure the ambient atmospheric pressure and subsequently apply any necessary compensation to the connected input sensor pressure data to achieve the required BPM accuracy. This function shall be done while the PSS sensor is exposed to the same static ambient atmospheric conditions as the BPM (before introduction into a patient). The resulting pressure compensation parameter(s) shall be retained in the RFID TAG memory of the currently attached PSS and the BPM memory so that if the sensor is accidentally disconnected from the BPM during a clinical procedure, reconnection of the same sensor shall not require re-exposure of the sensor to stable ambient atmospheric conditions for recalibration. This function is separate from the nominal initialization sequence and shall not require more than ten (10) seconds to complete. This function is not included in the overall Power On activation time requirement since a pressure sensing sheath may not be connected to the BPM at Power On.

Alarm Pressure Threshold

The BPM low blood pressure alarm threshold shall be fixed at a value of 60 mmHg at the factory. This parameter is not user adjustable. It is the value with which the alarm mean arterial pressure value is compared to determine whether the low blood pressure alarm should be triggered or not.

FOMA Commands

The BPM shall respond to selected RJC FOMA-specific commands by passing these commands and any associated data to and from the BPM maintenance port interface.

Physical Requirements

Mounting

The BPM shall be designed to mount onto a vertical, polished metal, cylindrical pole such as an IV stand. This requirement may be accomplished by using an external mounting device.

Front Panel

Preferred placement of indicators, controls, and display shall be determined during the design process in close cooperation with field testing to optimize clinical effectiveness.

Case

Suitable mounting points for attaching external mounting hardware to the BPM to accommodate the specified mounting requirements shall be designed into the case. Mounting hardware suitable for attaching the BPM to the IV pole described above shall be included in the design, preferably using a readily available OEM device. Alternative mounting approaches may be adopted in cooperation with UTSW to optimize clinical effectiveness. The color of the case shall be off-white or other ergonomic color selection.

Physical Placement of Human Interface Devices

Detailed placement of indicators, controls, and connectors shall be determined during the design process in close cooperation with field testing feedback.

The front of the case shall be defined by the location and orientation of the front panel display. General locations for external components shall be as follows unless agreed otherwise:

LCD display: front
    Manual controls: front
    Fiber optic cable EC connector: lower left side. A tethered cover shall be provided for this connector for use when the connection is not needed.
    Primary power input connector: lower right side.
    Patient monitor connector: middle right side.
    External USB connector: upper right side. A tethered cover shall be provided for this connector for use when the connection is not needed.

Size

The BPM case will not exceed 200 mm (L)×120 mm (W)×70 mm (D) exterior dimensions, including any protective shroud or boot, but excluding any mounting device. A reasonable area will be reserved on the back of the case for labeling.

Weight

The goal is to minimize the weight of the BPM. The total weight of the BPM shall be less than 700 grams, but there is no need to add extra product cost to attain this goal unless the weight exceeds 1000 grams (excluding primary power supply).

Labeling

Labeling shall be sufficient to satisfy regulatory and certification agency requirements. In addition to those requirements minimal labeling will consist of:

Company name
    Model number
    Serial number
    Country of origin
    Applicable patents
    Certification symbols Accessibility of Interfaces Human and electrical interfaces functionally accessible from outside of the Interface shall be:

Switches and controls
    Fiber optic PSS sensor connector
    Alphanumeric display
    External power connector
    External USB connector
    External patient monitor connector Accessibility of these items will be designed primarily with ease of use as a priority. No user serviceable components are internal to the BPM, so no internal access is required other than for factory level maintenance.

Accessibility and Maintenance

No user serviceable components are internal to the BPM, so no internal access is required other than for factory level maintenance.

Connectors

All external connections to the BPM shall utilize connectors conforming to medical application and regulatory requirements.

Environmental Requirements

Storage Temperature

The BPM non-operating storage temperature will withstand from −40° C. (−40° F.) to 65° C. (149° F.) without causing degradation or failure when subsequently operated within the specified operating temperature range.

Operating Temperature

The BPM will operate continuously in ambient air temperatures from 15° C. (59° F.) to 35° C. (95° F.) without degradation or failure. The BPM internal temperature shall be controlled to keep the signal conditioner optics within its operating temperature specifications.

Humidity

The BPM will operate in a humidity range of 5%-95% relative humidity (RH), non-condensing, without degradation or failure.

Altitude and Atmospheric Pressure

The BPM will operate within an altitude range from sea level to 10,000 feet without degradation or failure. There is no requirement to operate in a hyperbaric chamber.

Case Protection and Integrity

The BPM does not have hermetic sealing requirements. The BPM may employ a separate protective shroud if necessary to attain the characteristics required to meet the mechanical shock and vibration specifications.

Cleaning and Sterilization

There are no sterilization requirements. The BPM must be able to be superficially cleaned using common surface disinfectants without suffering cosmetic or functional damage. The BPM shall minimally withstand surface cleaning with isopropyl alcohol.

Mechanical Shock

The BPM shall withstand a 36-inch drop onto a tile or concrete floor on any axis, edge, or corner without shattering or otherwise becoming a serious personnel hazard.

Vibration

The BPM must withstand vibration that will be experienced during normal shipping.

Magnetic Fields

The BPM is not required to operate in a high magnetic field environment (e.g., MRI room). Hence, no extraordinary magnetic shielding is required.

Electromagnetic Compatibility

The BPM shall comply with the appropriate EMC radiation, conduction, and susceptibility requirements imposed by the Federal Communications Commission or other authorities for the device class of the BPM system.

Ionizing Radiation

No radiation shielding is required.

Chemical Resistance

Brief (less than 5 minutes) contact immunity to most common mild liquid cleaning and disinfection chemicals and materials is required. The BPM shall minimally withstand surface cleaning with isopropyl alcohol.

Transportation Requirements

The BPM shall be shipped in a protective container. It shall not experience damage under normal shipping conditions.

Pressure Selection/Analysis/Sampling and Display

Conventional Blood Pressure Display (4100)

Figure 41:
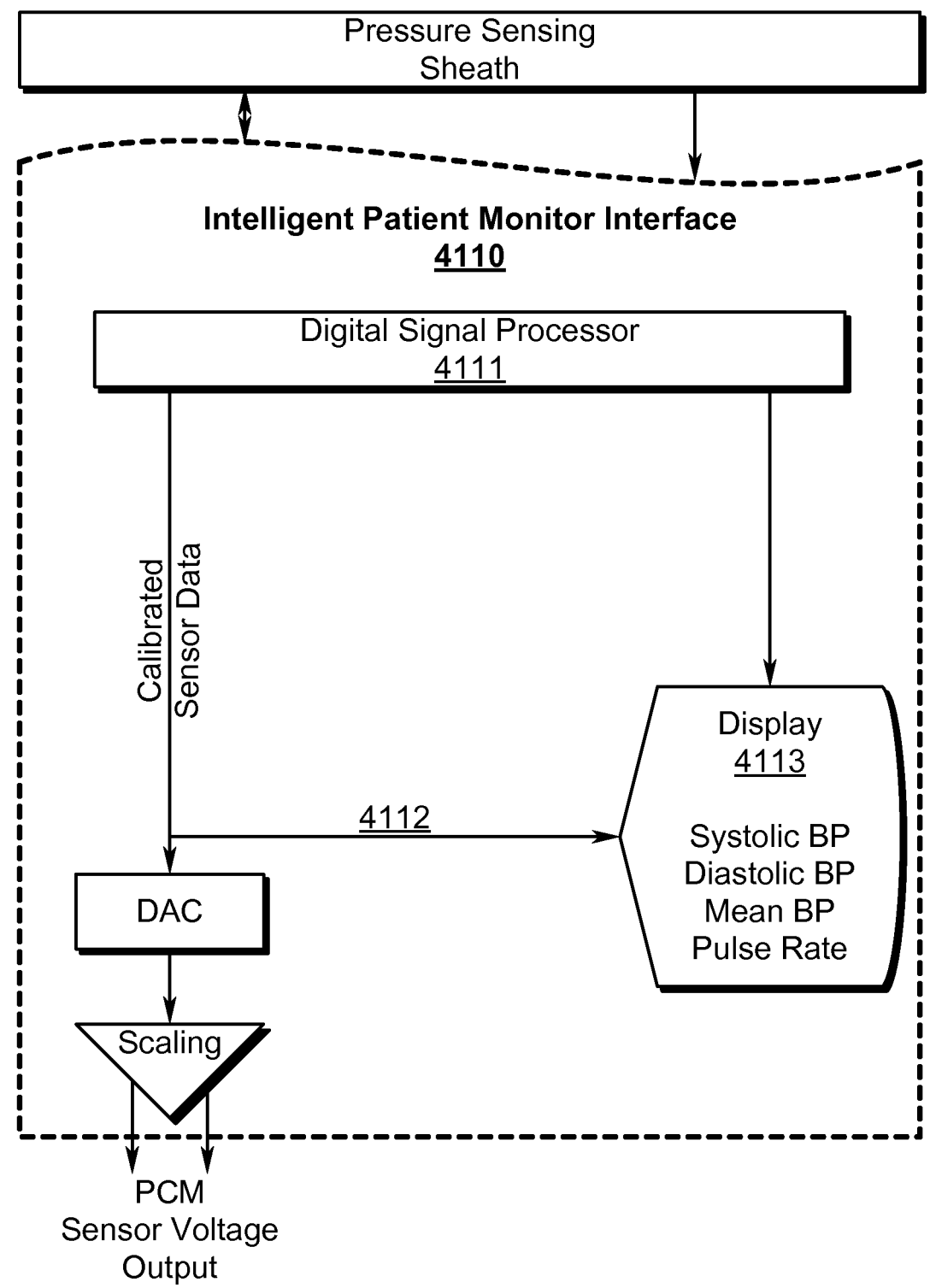
FIG. 41 illustrates a preferred exemplary embodiment of the present invention as applied to an intelligent patient monitoring interface in the context of a conventional blood pressure monitor (BPM) system configured to display systolic blood pressure, diastolic blood pressure, mean blood pressure, and heart rate values.

As generally illustrated in FIG. 41 (4100), the present invention anticipates an embodiment wherein the intelligent patient monitor interface (4110) permits the calibrated sensor data (digital bridge sense value computed by the digital signal processor (4111)) (4112) to be displayed (4113) as a systolic blood pressure, diastolic blood pressure, mean blood pressure, and/or heart rate value.

Selected Pressure Display (4200)

Figure 42:
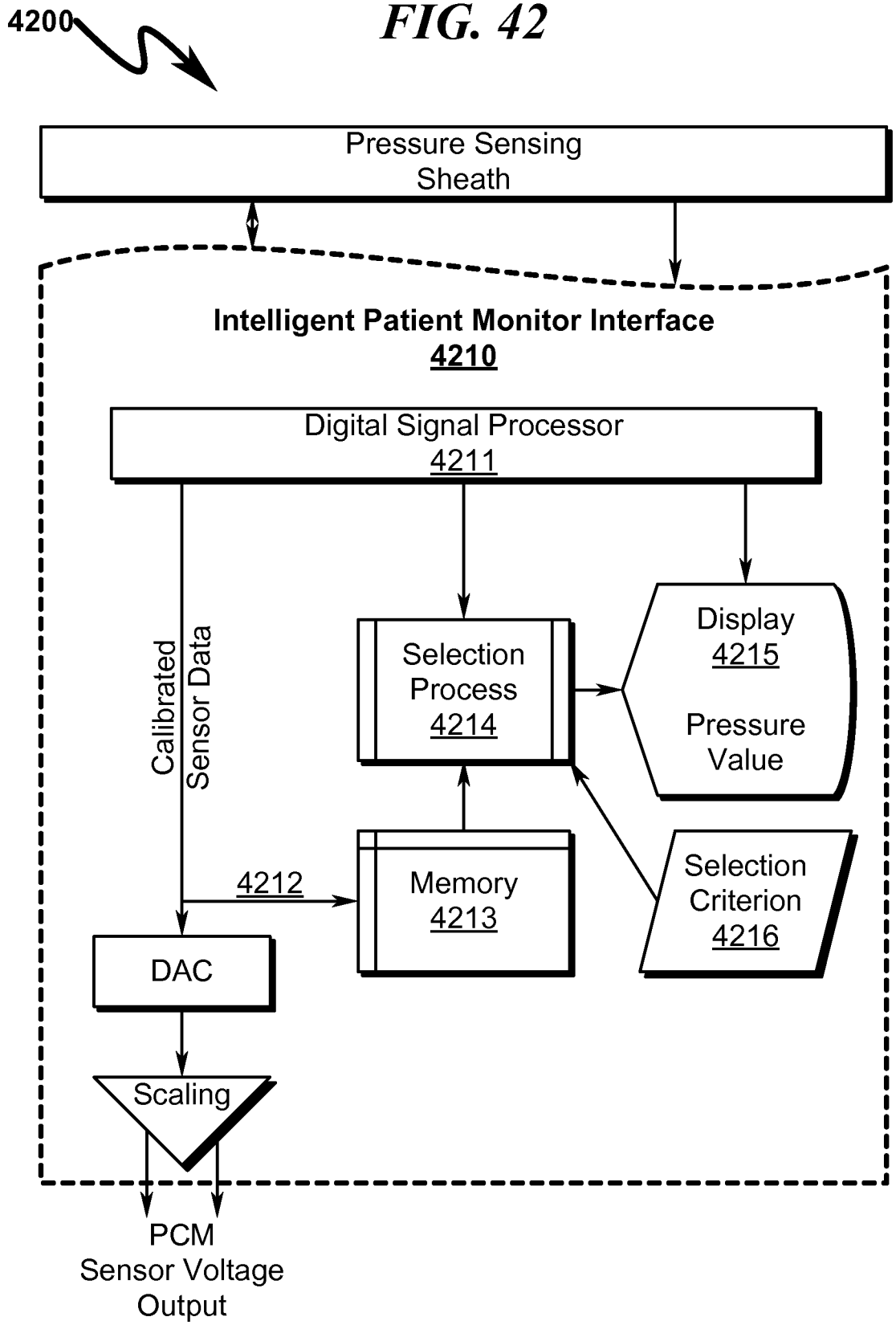
FIG. 42 illustrates a preferred exemplary embodiment of the present invention as applied to an intelligent patient monitoring interface that implements memory storage of pressure data and selection of this pressure data for presentation on a display.

As generally illustrated in FIG. 42 (4200), the present invention anticipates an embodiment wherein the intelligent patient monitor interface (4210) permits a plethora of calibrated sensor data (digital bridge sense value computed by the digital signal processor (4211)) (4212) to be stored in a memory device (4213) and processed by a selection process (4214) (typically under control of the digital signal processor (4211)) and then presented on a visual display device (4215). The selection process (4214) may optionally incorporate a human interface to permit definition of the selection criterion (4216).

One skilled in the art will recognize that a wide variety of selection methodologies may be implemented in the selection process (4214), including but not limited to mean, peak, weighted averaging, and other methodologies.

Analyzed Pressure Display (4300)

Figure 43:
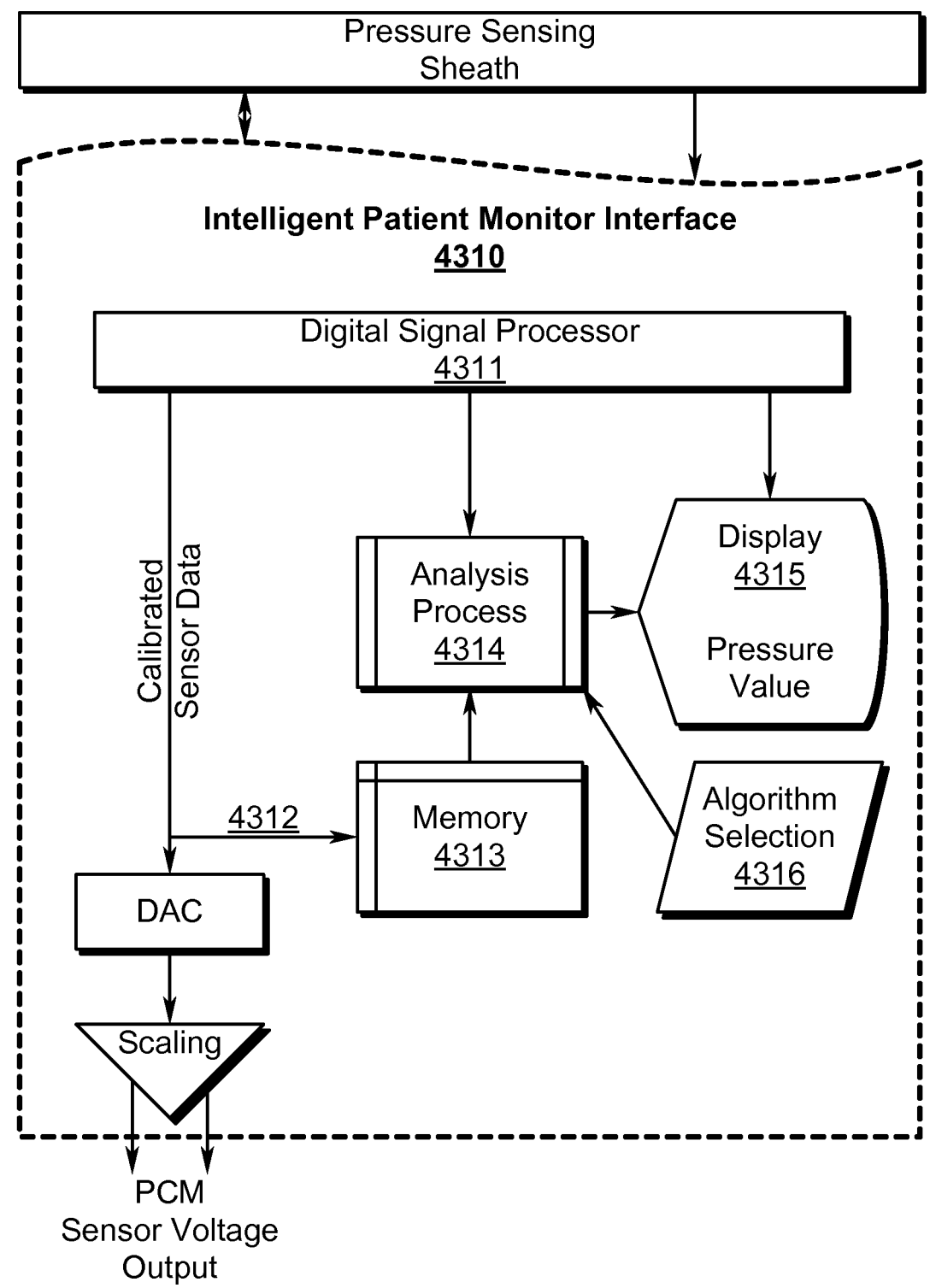
FIG. 43 illustrates a preferred exemplary embodiment of the present invention as applied to an intelligent patient monitoring interface that implements memory storage of pressure data and analysis of this pressure data for presentation on a display.

As generally illustrated in FIG. 43 (4300), the present invention anticipates an embodiment wherein the intelligent patient monitor interface (4310) permits a plethora of calibrated sensor data (digital bridge sense value computed by the digital signal processor (4311)) (4312) to be stored in a memory device (4313) and processed by an analysis process (4314) (typically under control of the digital signal processor (4311)) and then presented on a visual display device (4315). The analysis process (4314) may optionally incorporate a human interface to permit selection of the analysis algorithms (4316) to be applied to the pressure data (4312).

One skilled in the art will recognize that a wide variety of signal analysis methodologies may be implemented in the analysis process (4314), including but not limited to averaging, curve fitting, interpolation, extrapolation, peak fitting, peak selection, mean averaging, and other known analysis techniques. It is specifically anticipated that the high fidelity nature of the digital data (4312) will permit real-time analysis of the pressure waveforms recorded within the memory device (4313).

Sampled Pressure Display (4400)

Figure 44:
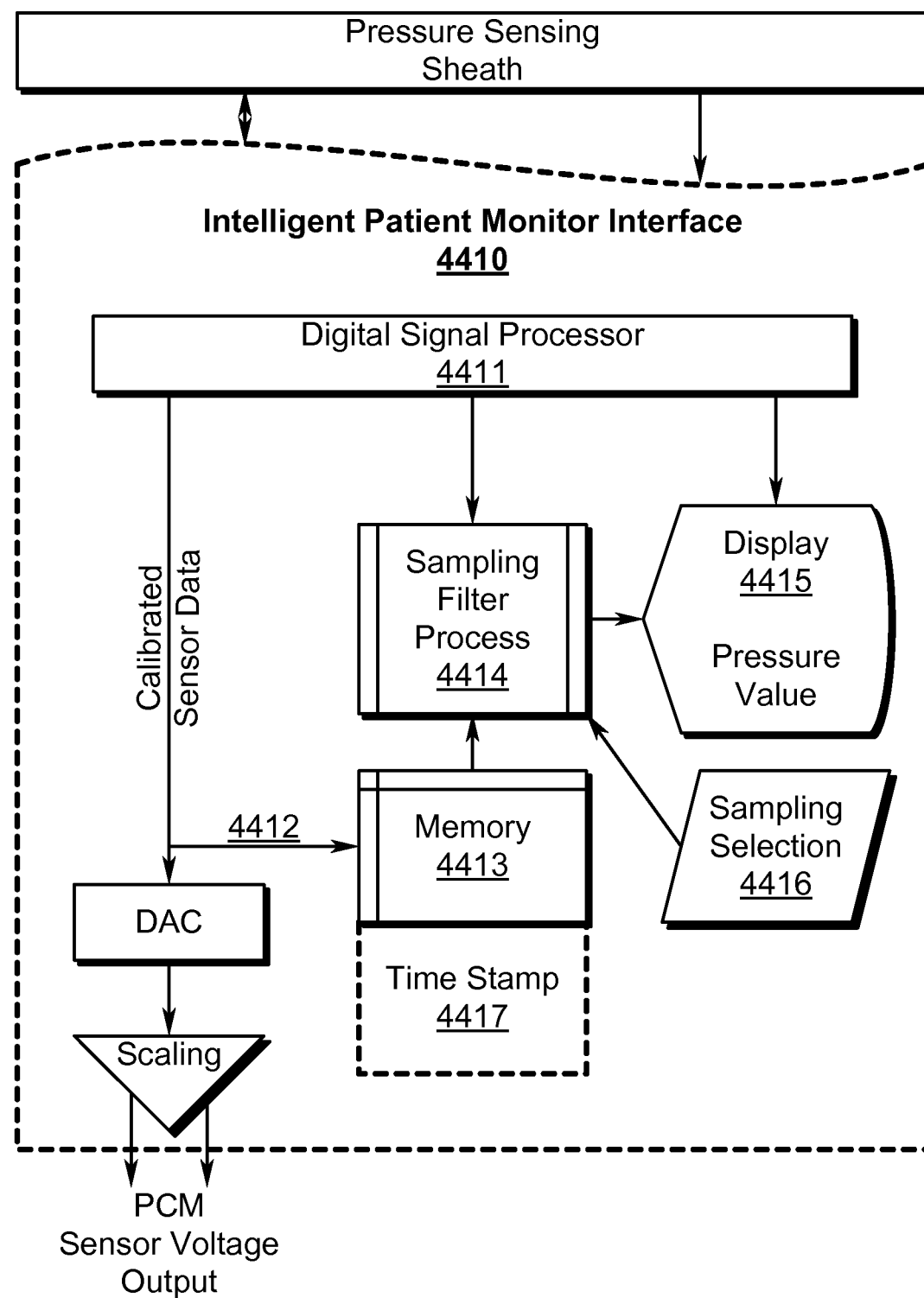
FIG. 44 illustrates a preferred exemplary embodiment of the present invention as applied to an intelligent patient monitoring interface that implements memory storage of pressure data and sampling of this pressure data for presentation on a display.

As generally illustrated in FIG. 44 (4400), the present invention anticipates an embodiment wherein the intelligent patient monitor interface (4410) permits a plethora of calibrated sensor data (digital bridge sense value computed by the digital signal processor (4411)) (4412) to be stored in a memory device (4413) and processed by a sampling process (4414) (typically under control of the digital signal processor (4411)) and then presented on a visual display device (4415). The sampling process (4414) may optionally incorporate a human interface to permit selection of the sampling criterion (4416) to be applied to the pressure data (4412). Note in this embodiment variant a timer and/or time stamp data (4417) may be utilized in conjunction with the memory data (4413) to select or sample a portion of a collected data sample within a given sampling period. One skilled in the art will recognize that this timing function may also be integrated within the digital signal processor (4411).

One skilled in the art will recognize that a wide variety of signal sampling methodologies may be implemented in the sampling process (4414), including but not limited to averaging, decimation, value limiting, noise filtering, and other known sampling techniques.

Hybrid Display Architectures

The data reduction, selection, analysis, and sampling techniques generally illustrated in FIG. 41 (4100)-FIG. 44 (4400) may be combined to form hybrid display architectures that integrate these techniques in a wide variety of ways. One skilled in the art will be aware from the teachings of these FIGURES and the remaining invention disclosure that these combinations present a very wide variety of possible patient monitoring capabilities.

Display Technologies

While a wide variety of displays may be utilized in the context of the present invention, the use of graphical touch screens may be optimal in many preferred embodiments. Additionally, the use of wireless links to smartphones, computer tablets, and other computing devices is also anticipated within the scope of the present invention.

Bidirectional Date Communication/Control (4500, 4600)

Communication Interfaces

Figure 45:
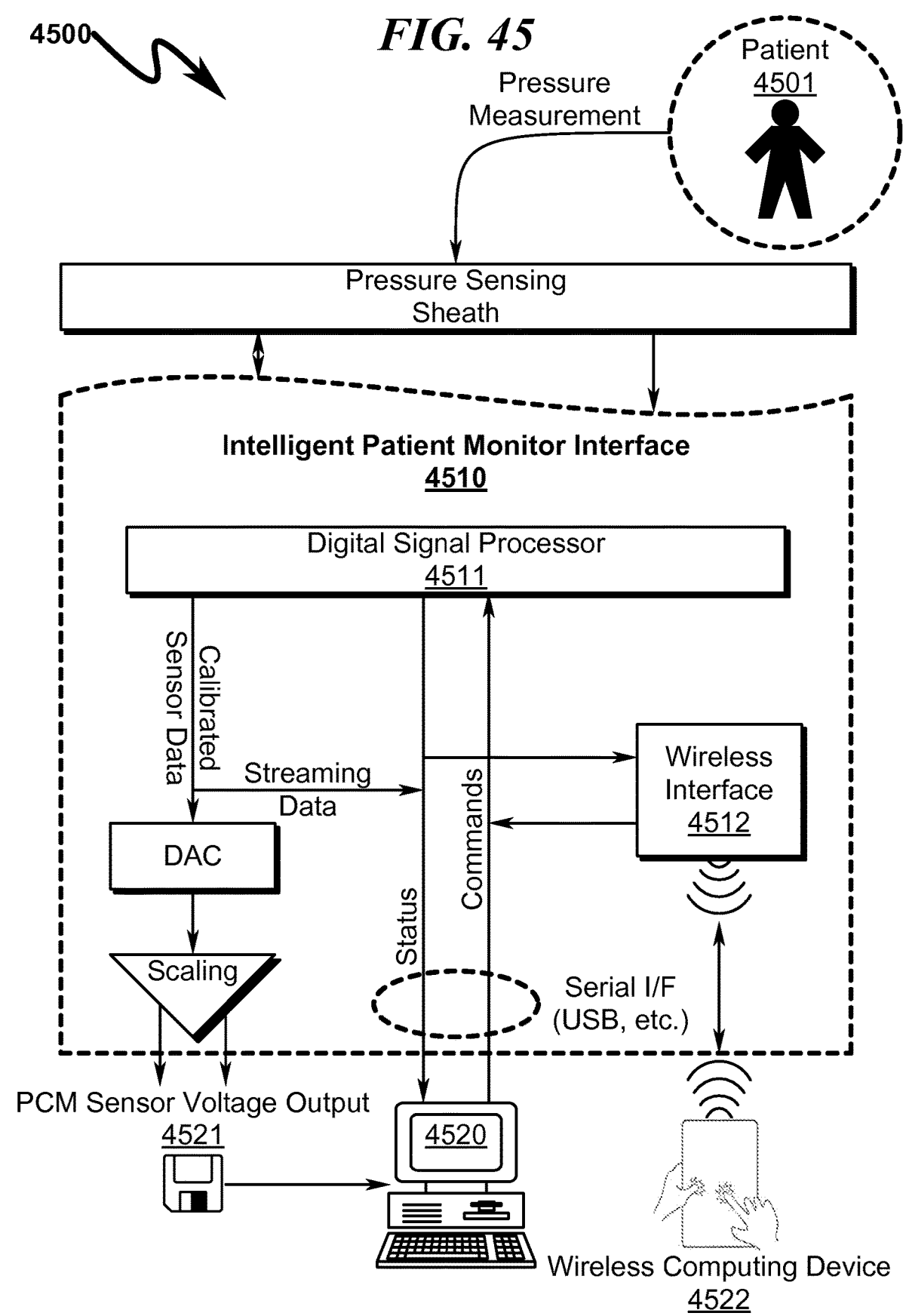
FIG. 45 illustrates a preferred exemplary embodiment of the present invention as applied to an intelligent patient monitoring interface that implements bidirectional communication with an external analysis computer using wired and wireless technologies.

As generally depicted in FIG. 45 (4500), the present invention anticipates that the digital signal processor (4511)

may communicate bidirectionally with an external data analysis computer (4520) running under control of software read from a computer readable medium (4521) for the purposes of real-time/offline data/status collection by the analysis computer (4520) and/or configuration/control of the intelligent patient monitoring interface (4510) by the analysis computer (4520).

Within this context it is anticipated that a wireless interface (4512) may be incorporated into the intelligent patient monitoring interface (4510) to permit the use of remote wireless computing devices (4522) (including but not limited to laptops, smartphones, tablet computers, and the like) to function in this data analysis capacity. The present invention specifically anticipates that this wireless interface may be utilized in some preferred embodiments wherein the intelligent patient monitoring interface (4510) is part of a medical device that is embedded within a patient such that pressure measurements are taken continuously (or at specified intervals) and then wirelessly transmitted to a portable display device for storage, analysis, and/or transmission to a physician for further review and diagnosis.

Analysis Software

Within this context a wide variety of application data collection/analysis software (4521) is envisioned to support patient monitoring and/or diagnosis functions to be performed by either the analysis computing devices (4520, 4522) and/or the digital signal processor (4511) contained within the intelligent patient monitoring interface (4510). On-board real-time and post-processing capability within the digital signal processor (4511) is also anticipated by the present invention. This may be implemented using a high performance processor, or multiple processors. Among the potentially valuable functions of this capability include the calculation of: FFTs, sorting algorithms, searching algorithms, amplitude, power, phase spectrums, filters, correlations, windowing, triggers, thresholding, waveform analysis, wavelet processing, encryption, decryption, formatting, timers, and statistical analysis, etc. One skilled in the art will recognize that this list is non-exhaustive and merely exemplary.

Display Technologies

This analysis functionality may be combined with a wide variety of display technologies as anticipated by the present invention. This may include a high resolution graphical display, optionally including touch screen technology for some applications. This display would be capable of supporting multiple types of graphical read outs (and inputs). Among the information that could be displayed are: spectral information, amplitude waveforms, filter characteristics, diagnostics, waveform analysis, etc. This capability may directly support the display of sophisticated data analysis detailed above. One skilled in the art will recognize that this list is non-exhaustive and merely exemplary. This capability enables more sophisticated user interaction and simpler user interface development and software updates using soft keys.

Logging

The analysis functions detailed above may incorporate a sophisticated internal logging function. In concert with the conventional blood pressure processing applications detailed previously, this logging function tracks and stores information such as: sensor performance, environmental exposure, functional monitoring (e.g., power cycles, optics environment, LED life, etc.), software licensing, maintenance periods, compatibility parameters, data quality control, errors, crashes, condition-based maintenance monitoring, PSS insertions and tracking, etc. One skilled in the art will recognize that this list is non-exhaustive and merely exemplary.

Factory/Field Maintenance

Figure 46:
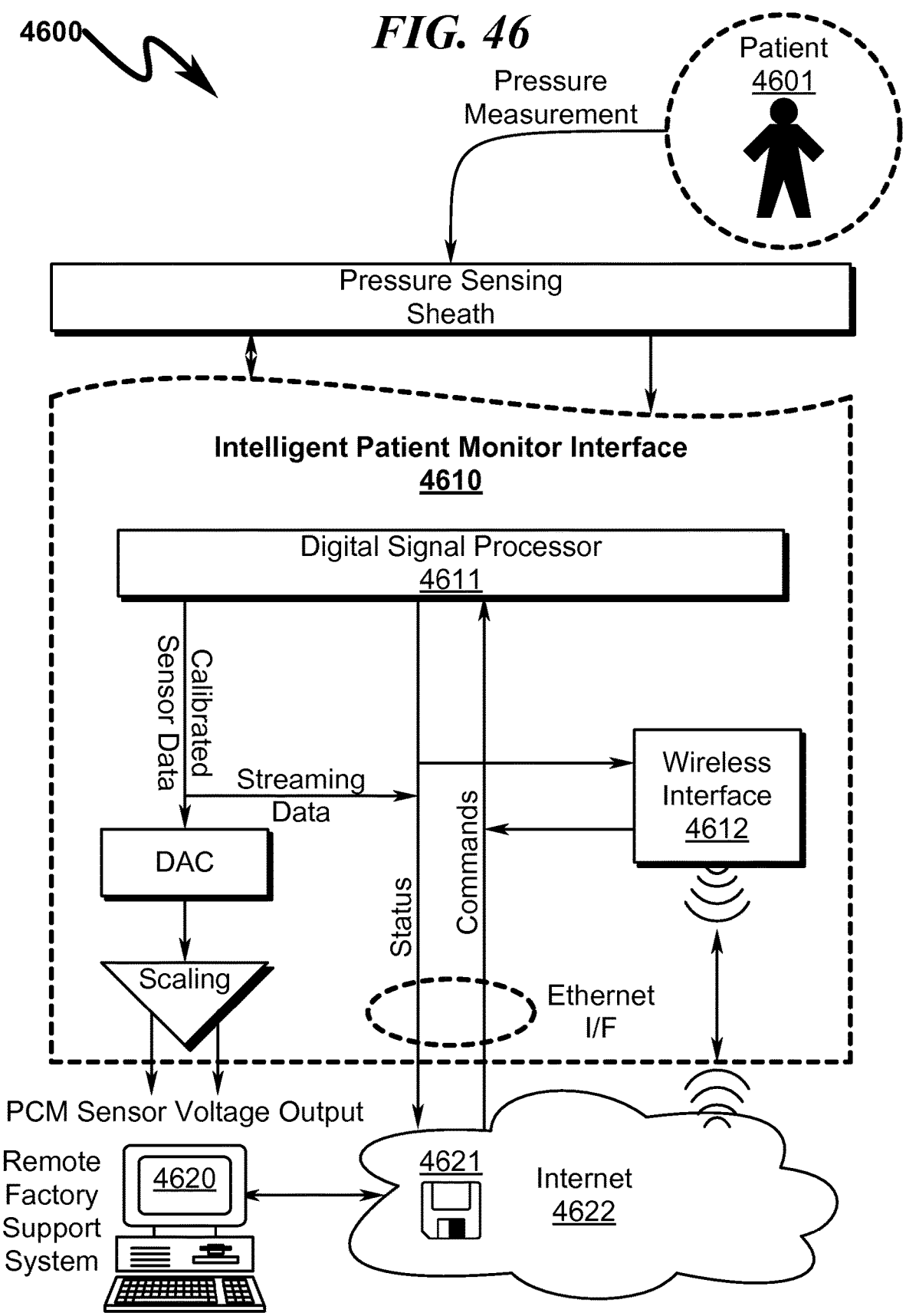
FIG. 46 illustrates a preferred exemplary embodiment of the present invention as applied to an intelligent patient monitoring interface that implements bidirectional communication over a computer network for the purposes of providing remote factory support for the BPM.

As generally illustrated in FIG. 45 (4500), the present invention anticipates that a serial interface (USB, etc.) may be used to communicate between the intelligent patient monitor interface (4510) and an external computer system for use as a factory maintenance connection. This maintenance functionality may also be field-based, wherein condition-based self-assessment or remote instrument diagnostics and maintenance using wired or wireless connections through the Internet (4622) are implemented as depicted in FIG. 46 (4600). This anticipated capability allows local condition-based as well as factory level diagnostic and maintenance functions (4620) to be performed remotely in the field, thus reducing costs and down time. This capability, coupled with the analysis and logging capabilities detailed above, allow the BPM to "call home" when certain conditions occur (outbound device-initiated communication) as well as be accessed by a remote person or application (inbound remotely initiated) to collect information, diagnose problems, devise solutions, download software (4621), and correct problems in the field.

Exemplary Embodiment System Performance (4700-5600)

Figure 48:
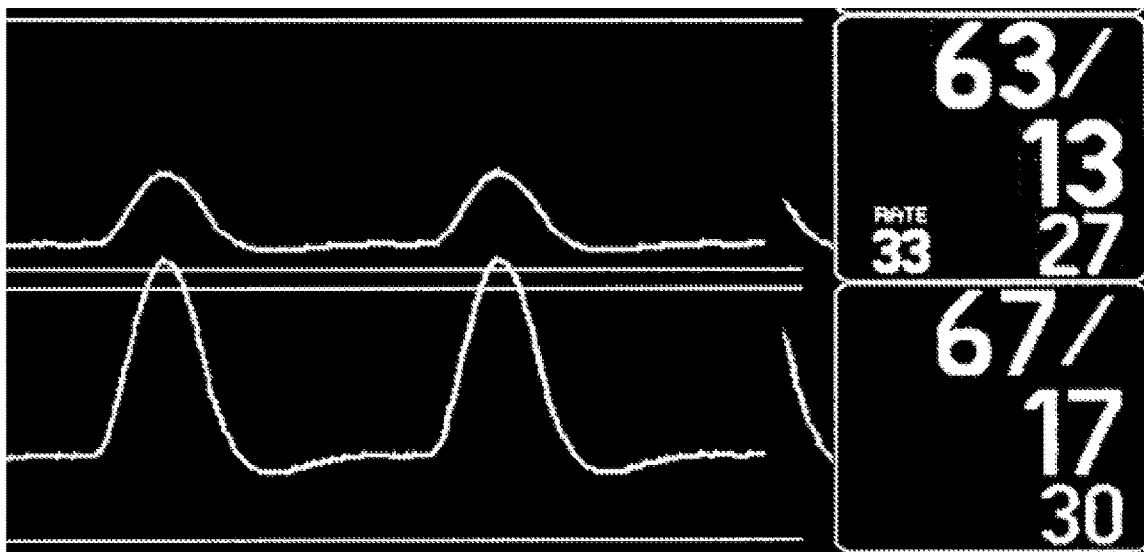
FIG. 48 illustrates a performance comparison of a preferred invention embodiment BPM implementation as it relates to a prior art PCM blood pressure monitor under nominal performance comparison conditions.
Figure 56:
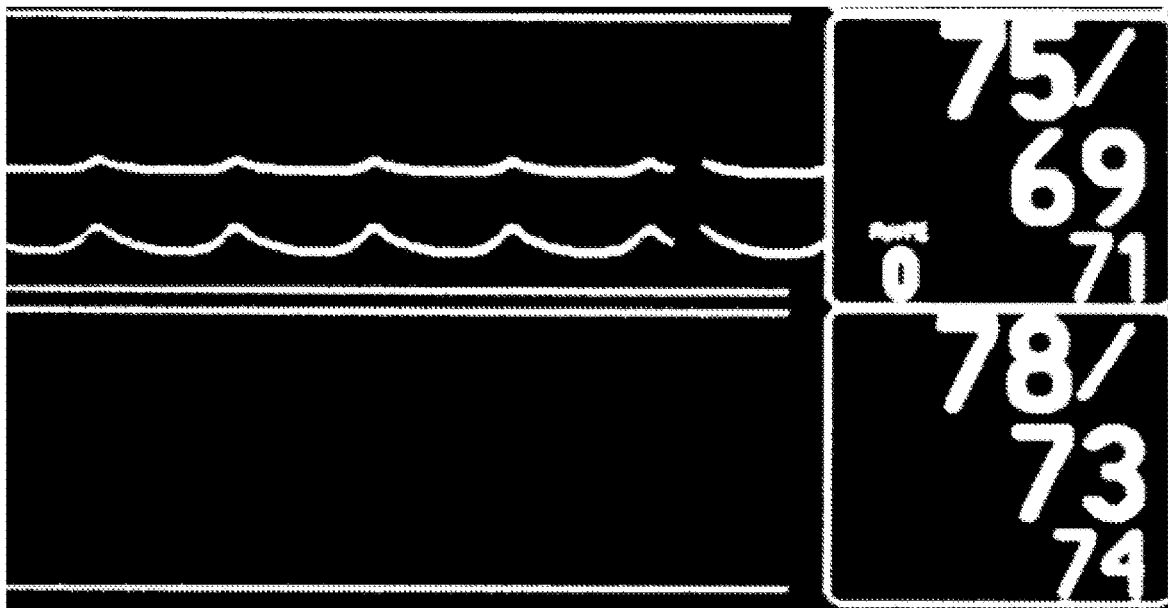
FIG. 56 illustrates a performance comparison of a preferred invention embodiment BPM implementation as it relates to a prior art PCM blood pressure monitor under nominal heart rate conditions with lowest possible stroke volume.

While the present invention may be embodied in a wide variety of configurations, a typical application implemented as a blood pressure monitor (BPM) may exhibit the exemplary performance as depicted in the measurement screen shots and testing conditions depicted in FIG. 48 (4800)-FIG. 56 (5600). These testing conditions and comparisons between PCM and BPM performance will now be discussed in detail.

Static Pressure Accuracy Comparison

Static pressure testing comparing a preferred exemplary invention embodiment as applied to a blood pressure monitor (BPM) system in comparison to a GE model Dash 3000 conventional PCM based blood pressure monitor system were performed at a nominal atmospheric pressure of 763.435 mmHg. Results of this comparison are detailed in the following table:

| Abs P (mmHg) | ΔP (mmHg) | BPM Display (mmHg) | Dash 3000 w/BPM input PMIO (mmHg) | Dash 3000 Edwards (mmHg) |
|---|---|---|---|---|
| 763.435 | 0 | 0 | 0 | 0 |
| 783.435 | 20 | 20 | 20 | 20 |
| 803.435 | 40 | 40 | 40 | 40 |
| 823.435 | 60 | 60 | 60 | 60 |
| 843.435 | 80 | 80 | 81 | 80 |
| 863.435 | 100 | 100 | 101 | 100 |
| 883.435 | 120 | 120 | 121 | 120 |
| 903.435 | 140 | 140 | 141 | 140 |
| 923.435 | 160 | 160 | 160 | 160 |
| 943.435 | 180 | 180 | 180 | 180 |
| 963.435 | 200 | 200 | 200 | 200 |
| 983.435 | 220 | 219 | 220 | 220 |
| 1003.435 | 240 | 239 | 240 | 241 |
| 1023.435 | 260 | 259 | 260 | 261 |
| 1043.435 | 280 | 279 | 280 | 281 |
| 1063.435 | 300 | 299 | 300 | 301 |

The columns represent the following data:
absolute pressure;
delta pressure from atmospheric absolute pressure;
blood pressure measured by BPM preferred invention embodiment and displayed on a BPM attached display (direct data display from compensated optical pressure measurement);
blood pressure measured by BPM and sent to PCM for display via Wheatstone Bridge emulator interface; and
blood pressure measured by PCM using conventional strain gauge blood pressure sensor.

This table indicates that at least under static pressure measurements, the present invention preferred BPM embodiment is in conformance to pressure accuracies demonstrated by conventional PCM blood pressure sensors and systems.

Comparison Testing Between PCM and BPM Systems

A series of comparison tests were performed on a blood pressure test apparatus to demonstrate some of the extremes of pressure at which the present invention Blood Pressure Monitor (BPM) system exemplary embodiment continues to register systolic and diastolic pressures while the standard conventional patient care monitor (PCM) fails to show separation between systolic and diastolic pressures. For this testing, an artificial circulatory system was set up using a beaker of water and a pulsatile pump as the heart. A single output port with separate readouts for an external pressure transducer (Wheatstone Bridge) and for a fiber optic output (pressure sensing sheath, or PSS) was tested. In all images depicted, the PCM device utilized is a GE Dash 3000 model PCM.

Within this context the top set of numbers displayed on the PCM is the readout from the external transducer Wheatstone Bridge. The bottom set of numbers on the PCM is the readout from the analog output (Wheatstone Bridge emulator) from the BPM. The measured BPM data depicted in each FIGURE is the digital output directly from the signal conditioner. While the BPM utilized in this testing did not display pulse rate, it was also observed that there was a disconnection at times between display of a systolic and diastolic vs. display of pulse rate on the PCM (i.e., sometimes pressures were displayed but pulse rate still shows "0"). Examples of that phenomenon are also illustrated in these FIGURES.

Overall, these phenomena show that there are many factors contributing to error on the PCM. These may include signal dampening from the tubing extending to the Wheatstone Bridge, which is mounted on an IV pole external to the patient. These errors may also include filtration of signal as it passes to the PCM, or even an algorithmic source of error in how systolic and/or diastolic pressures are calculated. This testing indicates, however, that while the PCM functions well under ordinary circumstances, it may give erroneous results under extreme circumstances, which are the circumstances where it is most critical that results be error-free. In contrast, the dynamic range of the present invention BPM implementation permits accurate measurement operation even under these extreme measurement conditions.

Testbed Configuration (4700)

Figure 47:
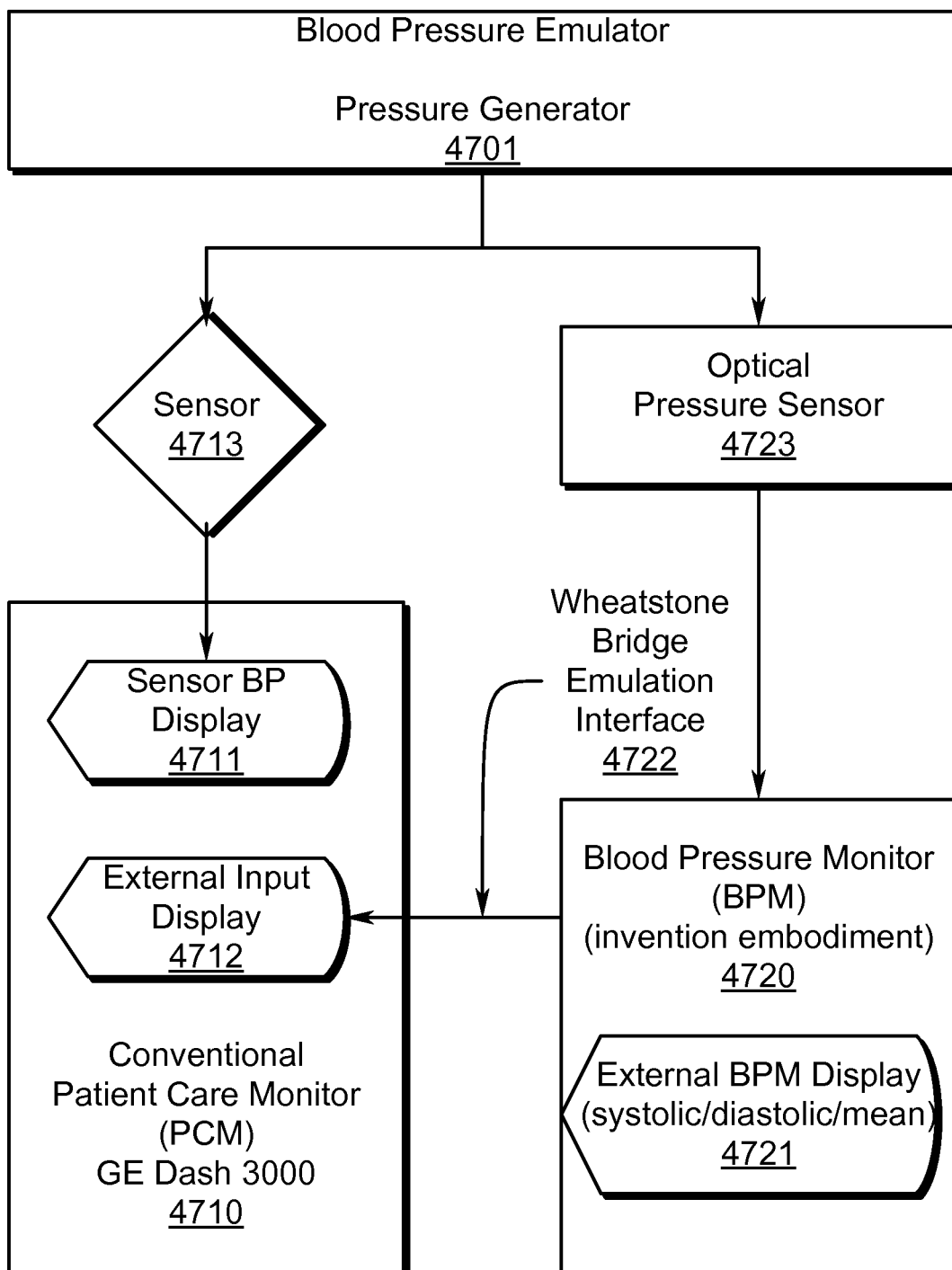
FIG. 47 illustrates a blood pressure monitor testbed configuration used to compare prior art blood pressure monitor technology utilizing conventional PCMs with that of the optical pressure sensing technology as taught by the present invention.

The testing configuration used to compare conventional PCM blood pressure monitoring technology with that of the optical pressure sensing technology as taught by the present invention is generally illustrated in FIG. 47 (4700). Here a pressure generator (4701) is used to generate an emulated blood pressure waveform under a variety of stroke rates, pulse (heart) rates, systolic pressures, and/or diastolic pressures.

The PCM measurement baseline comprises a conventional PCM system (model GE Dash 3000) (4710) having two independent display channels (4711, 4712) that correspond to a conventional pressure sensor (4713) and emulated Wheatstone Bridge input (4722) from a preferred BPM embodiment of the present invention (4720). The present invention embodiment (4720) depicted incorporates an external display (4721) to present systolic/diastolic/mean measured blood pressure in conjunction with an optical pressure sensing element (4723).

Note that this testbed permits the direct comparison of traditional PCM-based blood pressure measurements (as displayed on the PCM display (4711)) to be compared with both the direct pressure data obtained from the BPM embodiment (4720) as displayed on the external BPM display (4721), but also how the PCM interprets this raw data as depicted in its Wheatstone Bridge external input display (4712). From the discussion of the test results below, it is evident that the PCM (4710) not only has difficulty in accurately sensing blood pressure from the sensor element (4713) under some circumstances, this difficulty extends to external input displays (4712) associated with any other analog-based input.

Nominal PCM Performance—Low Diastolic/High Systolic Pressure (4800)

FIG. 48 (4800) illustrates a test condition in which low diastolic pressure (16) is present but high enough systolic pressure maintained to display pressures both on the BPM and the PCM. Under most normal physiological conditions, this consistency is seen between the BPM and the PCM.

Reduced Stroke Volume (4900)

Figure 49:
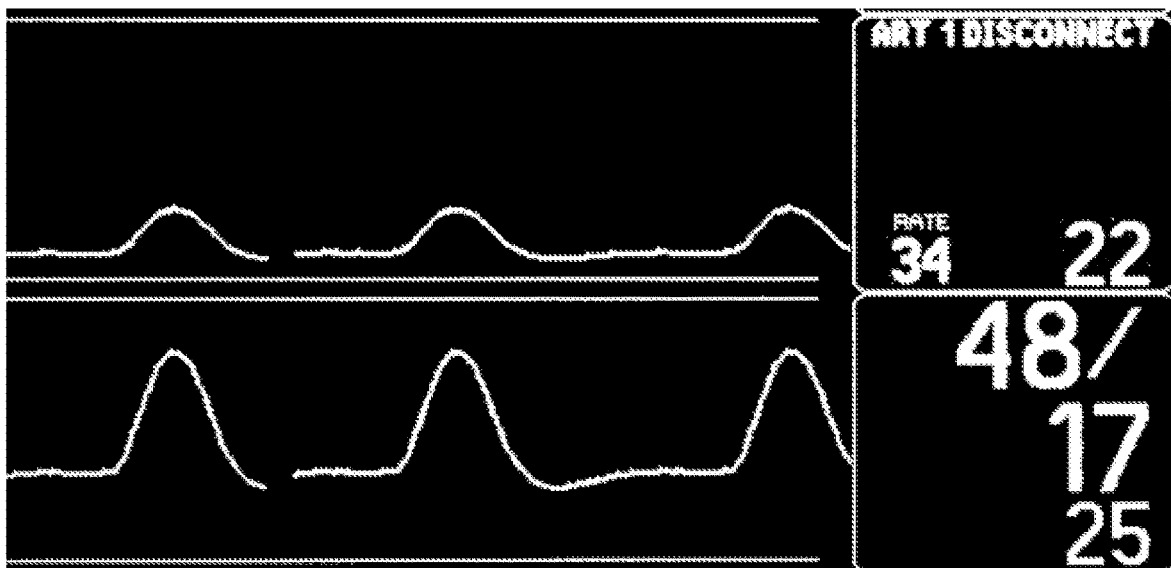
FIG. 49 illustrates a performance comparison of a preferred invention embodiment BPM implementation as it relates to a prior art PCM blood pressure monitor under reduced stroke volume test conditions.

FIG. 49 (4900) illustrates a test condition in which the pulse rate remains 30, but stroke volume has been decreased. Systolic now 48, but diastolic remains 17, and pressures are displayed on the BPM and on the PCM output from the BPM, but pressures are not detected from the Wheatstone Bridge.

Lower Stroke Volume (5000)

Figure 50:
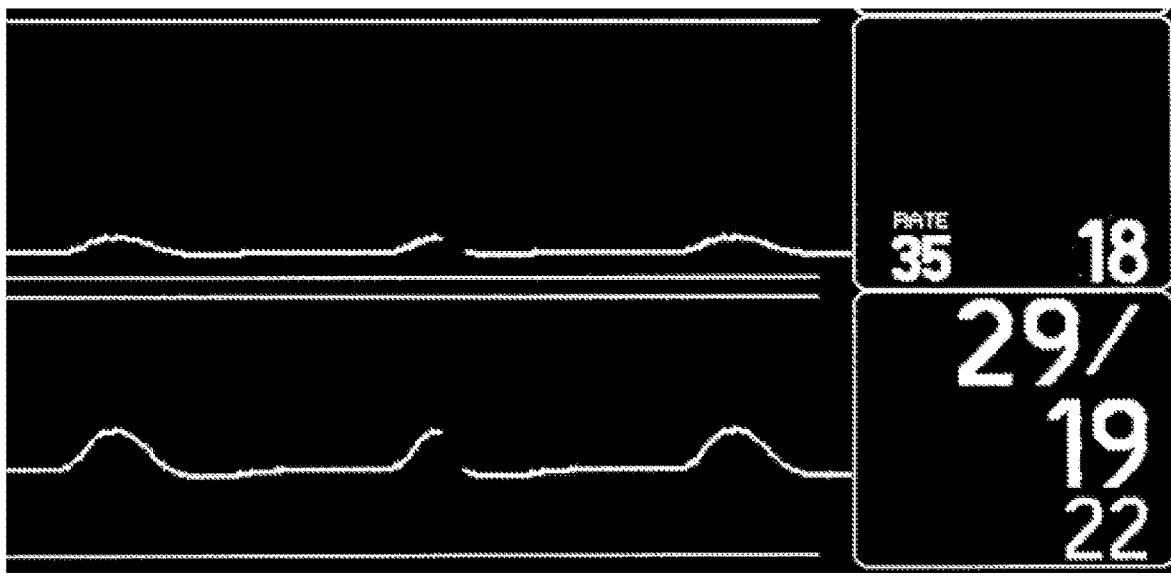
FIG. 50 illustrates a performance comparison of a preferred invention embodiment BPM implementation as it relates to a prior art PCM blood pressure monitor under lower stroke volume test conditions.

FIG. 50 (5000) illustrates a test condition in which the stroke volume is still lower. BPM pressure is detected as 29/18 on external display but not detected from the PCM external transducer even though pulse rate indicates 35.

Lowest Stroke Volume (5100)

Figure 51:
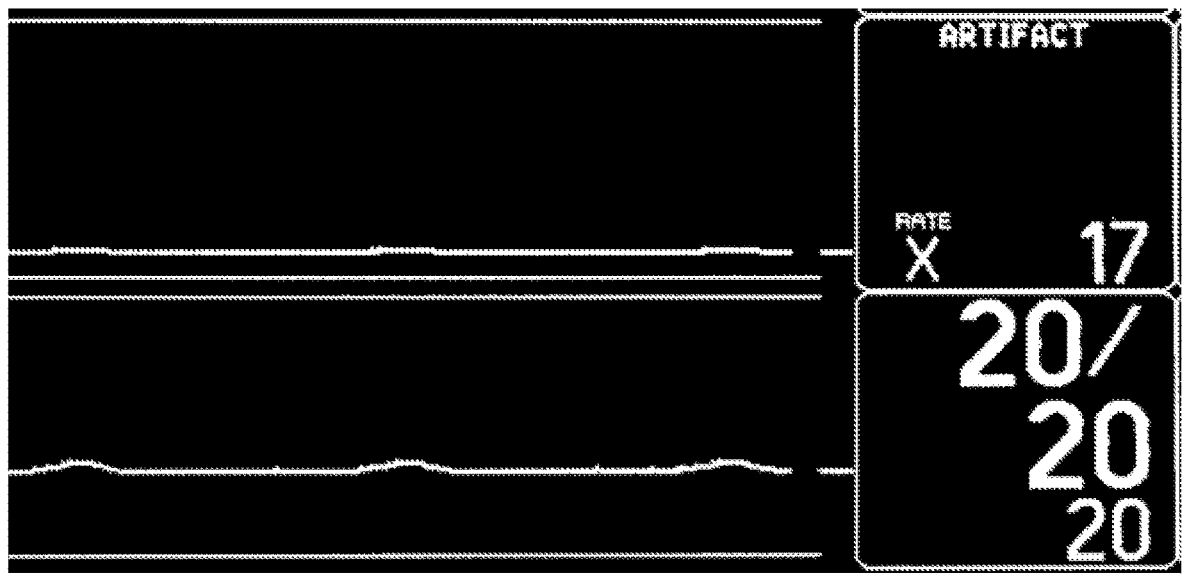
FIG. 51 illustrates a performance comparison of a preferred invention embodiment BPM implementation as it relates to a prior art PCM blood pressure monitor under lowest stroke volume test conditions.

FIG. 51 (5100) illustrates a test condition using the lowest stroke volume achievable on the syringe pump. BPM still registers 22/19 on external display. No BP detection on PCM external transducer. Mean only on BPM as displayed by PCM monitor. A difference of only 3 mm Hg between systolic and diastolic still registers on the BPM.

Lowest Stroke Volume+Heart Rate 40 (5200).

Figure 52:
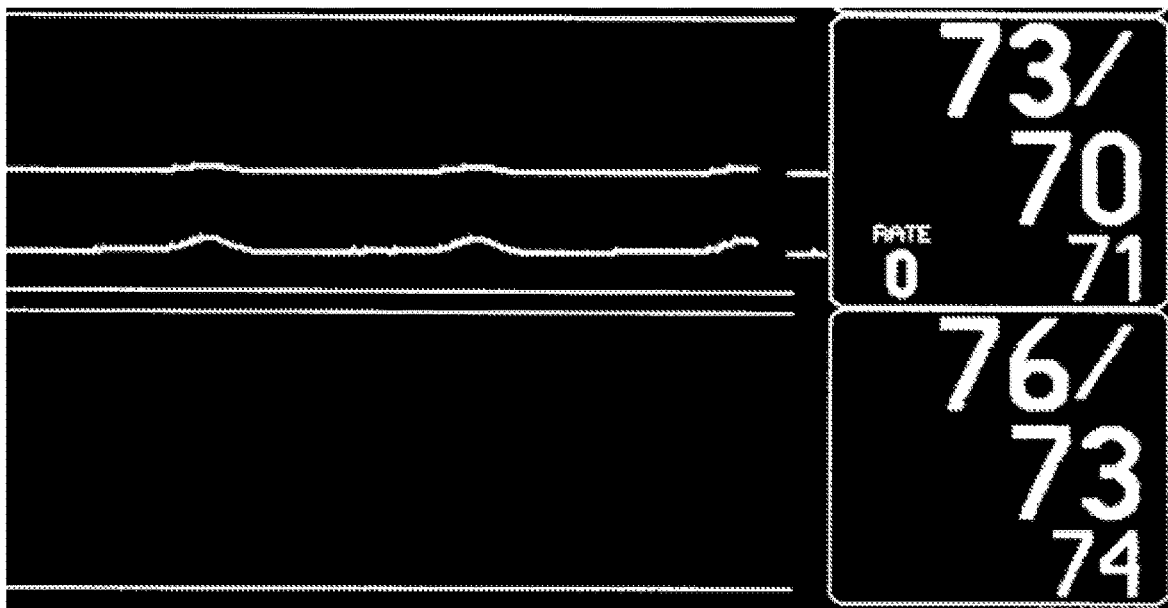
FIG. 52 illustrates a performance comparison of a preferred invention embodiment BPM implementation as it relates to a prior art PCM blood pressure monitor under reduced stroke volume test conditions with increased heart rate.

FIG. 52 (5200) illustrates a test condition using a heart rate increased to 40, while still using a lowest possible stroke volume. 76/72 registered on BPM external display. This test setup registers on all devices, although heart rate shows "0" on PCM.

Heart Rate 12 (5300)

Figure 53:
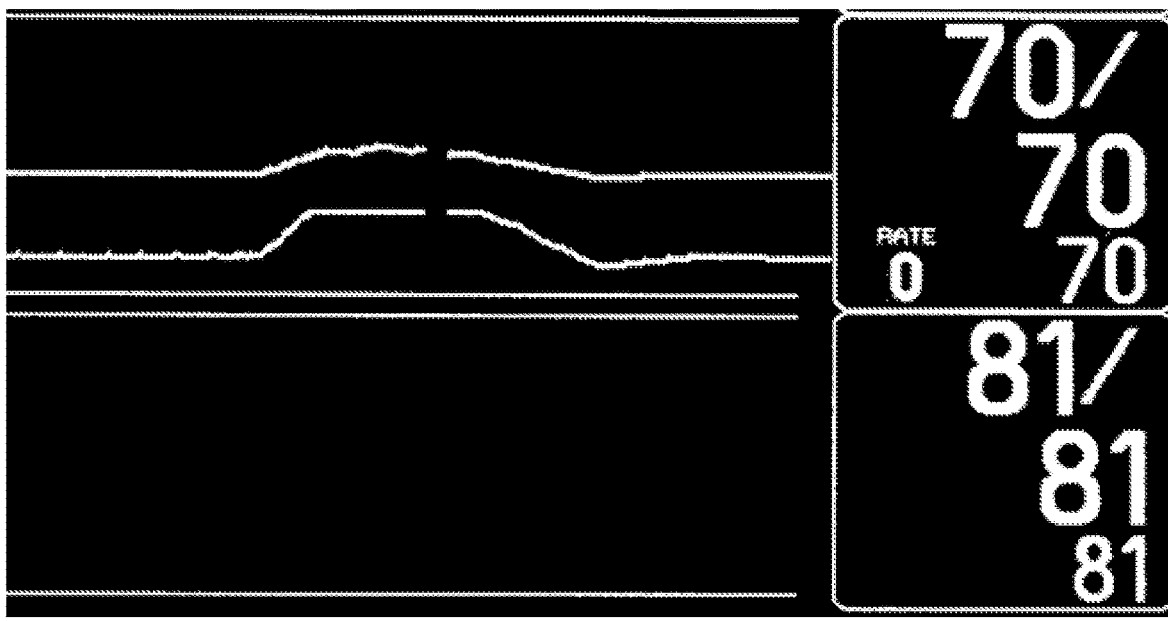
FIG. 53 illustrates a performance comparison of a preferred invention embodiment BPM implementation as it relates to a prior art PCM blood pressure monitor under reduced heart rate conditions.

FIG. 53 (5300) illustrates a test condition using a low pulse rate of 12. 87/70 is registered on the BPM external display. Zero (0) pulse and no systolic/diastolic separation on PCM. This test setup reveals a significant problem in conventional PCM BP systems in their inability to accurately measure blood pressure at very low heart rates.

Very Low Stroke Volume+Heart Rate 12 (5400)

Figure 54:
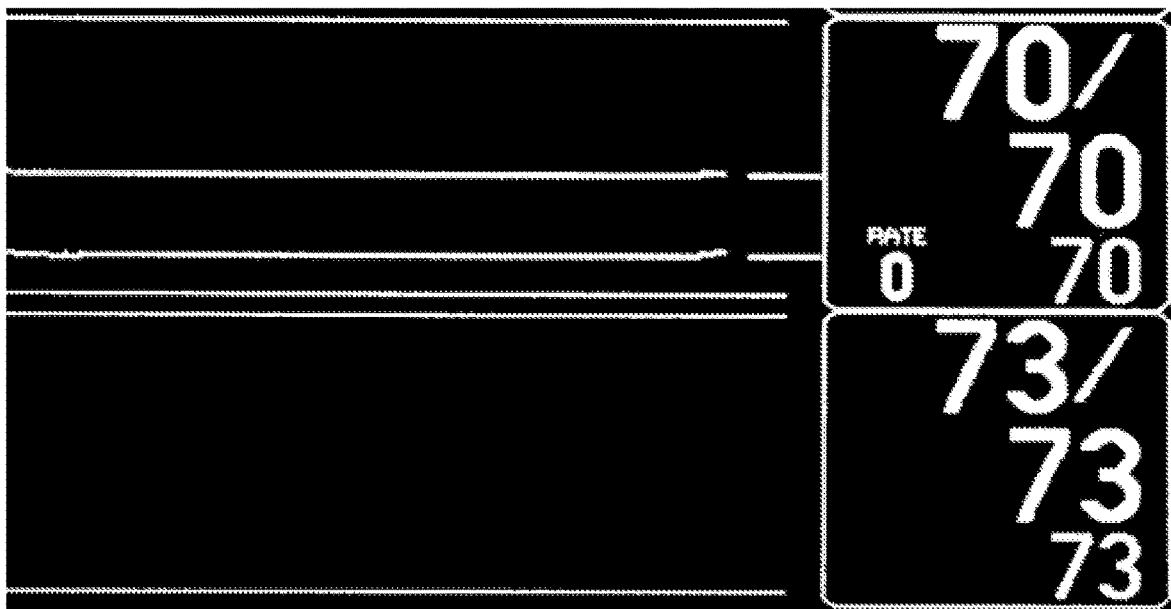
FIG. 54 illustrates a performance comparison of a preferred invention embodiment BPM implementation as it relates to a prior art PCM blood pressure monitor under reduced heart rate conditions with reduced stroke volume.

FIG. 54 (5400) illustrates a test condition using a low pulse rate of 12 with a very low stroke volume. 76/72 is registered on the external BPM display. Only a mean BP is registered on the PCM with "0" pulse rate.

Heart Rate 12+Lowest Possible Stroke Volume (5500)

Figure 55:
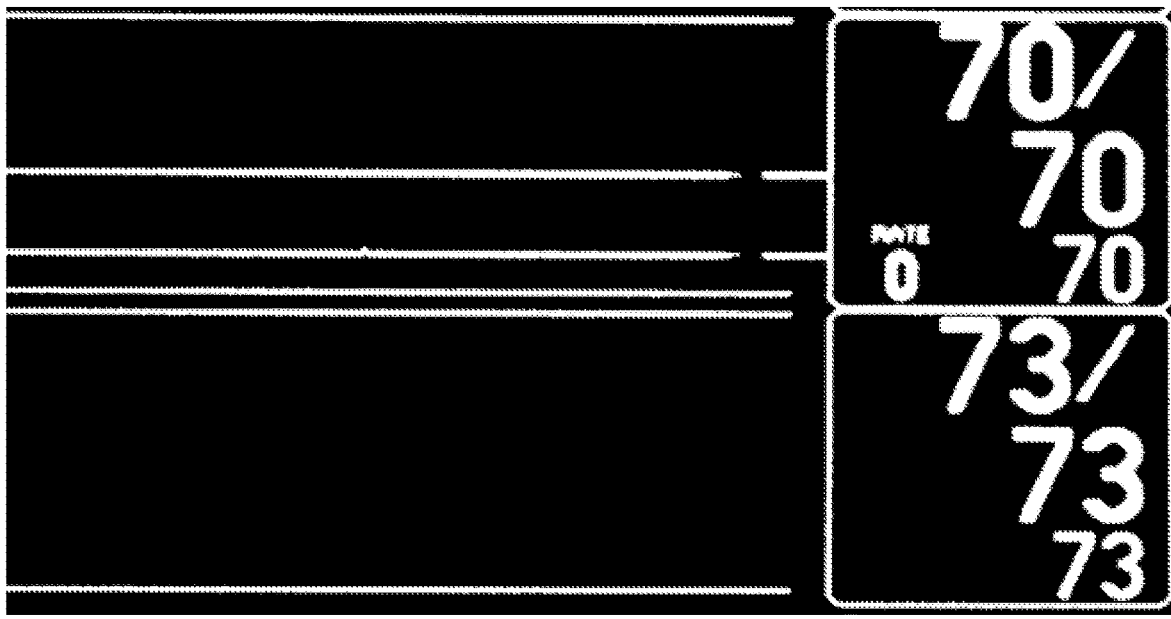
FIG. 55 illustrates a performance comparison of a preferred invention embodiment BPM implementation as it relates to a prior art PCM blood pressure monitor under reduced heart rate conditions with lowest possible stroke volume.

FIG. 55 (5500) illustrates a test condition using a low pulse rate of 12 with the lowest possible stroke volume. The BPM external display shows 73/72 (1 mm Hg systolic/diastolic separation) but the PCM displays a mean BP only with 0 pulse.

Heart Rate 80+Lowest Possible Stroke Volume (5600)

FIG. 56 (5600) illustrates a test condition using a heart rate of 80 and the lowest possible stroke volume. 78/72 is registered on the external BPM display. Pressure detected but zero (0) pulse rate displayed on the PCM. This test scenario indicates that even if pulse rates are nominal, low stroke rates and/or near unity systolic/diastolic pressure ratios are situations wherein conventional PCM blood pressure monitors fail to accurately record blood pressure. In contrast, the present invention as applied to this situation provides consistently accurate measurement results.

Exemplary Embodiment Data Capture

Exemplary Blood Pressure Waveforms (5700, 5800, 5900, 6000)

Figure 60:
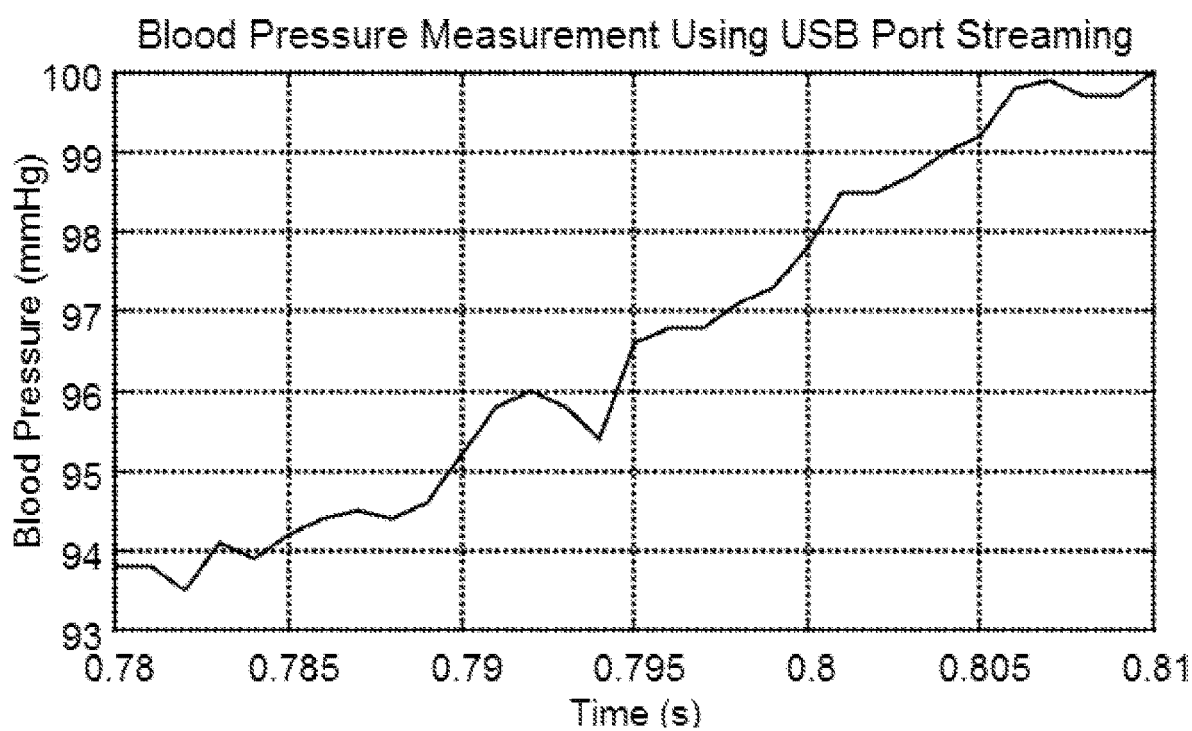
FIG. 60 illustrates an exemplary blood pressure measurement super-fine detail result graph obtained via USB data streaming from a preferred exemplary embodiment of the present invention.

The present invention as embodied in a blood pressure monitor (BPM) system/method is typically capable of processing 500-1000 blood pressure readings per second. These blood pressure readings may be captured in real-time using a digital communications input/output port such as a USB or other serial and/or parallel interface. Examples of data collected using this capture technique using a BioTek pressure waveform simulator are generally illustrated in FIG. 57 (5700)-FIG. 60 (6000).

Figure 57:
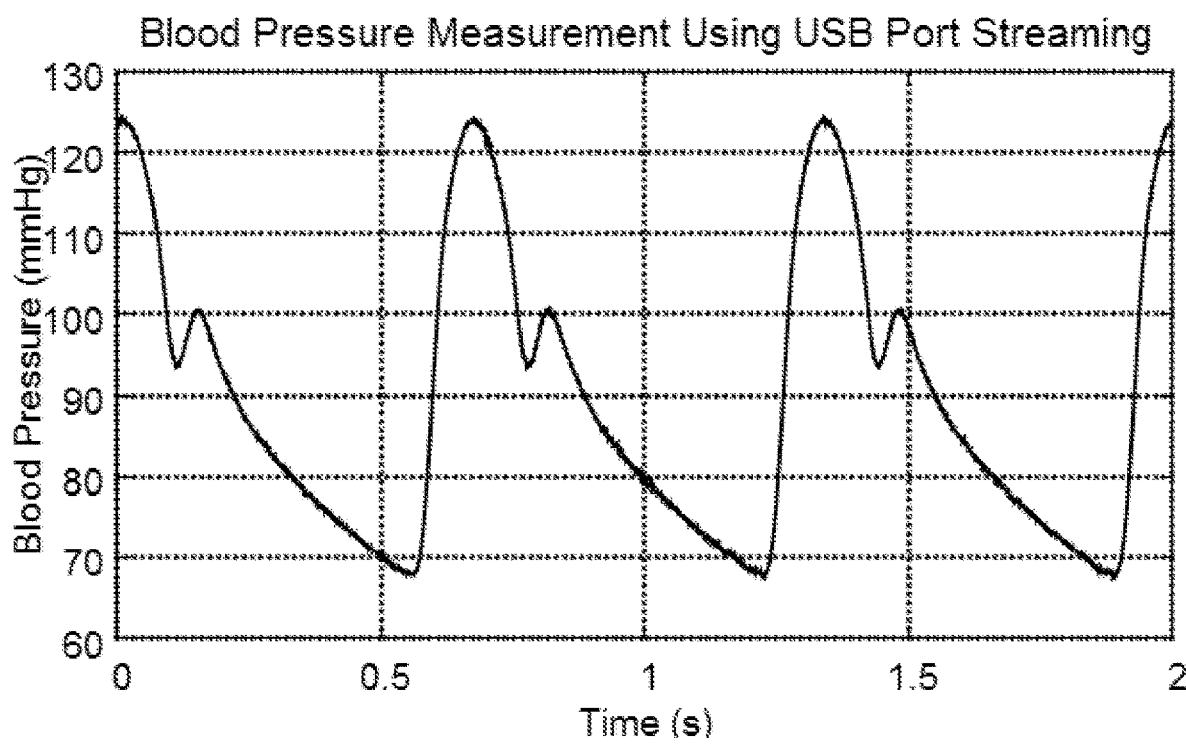
FIG. 57 illustrates an exemplary blood pressure measurement overview result graph obtained via USB data streaming from a preferred exemplary embodiment of the present invention.
Figure 58:
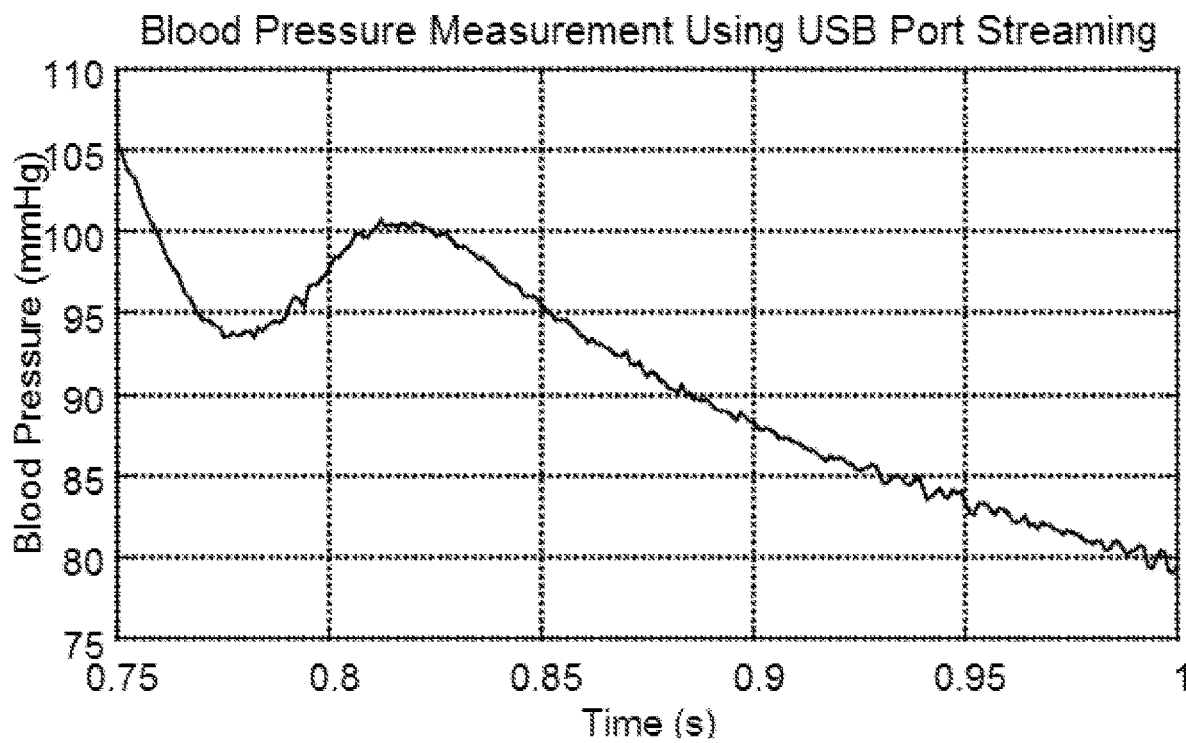
FIG. 58 illustrates an exemplary blood pressure measurement detail result graph obtained via USB data streaming from a preferred exemplary embodiment of the present invention.

FIG. 57 (5700) illustrates typical blood pressure waveform data captured using USB port streaming. FIG. 58 (5800) provides additional detail within this display waveform data. FIG. 59 (5900) illustrates a fine detail image captured using the USB streaming data. Finally, FIG. 60 (6000) illustrates a super-fine detail waveform capture. Note that these waveforms may be post-processed in some circumstances to determine abnormalities in the waveform for the purposes of patient diagnostic care. In some circumstance these waveforms may be processed in real-time to achieve these same results, permitting physicians to diagnose patient conditions while one or more BPMs are attached to the patient.

Blood Pressure Fidelity Testing (6100, 6200, 6300, 6400)

Figure 61:
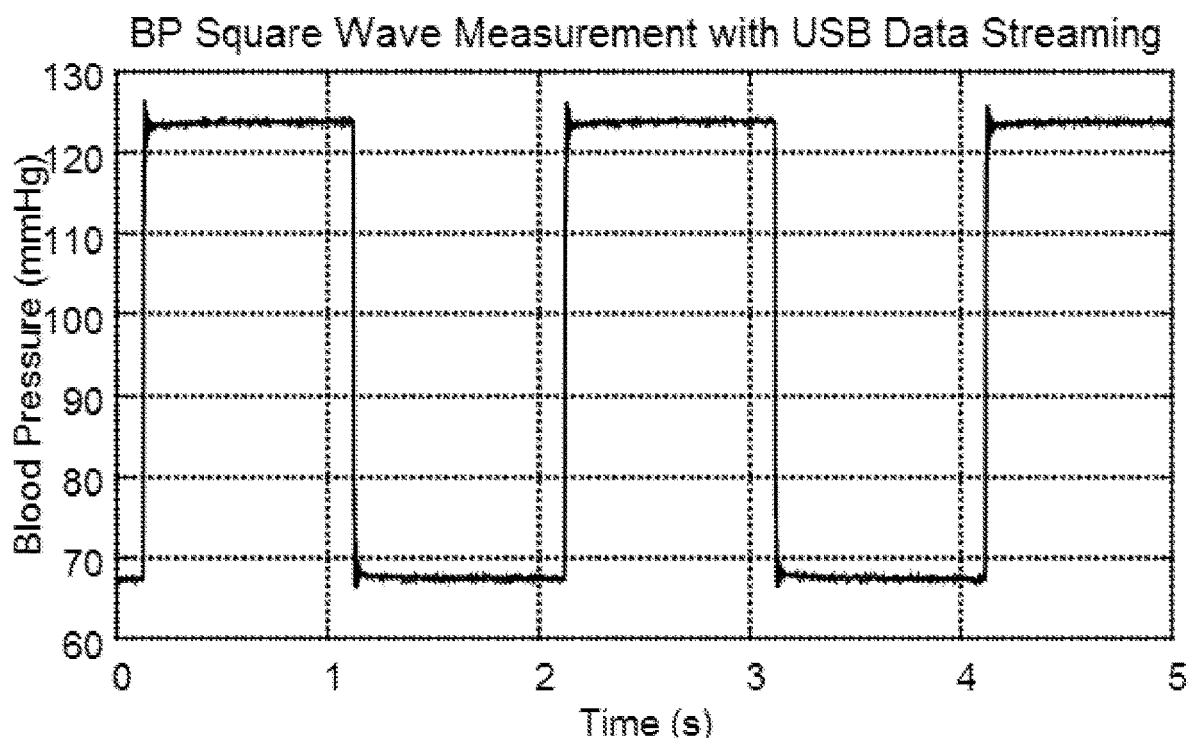
FIG. 61 illustrates an exemplary mechanically generated square-wave blood pressure measurement overview result graph obtained via USB data streaming from a preferred exemplary embodiment of the present invention.
Figure 64:
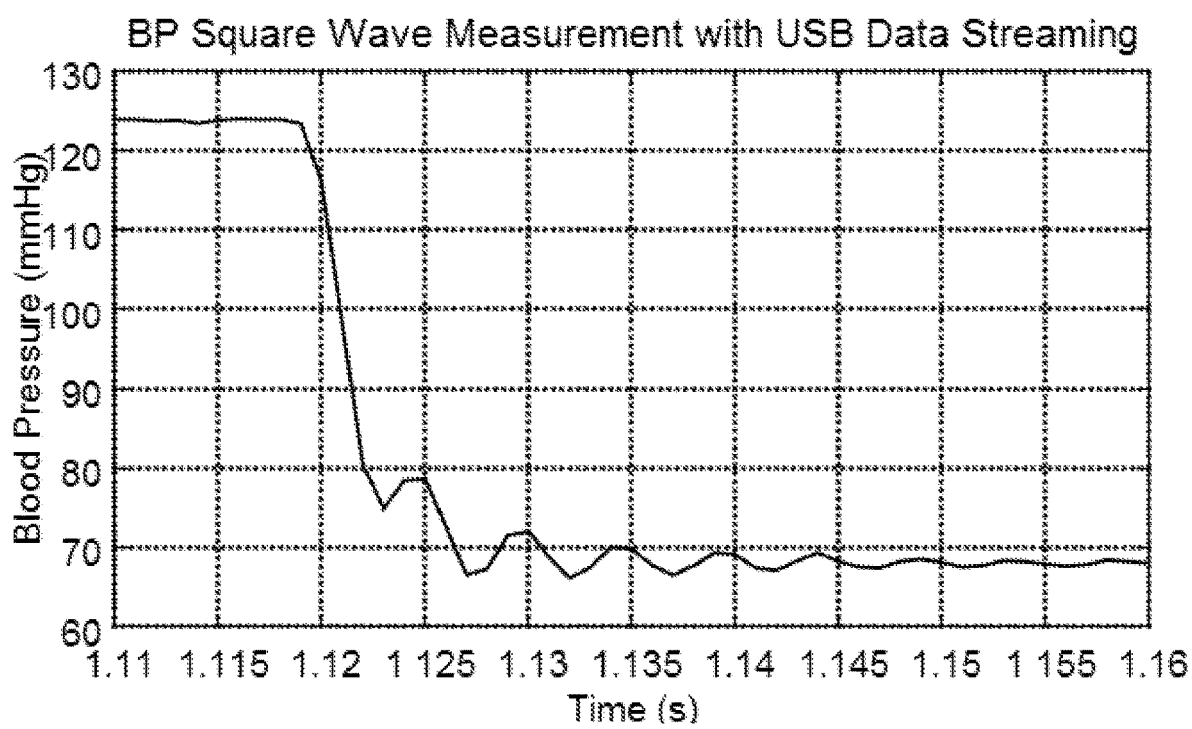
FIG. 64 illustrates an exemplary mechanically generated square-wave falling edge blood pressure measurement fine detail result graph obtained via USB data streaming from a preferred exemplary embodiment of the present invention.

The fidelity with which blood pressure measurement (BPM) systems are capable using the present invention teachings may be best illustrated by viewing the mechanically generated square wave BP measurement data generally illustrated in FIG. 61 (6100)-FIG. 64 (6400). Here the waveforms are derived from USB port streamed data obtained from a preferred exemplary embodiment applied to a blood pressure monitor (BPM) system, with the data input to the system driven by a mechanical pressure pump simulating a square blood pressure characteristic.

Figure 62:
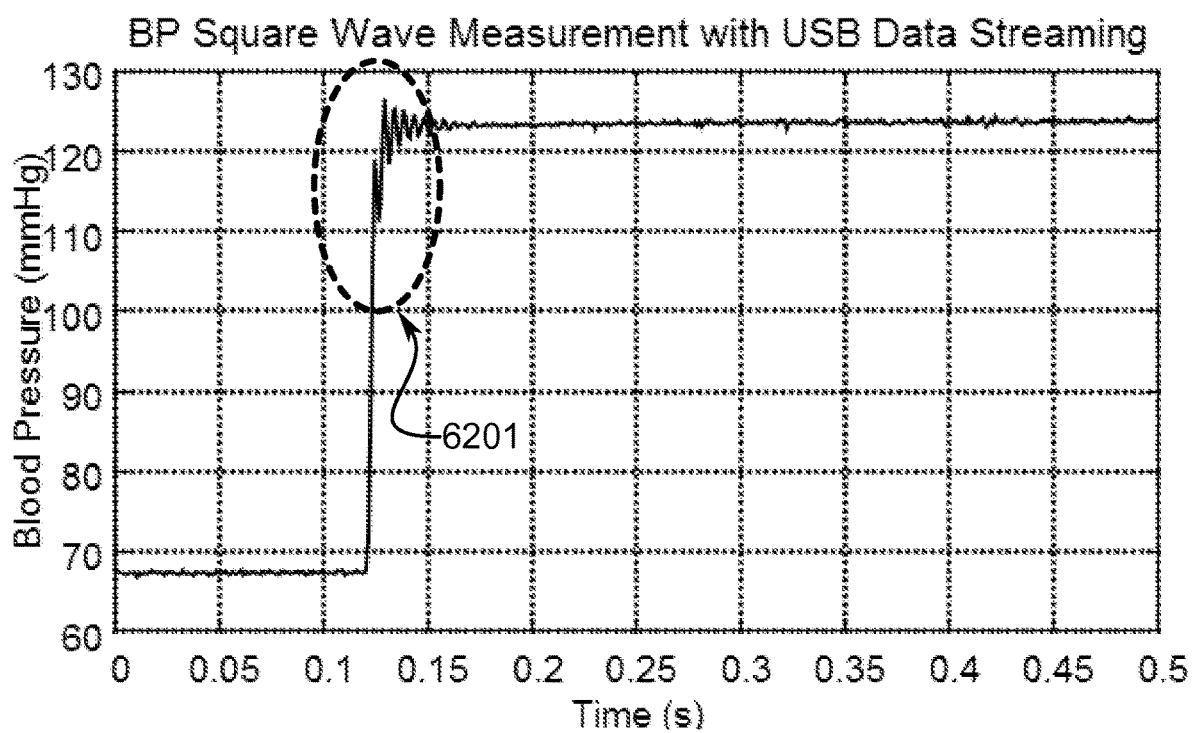
FIG. 62 illustrates an exemplary mechanically generated square-wave blood pressure measurement detail result graph obtained via USB data streaming from a preferred exemplary embodiment of the present invention.

Within this fidelity testing context, FIG. 61 (6100) illustrates an overview of the measured blood pressure characteristic. FIG. 62 (6200) details the rising edge of the blood pressure characteristic indicating a possible anomaly (6201) requiring further investigation. FIG. 63 (6300) generally illustrates a finer detail of this possible anomaly, with FIG. 64 (6400) generally illustrating a similar anomaly on the falling edge of the blood pressure characteristic.

The exact nature of the anomalies illustrated in FIG. 61 (6100)-FIG. 64 (6400) are irrelevant for the purposes of this general illustration, but serve to note that fine detail within a given blood pressure measurement can be determined in real-time and analyzed to determine patient diseases or other medical conditions. The fidelity of measurements taken using this technique along with a high sampling rate (500-1000 samples/second or greater) produces a better characterization of the exact fluid dynamics occurring within the measured pressure domain being investigated within the patient. This measurement fidelity is a feature not possible using prior art Wheatstone Bridge sensors due to the inherent noise characteristics of these devices and their susceptibility to external electromagnetic interference.

Generalized Computer Usable Medium

In various alternate embodiments, the present invention may be implemented as a computer program product for use with a computerized computing system. Those skilled in the art will readily appreciate that programs defining the functions defined by the present invention can be written in any appropriate programming language and delivered to a computer in many forms, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the present invention system embodiments can incorporate a variety of computer readable media that comprise computer usable medium having computer readable code means embodied therein. One skilled in the art will recognize that the software associated with the various processes described herein can be embodied in a wide variety of computer accessible media from which the software is loaded and activated. Pursuant to In re Beauregard, 35 USPQ2d 1383 (U.S. Pat. No. 5,710,578), the present invention anticipates and includes this type of computer readable media within the scope of the invention. Pursuant to In re Nuijten, 500 F.3d 1346 (Fed. Cir. 2007) (U.S. patent application Ser. No. 09/211,928), the present invention scope is limited to computer readable media wherein the media is both tangible and non-transitory.

CONCLUSION

A transducer interface system/method allowing conversion from an analog sensor input to a standardized analog output interface has been disclosed. In some preferred embodiments the system/method permits a fiber optic pressure sensor to be interfaced to a standard patient care monitor (PCM) system using standardized Wheatstone Bridge analog interface inputs. Within this context the Wheatstone Bridge sensed output is defined by stimulus from the PCM and modulation of bridge element values by the conditioned output of an analog pressure sensor. The use of analog-to-digital-to-analog conversion in this transducer interface permits retrofitting of PCM devices having analog Wheatstone Bridge inputs with advanced patient monitoring sensors without the need for specialized modifications to the baseline PCM data collection framework. Methods disclosed herein include techniques to connect arbitrary types/ numbers of analog sensors to traditional PCM systems without the need for PCM system hardware/software modifications.

Claims Interpretation

The following rules apply when interpreting the CLAIMS of the present invention:
The CLAIM PREAMBLE should be considered as limiting the scope of the claimed invention.
"WHEREIN" clauses should be considered as limiting the scope of the claimed invention.
"WHEREBY" clauses should be considered as limiting the scope of the claimed invention.
"ADAPTED TO" clauses should be considered as limiting the scope of the claimed invention.
"ADAPTED FOR" clauses should be considered as limiting the scope of the claimed invention.
The term "MEANS" specifically invokes the means-plus-function claims limitation recited in 35 U.S.C. § 112(f) and such claim shall be construed to cover the corresponding structure, material, or acts described in the specification and equivalents thereof.
The phrase "MEANS FOR" specifically invokes the means-plus-function claims limitation recited in 35 U.S.C. § 112(f) and such claim shall be construed to cover the corresponding structure, material, or acts described in the specification and equivalents thereof.
The phrase "STEP FOR" specifically invokes the step-plus-function claims limitation recited in 35 U.S.C. § 112(f) and such claim shall be construed to cover the corresponding structure, material, or acts described in the specification and equivalents thereof.
The phrase "AND/OR" in the context of an expression "X and/or Y" should be interpreted to define the set of "(X and Y)" in union with the set "(X or Y)" as interpreted by Ex Parte Gross (USPTO Patent Trial and Appeal Board, Appeal 2011-004811, Ser. No. 11/565,411, ("'and/or' covers embodiments having element A alone, B alone, or elements A and B taken together").
The claims presented herein are to be interpreted in light of the specification and drawings presented herein with sufficiently narrow scope such as to not preempt any abstract idea.
The claims presented herein are to be interpreted in light of the specification and drawings presented herein with sufficiently narrow scope such as to not preclude every application of any idea.
The claims presented herein are to be interpreted in light of the specification and drawings presented herein with sufficiently narrow scope such as to preclude any basic mental process that could be performed entirely in the human mind.
The claims presented herein are to be interpreted in light of the specification and drawings presented herein with sufficiently narrow scope such as to preclude any process that could be performed entirely by human manual effort.

What is claimed is:

1. A transducer to patient care monitor (PCM) interface system for coupling an analog sensor configured to be used within a patient to measure pressure to a PCM, the analog sensor comprising a fiber optic cable, a diaphragm on its distal end, and a fiber optic connector including a non-volatile memory containing gauge factors specific to the analog sensor, wherein the interface system comprises:
a digital computing device configured to:
initiate a status function when the analog sensor is connected to the PCM via the interface system to determine whether the analog sensor is exposed to atmospheric pressure by determining whether an observed pressure from the analog sensor is stable over a predetermined period of time; and
assign an atmospheric compensation zero value based on the status function, wherein assigning the atmospheric compensation zero value comprises:
in response to determining the analog sensor is exposed to atmospheric pressure by determining the observed pressure from the analog sensor is stable over the predetermined period of time, calculating a current atmospheric compensation zero value based on the observed pressure; storing the current atmospheric compensation zero value in the non-volatile memory; and assigning the current atmospheric compensation value as the atmospheric compensation zero value; and
in response to determining the analog sensor is not exposed to atmospheric pressure by determining the observed pressure from the analog sensor is not stable over the predetermined period of time, retrieving, from the non-volatile memory, a previous atmospheric compensation zero value calculated based on an observation of atmospheric pressure from the analog sensor at an earlier time; and assigning the previous atmospheric compensation zero value as the atmospheric compensation zero value;
an A/D converter configured to sample an analog signal from said analog sensor and convert said analog signal to a digital sensor value, wherein the digital computing device is further configured to receive the digital sensor value from the A/D converter, apply the gauge factors and the assigned atmospheric compensation zero value to the digital sensor value to produce a digital compensated sensor value, and control a display on a visual status indicator based on the digital compensated sensor value;
a bridge excitation converter configured to receive an analog Wheatstone Bridge excitation signal from the PCM and convert the analog Wheatstone Bridge excitation signal to produce a bridge excitation value; and
a bridge sense D/A converter configured to receive the digital compensated sensor value from the digital computing device and the bridge excitation value from the bridge excitation converter, generate an analog compensated sensor value, and scale the analog compensated sensor value by said bridge excitation value to produce a converted analog Wheatstone Bridge sense signal that is provided to the PCM.

2. The transducer interface system of claim 1, wherein said non-volatile memory comprises a RFID TAG memory in which said gauge factors are stored.

3. The transducer interface system of claim 1, wherein said digital computing device is configured to display to said visual status indicator a pressure value that is selected from a plurality of said digital compensated sensor values within a sampling period.

4. The transducer interface system of claim 3, wherein said digital computing device is configured to display to said visual status indicator a pressure value that is computed from an analysis of a plurality of said digital compensated sensor values within a sampling period.

5. The transducer interface system of claim 3, wherein said digital computing device is configured to display to said visual status indicator a pressure value that is computed from a periodic analysis of a plurality of said digital compensated sensor values within a sampling period.

6. The transducer interface system of claim 1, wherein said digital computing device is configured to display to said visual status indicator a peak pressure value that is computed from an analysis of a plurality of said digital compensated sensor values within a sampling period.

7. The transducer interface system of claim 1, wherein said digital computing device is configured to display to said visual status indicator a mean pressure value that is computed from an analysis of a plurality of said digital compensated sensor values within a sampling period.

8. The transducer interface system of claim 1, wherein said digital computing device is configured to display to said visual status indicator systolic blood pressure, diastolic blood pressure, mean blood pressure, and heart rate values that are computed from an analysis of a plurality of said digital compensated sensor values.

9. The transducer interface system of claim 1, wherein said digital computing device is configured to stream a plurality of said digital compensated sensor values to said visual status indicator.

10. The transducer interface system of claim 1, wherein said digital computing device is configured to simultaneously display to said visual status indicator a waveform of a plurality of said digital compensated sensor values and text depicting one or more of said digital compensated sensor values.

11. A transducer to patient care monitor (PCM) interface method comprising:
coupling an analog sensor to a PCM via an interface, wherein the analog sensor is configured to be used within a patient to measure pressure and comprises a fiber optic cable having a diaphragm on its distal end, and a fiber optic connector including a non-volatile memory containing gauge factors specific to the analog sensor, and the interface comprises a digital computing device;
initiating a status function with said digital computing device when the analog sensor is connected to the PCM via the interface to determine whether the analog sensor is exposed to atmospheric pressure by determining whether an observed pressure from the analog sensor is stable over a predetermined period of time; and
assigning an atmospheric compensation zero value with said digital computing device based on the status function, wherein the digital computing device is configured to assign the atmospheric compensation zero value by:
in response to determining the analog sensor is exposed to atmospheric pressure by determining the observed pressure from the analog sensor is stable over the predetermined period of time, calculating a current atmospheric compensation zero value based on the observed pressure; storing the current atmospheric compensation zero value in the non-volatile memory; and assigning the current atmospheric compensation value as the atmospheric compensation zero value; and
in response to determining the analog sensor is not exposed to atmospheric pressure by determining the observed pressure from the analog sensor is not stable over the predetermined period of time, retrieving, from the non-volatile memory, a previous atmospheric compensation zero value calculated based on an observation of atmospheric pressure from the analog sensor at an earlier time; and assigning the previous atmospheric compensation zero value as the atmospheric compensation zero value;
sampling an output signal from said analog sensor inserted within said patient using an A/D converter of the interface to produce a digital sensor output value that is provided to the digital computing device;
applying said gauge factors and said assigned atmospheric compensation zero value to said digital sensor output value using the digital computing device to produce a digital sensor compensated value;
sensing an analog Wheatstone Bridge excitation voltage signal from the PCM with a bridge excitation converter of the interface that converts the analog Wheatstone Bridge excitation voltage signal to form a bridge excitation value;
converting said digital sensor compensated value from digital to analog using a D/A converter of the interface to produce an analog sensor compensated value; and
scaling said analog sensor compensated value by said bridge excitation value using the D/A converter to produce a converted Wheatstone Bridge sense signal that is provided to the PCM.

12. The transducer interface method of claim 11, wherein said analog sensor comprises a Fabry-Perot pressure sensor positioned proximal to the distal end of a medical device, said medical device selected from a group consisting of a catheter, catheter incorporating a mounted balloon, vascular sheath, ventriculostomy catheter, ventricular shunt catheter, lumbar drain, and intracranial pressure monitor structure.

13. The transducer interface method of claim 11, wherein said analog sensor comprises a plurality of Fabry-Perot pressure sensors located within a medical device, said medical device selected from a group consisting of a catheter, catheter incorporating a mounted balloon, vascular sheath, ventriculostomy catheter, ventricular shunt catheter, lumbar drain, and intracranial pressure monitor structure.

14. The transducer interface method of claim 11, wherein said analog sensor is an invasive arterial blood pressure (IBP) sensor.

15. The transducer interface method of claim 11, wherein said analog Wheatstone Bridge excitation voltage signal is generated by the PCM.

16. The transducer interface method of claim 11, wherein said converted Wheatstone Bridge sense signal is displayed using the PCM.

17. The transducer interface method of claim 11, wherein said non-volatile memory comprises a RFID TAG memory in which said gauge factors are stored.

18. The transducer interface method of claim 11, wherein said non-volatile memory comprises an EEPROM memory in which said gauge factors are stored.

19. The transducer interface method of claim 11, wherein said digital sensor compensated value is transmitted to a display device that indicates systolic blood pressure, diastolic blood pressure, mean blood pressure, and heart rate values.

20. The transducer interface method of claim 11, wherein said digital sensor compensated value is streamed via a hardwired serial interface to a remote computer system for analysis of said digital sensor value derived from said analog sensor.

21. The transducer interface method of claim 11, wherein said digital sensor compensated value is streamed via a wireless serial interface to a remote computer system for analysis of said digital sensor value derived from said analog sensor.

22. The transducer interface method of claim 11, wherein
said interface comprises a plurality of A/D converters to permit multichannel input data collection from a plurality of analog sensors; and
said digital computing device comprises multiple digital inputs to enable input processing of data received from each of the plurality of A/D converters.

23. The transducer interface method of claim 11, wherein
said interface comprises a plurality of A/D converters to permit multichannel input data collection from a plurality of analog sensors;
said interface comprises a plurality of bridge excitation converters and D/A converters to permit multichannel data collection;
said digital computing device comprises multiple digital inputs to enable input processing of data received from each of the plurality A/D converters;
said digital computing device comprises multiple digital inputs to enable input processing of data received from each of the plurality of the bridge excitation converters; and
said digital computing device comprises multiple digital outputs to enable output processing of data to each of the plurality of the D/A converters.

24. The transducer interface method of claim 11, wherein said scaling of said analog compensated sensor value is accomplished by combining said bridge excitation value with said digital compensated sensor value to generate said converted analog Wheatstone Bridge sense signal.

* * * * *